(12) United States Patent
Chuenkova et al.

(10) Patent No.: US 7,060,676 B2
(45) Date of Patent: Jun. 13, 2006

(54) T. CRUZI-DERIVED NEUROTROPHIC AGENTS AND METHODS OF USE THEREFOR

(75) Inventors: Marina Chuenkova, Allston, MA (US); Miercio A. Pereira, Chestnut Hill, MA (US)

(73) Assignee: Trustees of Tufts College, Medford, MA (US)

( * ) Notice: Subject to any disclaimer, the term of this patent is extended or adjusted under 35 U.S.C. 154(b) by 0 days.

(21) Appl. No.: 09/745,008

(22) Filed: Dec. 20, 2000

(65) Prior Publication Data

US 2002/0137667 A1 Sep. 26, 2002

Related U.S. Application Data

(60) Provisional application No. 60/172,881, filed on Dec. 20, 1999.

(51) Int. Cl.
*A61K 38/28* (2006.01)
*A61K 38/00* (2006.01)
*C07K 14/00* (2006.01)
*C07K 16/00* (2006.01)

(52) U.S. Cl. .......................................... 514/4; 530/300
(58) Field of Classification Search ................ 424/94.1; 530/300, 350
See application file for complete search history.

(56) References Cited

U.S. PATENT DOCUMENTS

| | | | |
|---|---|---|---|
| 5,980,885 A | 11/1999 | Weiss et al. ............. | 424/93.21 |
| 6,033,660 A | 3/2000 | Mather et al. ............. | 424/93.7 |
| 6,037,320 A | 3/2000 | Rosenthal ...................... | 514/2 |
| 6,054,294 A | 4/2000 | Chang ........................ | 435/69.1 |
| 6,093,802 A | 7/2000 | Lin et al. .................... | 530/399 |
| 6,124,328 A | 9/2000 | Armistead ................... | 514/354 |
| 6,143,714 A | 11/2000 | Wong et al. ..................... | 514/2 |
| 6,167,888 B1 | 1/2001 | Tuszynski et al. ........... | 128/898 |
| 6,172,086 B1 | 1/2001 | Zelle et al. ................... | 514/332 |
| 6,174,862 B1 | 1/2001 | Brenneman ................... | 514/15 |
| 6,177,402 B1 | 1/2001 | Bartlett et al. ................. | 514/2 |
| 6,214,796 B1 | 4/2001 | Finklestein ................... | 514/12 |

OTHER PUBLICATIONS

Stratagene, Product Info—pBlueScript® II Phagemid Vector obtained at "www.stratagene.com/products/displayProduct.aspx?pid=267".*
ATCC Accession No. 87047 product info and map obtained at "www.atcc.org/SearchCatalogs/directdetail.cfm?collection=mb-vector&atccNum=87047".*
Genebank Accession No. AJ002174, "Trypanosoma Cruzi Trans-Sialidase Gene, Clone 19y, 5'-region," (1999) [online], [retrieved on Apr. 18, 2001]. Retrieved from the internet: <URL:http://www.ncbi.nlm.nih.gov>.

Genebank Accession No. M61732, "T. Cruzi Neuraminadose (TCNA) Gene, Complete cds," (1994) [online], [retrieved on Apr. 18, 2001]. Retrieved from the Internet: <URL:http://www.ncbi.nlm.nih.gov>.
"Table of Contents," *J. Exp. Med.* 190(12) (1999) [online], [retrieved on Dec. 13, 1999]. Retrieved from the Internet: <URL:http://intl.jem.org/future/190.12.shtml>.
Chuenkova, M.V. and Pereira, M.A., "A Trypanosomal Protein Synergizes with the Cytokines Ciliary Neurotrophic Factor and Leukemia Inhibitory Factor to Prevent Apoptosis of Neuronal Cells," *Molecular Biology of the Cell*, 11:1487-1498 (2000).
Prasad, K.N., "Differentiation of Neuroblastoma Cells: A Useful Model for Neurobiology and Cancer," *Biol. Rev.*, 66:431-451 (1991).
Schenkman, S. et al., "Structural and Functional Properties of Trypanosoma Trans-Sialidase," *Annu. Rev. Microbiol.*, 48:499-523 (1994).
Pereira, M.E. et al., "The Trypanosoma Cruzi Neuraminidase Contains Sequences Similar to Bacterial Neuraminidases, YWTD Repeats of the Low Density Lipoprotein Receptor, and Type III Modules of Fibronectin," *J. Exp. Med.*, 174(1):179-191 (1991).
Saavedra, E. et al., "The Trypanosoma Cruzi Trans-Sialidase, Through Its COOH-Terminal Tandem Repeat, Upregulates Interleukin 6 Secretion in Normal Human Intestinal Microvascular Endothelial Cells and Peripheral Blood Mononuclear Cells," *J. Exp. Med.*, 190(12):1825-1836 (1999).
Chuenkova, M. et al., "*trans*-Sialidase of *Trypanosoma cruzi*: Location of Galactose-Binding Site(s)," Biochemical and Biophysical Research Communications, 262:549-556 (1999), Aug.

* cited by examiner

*Primary Examiner*—Sharon Turner
(74) *Attorney, Agent, or Firm*—Hamilton, Brook, Smith & Reynolds, P.C.

(57) ABSTRACT

The invention relates to *T. cruzi* trans-sialidase (TS) and to the neurotrophic and IL-6 secretion-inducing activities of the protein. TS, neurotrophic variants and/or neurotrophic peptides based upon the sequence of TS can be administered to a mammal to directly or indirectly provide neurotrophic support for neurons. A mammalian neurotrophic factor (e.g., CNTF, LIF) can be co-administered with the TS, neurotrophic variant and/or neurotrophic peptide. TS, IL-6 secretion-inducing variants and/or IL-6 secretion-inducing peptides based upon the sequence of TS can be administered to a mammal to induce the secretion of IL-6. TS, active variants and/or active peptides can be administered to a mammal having an acquired or congenital condition characterized by neuronal degeneration or to a mammal that has experienced trauma to the brain, spinal cord or peripheral nerves. The invention also relates to neurotrophic and IL-6 secretion-inducing variants of TS and to neurotrophic and IL-6 secretion-inducing peptides. The invention also relates to compositions comprising TS, active variants thereof and/or active peptides and a physiologically acceptable carrier.

8 Claims, 38 Drawing Sheets

| | | | | |
|---|---|---|---|---|
| 1 | tgttcccctt | ttctcttccc | aactttctcc | ggcggcaatc | ccctgcaaa | gagacgatct |
| 61 | tgacaccatt | gttttaggca | tctagaagt | tctacaaaca | acgcccgaag | gacacacagg |
| 121 | caggcaccga | ctaccatggg | gaaaacagtc | gttgtggcca | gtaggatgtt | ctggctaatg |
| 181 | tttttcgtgc | cgcttcttct | tgcgatctgc | cccagcgagc | cggtgtacgc | cttggcaccc |
| 241 | ggatcgagcc | gagttgagct | gtttaagcgt | aagaattcga | cggtgccgtt | tgaagacaag |
| 301 | gccggcaaag | tcaccgagcg | ggttgtccac | tcgttccgcc | tccccgccct | tgttaatgtg |
| 361 | gacggggtga | tggttgccat | cgcggacgct | cgctacgaca | catccaatga | caactccctc |
| 421 | attgatacgg | tggcgaagta | cagcgtggaa | cgtggggaga | cgtgggagac | ccaaattgcc |
| 481 | atcaagaaca | gccgtgtatc | gtctgtttct | cgtggtggtg | atcccaccgt | gattgtgaag |
| 541 | ggcaacaagc | tttacgtcct | ggttggaagc | tactatagtt | cgagaagcta | ctggtcgtcg |
| 601 | catgtgatg | cgagagactg | ggatattctg | cttgccgttg | gtgaggtcac | gaagtccact |
| 661 | gcgggcggca | agataactgc | gagtatcaaa | tggggagcc | ccgtgtcact | gaagaagttt |
| 721 | tttccggcag | aaatggaagg | catgcacaca | aatcaatttc | ttggcggcgc | gggtgttgcc |
| 781 | attgtagcgt | ccaacgggaa | tcttgtgtac | cctgtgcagg | ttacgaacaa | aaagaagcaa |
| 841 | gtttctctcca | agatcttcta | ctcgaagat | gatgcaaga | cgtggaagtt | tgggaaggt |
| 901 | aggagcgatt | ttggctgctc | tgaacctgtg | gcccttgagt | gggaggggaa | gctcatcata |
| 961 | aacaccgag | ttgactgaa | acgcgtctg | gtgtacgagt | ccagtgacat | ggagaaaccg |
| 1021 | tgggtggagg | ctgtcggaac | cgtctcgcgt | gtgtgggcc | cctcaccaaa | atcgaaccag |
| 1081 | cccggcagtc | agagcagctt | cactgccgtg | accatcgaag | gaatcgtgt | gatgctcttc |
| 1141 | acacacccgc | tgaattttaa | gggaaggtgg | ctgcgcgacc | gactgaacct | ctggctgacg |
| 1201 | gataaccagc | gcatttataa | cgttgggcaa | gtatccattg | gtgatgaaaa | ttccgcctac |
| 1261 | agctccgtcc | tgtacaagga | tgataagctg | tactgtttgc | atgagatcaa | cacggacgag |
| 1321 | gtgtacagcc | ttgttttgc | acgcctggtt | ggcgagctac | ggatcattaa | atcagtgctg |
| 1381 | cggtcctgga | agaattggga | cagccacctg | tccagcattt | gcaccccttgc | tgatccagcc |
| 1441 | gcttcgtcgt | cagagagtgt | ttgtggtccc | gctgtcacca | cggttggtct | tgttggcttt |
| 1501 | ttgtccggca | acgcctccca | aaacgtatgg | gaggatgcgt | accgctgcgt | caacgcaagc |
| 1561 | acgcaaatg | tcgaacggt | ttgaagtttg | cggggttg | cggaggagcg |
| 1621 | ctttggccgg | tgagccagca | gggcagaat | cagcggtatc | gtttgcaaa | ccacgcgttc |
| 1681 | acgctggtgg | cgtcggtgac | gattcacgag | gctcacgggg | ccgcgagtcc | cttgctggt |
| 1741 | gcgagcctgg | actcttctgg | cggcaaaaaa | ctcctggggc | tctcgtacga | cgagaagcac |

FIGURE 1A

```
1801  cagtggcagc caatatacgg atcaacgccg gtgacgccga cgggatcgtg ggagacgggt
1861  aaaaggtacc acttggttct tacgatggcg aataaaattg gctccgtgta cattgatgga
1921  gaacttctgg agggttcagg acagaccgtt gtgccagacg ggaggacgcc tgacatctcc
1981  cacttctacg ttggcgggta taaaggagt gatatgccaa ccataagcca cgtgacggtg
2041  aataatgttc ttctttacaa ccgacagctg aataccgagg agatcaggac cttgttcttg
2101  agccaggacc ttattggcac ggaagcacac atg
```

FIGURE 1B

```
  1 MGKTVVVASR MFWLMFFVPL LLAICPSEPA YALAPGSSRV ELFKRKNSTV PFEDKAGKVT
 61 ERVVHSFRLP ALVNVDGVMV AIADARYDTS NDNSLIDTVA KYSVDDGETW ETQIAIKNSR
121 VSSVSRVVDP TVIVKGNKLY VLVGSYYSSR SYWSSHGDAR DWDILLAVGE VTKSTAGGKI
181 TASIKWGSPV SLKKFFPAEM EGMHTNQFLG GAGVAIVASN GNLVYPVQVT NKKKQVFSKI
241 PYSEDDGKTW KFGKGRSDFG CSEPVALEWE GKLIINTRVD WKRRLVYESS DMEKPWVEAV
301 GTVSRVWGPS PKSNQPGSQS SFTAVTIEGM RVMLFTHPLN FKGRWLRDRL NLWLTDNQRI
361 YNVGQVSIGD ENSAYSSVLY KDDKLYCLHE INTDEVYSLV FARLVGELRI IKSVLRSWKN
421 WDSHLSSICT PADPAASSSE SGCGPAVTTV GLVGFLSGNA SQNVWEDAYR CVNASTANAE
481 RVRNGLKFAG VGGGALWPVS QQGQNQRYRF ANHAFTLVAS VTIHEAPRAA SPLLGASLDS
541 SGGKKLLGLS YDEKHQWQPI YGSTPVTPTG SWETGKRYHL VLTMANKIGS VYIDGELLEG
601 SGQTVVPDGR TPDISHFYVG GYKRSDMPTI SHVTVNNVLL YNRQLNTEEI RTLFLSQDLI
661 GTEAHM
```

P-Akt (Ser473)

B

P-Akt (Ser473)

C

```
   1  AAAGACCGTT GGAAGAAGAA AGAAGGTTCC GGAGCGTGGC CACCACCAAC GATGAACTGC
  61  CACAATTGCG TGCTGTCCGC GGGCGGTACC CGGCGCTTTG AGCCCACGGC GACTTGTGTG
 121  TTCCCCTTTC TCTTCCCACT TTCTCCGCGG CAATCCCCCT GCAAAGAGAC GATCTTGACA
 181  CCATTGTTTT AGGCATAATA GAAGTTCTAC AAACAACGCC CGAAGGACAC ACAGGCAGGC
 241  ACCGACTACG ATGGGGAAAA CAGTCGTTGT GGCCAGTAGG ATGTTCTGGC TAATGTTTTT
 301  CGTGCCGCTT CTTCTTGCGA TCTGCCCCAG CGAGCCCGCG TACGCCCTGG CACCCGGATC
 361  GAGCCGAGTT GAGGGTTTAA GCGTAAGAAT TCGACGGTGC CGTTTGAAGA CAAGGCCGGC
 421  AAAGTCACCG AGCGGGTTGT CCACTCGTTC CGCTTCCCCG CCCTTGTTAA TGTGGACGGG
 481  GTGATGGTTG CCATCGCGGA CGCTCGCTAC GAAACATCCA GTGAAAACTC CCTCATTGAT
 541  ACGGTGGCGA AGTACAGCGT GGACGATGGG GAGACGTGGG AGACCCAAAT TGCCATCAAG
 601  AACAGCCGTG TATCGTCTGT TTCTCGTGTG GTGGATCCCA CCGTGATTGT GAAGGGCAAC
 661  AAGCTTTACG TCCTGGTTGG AAGCTACTAT AGTTCGAGAA GCTACTGGTC GTCGCATGGT
 721  GATGCGAGAG ACTGCGAGTAT TCTGCTTGCC GTTGGTGAGG TCACGAAGTC CACTGCGGGC
 781  GGCAAGATAA CTGCGAGTAT CAAATGGGGG AGCCCCGTGT CACTGAAGAA GTTTTTTCCG
 841  GCAGAAATGG AAGGCATGCA CACAAATCAA TTTCTTGGCG GCGCGGGTGT TGCCATTGTA
 901  GCGTCCAACG GGAATCTTGT GTACCCTGTG CAGGTTACGA ACAAAAGGAA GCAAGTTTTC
 961  TCCAAGATCT TCTACTCGGA AGATGATGGC AAGACGTGGA AGTTTGGGAA GGGTAGGAGC
1021  GATTTTGGCT GCTCTGAACC TGTGGCCCTT GAGTGGGAGG GAAGCTCAT CATAAACACC
1081  CGAGTTGACT GGAAACGCCG TCTGGTGTAC GAGTCCAGTG ACATGGAGAA ACCGTGGGTG
1141  GAGGCTGTCG GAACCGTCTC GCGTGTGTGG GGCCCCTCAC CAAAATCGAA CCAGCCCGGC
1201  AGTCAGACGA GCTTCACTGC CGTGACCATC GAAGGAATGC GTGTGATGCT CTTCACACAC
1261  CCGCTGAATT TTAAGGGAAG GTGCGTGCGC GACCGACTGA ACCTCTGGCT GACGGATAAC
1321  CAGCGCATTT ATAACGTTGG GCAAGTATCC ATTGGTGATG AAAATTCCGC CTACAGCTCC
1381  GTCCTGTACA AGGATGATAA GCTGTACTGT TTGCATGAGA TCAACACGGA CGAGGTGTAC
1441  AGCCTTGTTT TTGCACGCCT GGTTGGCGAG CTACGGATCA TTAAATCAGT GCTGCGGTCC
1501  TGGAAGAATT GGACAGCCAC CTGTCCAGCA TTTGCACCCC TGCTGATCCA GCCGCTTCGT
1561  CGTCAGAGAG TGGTTGTGGT CCCGCTGTCA CCACGGTTGG TCTTGTTGGC TTTTTGTCGG
1621  CAACGCCTCC CAAAACGTAT GGGAGGATCG TACCGCTGCG TCAACGCAAG CACGGCAAAT
1681  GCGGAGAGGG TTCGGAACGG TTTGAAGTTT GCGGGGGTTG GCGGAGGAGC GCTTTGGCCG
1741  GTGAGCCAGC AGGGGCAGAA TCAGCGGTAT CGTTTTGCAA ACCACGCGTT CACGCTGGTG
1801  GCGTCGGTCA CGATTCACGA GGCTCCGAGG GCCGCGAGTC CCTTGCTGGG TGCGAGCCTG
1861  GACTCTTCTG GCGGCAAAAA ACTCCTGGGG CTCTCGTACG ACGAAGAGCA CCAGTGGCAG
1921  CCAATATACG GATCAACGCC GGTGACGCCG ACGGGATCGT GGGAGACGGG TAAAAGGTAC
1981  CACTTGGTTC TTACGATGGC GAATAAAATT GGCTCCGTGT ACATTGATGG AGAACTTCTG
2041  GAGGGTTCAG GACAGACCGT TGTGCCAGAC GGGAGGACGC CTGACATCTC CCACTTCTAC
2101  GTTGGCGGGT ATAAAAGGAG TGATATGCCA ACCATAAGCC ACGTGACGGT GAATAATGTT
2161  CTTCTTTACA ACCGACGACA GCTGAATACC GAGGAGATCA GGACCTTGTT CTTGAGCCAG
2221  GACCTTATTG GCACGGAAGC ACACATGGAC AGCAGCAGCG ACAGCAGTGC CCACAGTACG
2281  CCCTCAACTC CCGCTGACAG CAGTGCCCAC AGTACGCCCT CAACTCCCGT TGACAGCAGT
2341  GCCCACAGTA CGCCCTCGAC TCCCGCTGAC AGCAGTGCCC ACGGTACGCC CTCAACTCCC
2401  GTTGACAGCA GTGCCCACGG TACGCCCTCA ACTCCCGCTG ACAGCAGTGC CCACAGTACG
2461  CCCTCAACTC CCGTTGACAG CAGTGCCCAC AGTACGCCCT CAACTCCCGT TGACAGCAGT
2521  GCCCACAGTA CGCCCTCAAC TCCCGTTGAC AGCAGTGCCC ACGGTGCGCC CTCAACTCCC
2581  GCTGACAGCA GTGCCCACGG TACGCCCTCG ACTCCCGTTG ACAGCAGTGC CACGGTACG
2641  CCCTCGACTC CCGCTGACAG CAGTGCCCAC AGTACGCCCT CGACTCCCGC TGACAGCAGT
2701  GCCCACAGTA CGCCCTCGAC TCCCGCTGAC AGCAGTGCCC ACAGTACGCC CTCGACTCCC
2761  GTTGACAGCA GTGCCCACGG TACGCCCTCG ACTCCCGCTG ACAGCAGTGC CCACAGTACG
2821  CCCTCGACTC CCGCTGACAG CAGTGCCCAC GGTACGCCCT CAACTCCCGT TGACAGCAGT
2881  GCCCACAGTA CGCCCTCGAC TCCCGTTGAC AGCAGTACGCC CTCAACTCCC
2941  GTTGACAGCA GTGCCCACAG TACGCCCTCG ACTCCCGTTG ACAGCAGTGC CCACAGTACG
3001  CCCTCAACTC CCGTTGACAG CAGTGCCCAC AGTACGCCCT CGACTCCCGC TGACAGCAGT
3061  GCCCACAGTA CGCCCTCAAC TCCCGCTGAC AGCAGTGCCC ACGGTACGCC CTCAACTCCC
3121  GTTGACAGCA GTGCCCACAG TACGCCCTCG ACTCCGCTG ACAGCAGTGC CCACAGTACG
```

Figure 26A

```
3181  CCCTCAACTC CCGTTGACAG CAGTGCCCAC AGTACGCCCT CAACTCCCGC TGACAGCAGT
3241  GCCCACGGTA CGCCCTCAAC TCCCGTTGAC AGCAGTGCCC ACGGTACGCC CTCGACTCCC
3301  GCTGACAGCA GTGCCCACAG TACGCCCTCG ACTCCCGCTG ACAGCAGTGC CCACAGTACG
3361  CCCTCGACTC CCGCTGACAG CAGTGCCCAC AGTACGCCCT CAACTCCCGT TGACAGCAGT
3421  GCCCACAGTA CGCCCTCAAC TCCCGCTGAC AGCAGTGCCC ACAGTACGCC CTCAACTCCC
3481  GCTGACAGCA GTGCCCACAG TACGCCCTCG ACTCCCGCTG ACAGCAGTGC CCACAGTACG
3541  CCCTCAACTC CCGTTGACAG CAGTGCCCAC AGTACGCCCT CAACTCCCGC TGACAGCAGT
3601  GCCCACGGTA CGCCCTCGAC TCCCGCTGAC AGCAGTGCCC ACAGTACGCC CTCGACTCCC
3661  GTTGACAGCA GTGCCCACAG TACGCCCTCG ACTCCCGCTG ACAGCAGTGC CCACGGTACG
3721  CCCTCGACTC CCGCTGACAG CAGTGCCCAC AGTACGCCCT CGACTCCCGC TGACAGCAGT
3781  GCCCACGGTA CGCCCTCGAC TCCCGCTGAC AGCAGTGCCC ACAGTACGCC CTCAACTCCC
3841  GCTGGCAGCA GCGCCAATGG TACGGTTCTG ATTTTGCCCG ATGGCGCTGC ACTTTCGACC
3901  TTTTCGGGCG GAGGGCTTCT TCTGTGTGCG TGTGCTTTGC TGCTGCACGT GTTTTTTATG
3961  GCAGTTTTCT GATGTAGTGA GAGAGTCTCC TAACAAATGT AGATAAATTC ATAATTGTGG
4021  TGTGAACCGT TTGGGTAAAT GTGTGTGTGC GCTCTCATAA GGAAATGATT TCCAGTAATG
4081  TTTTTTTTTT GTTCTCGAAC ATTTTGAATA AATCTGCAGA CAGATGGGGA CGCGTAATTT
4141  GAATTTGTTT TTCAGCGTTC TTTTGTCACT GGCCCCTTGT TTAAGTGGAA CCGCGTTGCA
4201  ATGCGGCGAG GGCATTTCTC TGTTTTGATT TCCTTCTTTT TCTCCTTTGT GTTTCTTCAA
4261  TTTGACGGTT TGCACGCTGT GCGGTGGAGC GTTTTCCCTT GTGAAATAAG GGCCAACTGC
4321  TTCACAGTGG CACGAGGGCG CTCAAGAGAT CCGCGGGTCG CCAGTGACTC ACTTTGTGTG
4381  GCGCAGCTCG AGGAGGTGTC TGGCTGCTGT GGGGGCCTCG ATGGTTGCCA CTTCGCGAGT
4441  TTGCAACGAG CGTGCTTCTC GCGGAGGGAG CAGGCGAAAT ATTTTGTTTT TTTTTTTTGT
4501  TTTTTTTGTT TTTTGTTTT TGTGTGTGTG TGTAAGTTTT GGTTCAGTCT CCCTTGAACT
4561  GGGGGACGTT GGGCTTAATG GACCAAACTC TGATTCCCCT AAAACTTCTT TTGTTGGTTT
4621  TCTTTTGTTT TTGTTTTTGT GCTGCTGATT TGCACGCTTT CTCACTGTCA CCGAAGCGCG
4681  GCGGCGGTGT TTGAGTGCCC CCTCACGCTG CTGCTGTGGA ATTTGCGTTG CTTGCGGACA
4741  TTTCTGTTGG GTCGCATTGC TTTCTACTTC GTTTTTATT TTTGTGGTTT GGTCGAGGGG
4801  AGTGTGCAGC AGGGGGCGGG CCGAGATGCC TGTGGAGACA GCGACGTTGC GGGGACTCTC
4861  TCTCGGCCTC GTCATTCAAC AATCCATTGC GCAGCAGGTT GCCACGAACA CCAGCACCAA
4921  TATTTGTTCG TTTTCCCACT ATTACCGGCG CGTCTAGCCG CACGATGCCA TCTGGGTGCC
4981  GAGGAGGCGG TTGAGCAGCG GAAAAGGCTT CCTGCTATGA AGCGACTGCC ATTGACAGAA
5041  CTTTTAGCTG CGTGGATCTT CCTCAATGCC CAGCCGTTGG CGCGCAGCGG AGGTGCCTGG
5101  GCATTCTAGG AGCAGATGGC GAAAGGTTTC CTGCGCGTCA ACTGGCGTGT CTGTGGAGGT
5161  TGGCTATCCT CAGTCGGGAG ACCGCCTCCT GGCACCACAG AACGGGTAGC GGTAGTGTCT
5221  TGGCGAATAG TACAACGCCA CTTGTTGCTG ACTGGGCAGT AAAGCATGTC AGCGGGTCCG
5281  TGTGCCATAC GGGCGCATTC CATGTTCCGT GTGTTGTCCG GTTGCCATGG TCTGCGTCGC
5341  ATGCTGAGCC GCAGGCTCGT CAACATGCAC TCCACAATGT CCGTAAGAAA ACTCCCGGTG
5401  CAC
```

Figure 26B

```
   1 mvaiadarye tssenslidt vakysvddge twetgqiaikn srvssvsrvv dptvivkgnk
  61 lyvlvgsyys srsywsshgd ardwdillav gevtkstagg kitasikwgs pvslkkffpa
 121 emegmhtnqf lggagvaiva sngnlvypvq vtnkrkqvfs kifyseddgk twkfgkgrsd
 181 fgcsepvale wegkliintr vdwkrrlvye ssdmekpwve avgtvsrvwg pspksnqpgs
 241 qtsftavtie gmrvmlfthp lnfkgrcvrd rlnlwltdnq riynvgqvsi gdensayssv
 301 lykddklycl heintdevys lvfarlvgel riiksvlrsw knwtatcpaf aplliqplrr
 361 qrvvvvplsp rlvllafcrq rlpkrmggsy rcvnastana ervrnglkfa gvgggalwpv
 421 sqqgnqryr fanhaftlva svtiheapra asplgasld ssggkkllgl sydekhqwqp
 481 iygstpvtpt gswetgkryh lvltmankig svyidgelle gsgqtvvpdg rtpdishfyv
 541 ggykrsdmpt ishvtvnnvl lynrrqlnte eirtlflsgd ligteahmds ssdssahstp
 601 stpadssahs tpstpvdssa hstpstpvds sahgtpstpv padssahgtpst padssahgtp
 661 stpvdssahs tpstpvdssa hstpstpvds sahgapstpa dssahstpst pvdssahgtp
 721 stpadssahs tpstpadssa hstpstpvds sahstpstpv padssahgtpst padssahstp
 781 stpadssahg tpstpvdssa hstpstpvds sahgtpstpv padssahgtpst pvdssahgtp
 841 stpvdssahs tpstpadssa hstpstpvds sahgtpstpv padssahgtpst padssahstp
 901 stpvdssahs tpstpadssa hstpstpvds sahgtpstpa dssahstpst padssahstp
 961 stpadssahs tpstpadssa hgtpstpvds sahgtpstpa dssahstpst padssahstp
1021 stpvdssahs tpstpadssa hstpstpvds sahstpstpa dssahstpst padssahstp
1081 stpadssahs tpstpadssa hgtpstpads sahstpstpv dssahstpst padssahgtp
1141 sggglllcac allhvffma vf           gssangtvli lpdgaalstf
```

Figure 26C

SEQUENCE LISTING

<160> NUMBER OF SEQ ID NOS: 34

<210> SEQ ID NO 1
<211> LENGTH: 2133
<212> TYPE: DNA
<213> ORGANISM: Trypanosoma cruzi

<400> SEQUENCE: 1

```
tgttcccctt ttctcttccc aactttctcc ggcggcaatc cccctgcaaa gagacgatct      60
tgacaccatt gttttaggca taatagaagt tctacaaaca acgcccgaag gacacacagg     120
caggcaccga ctaccatggg gaaaacagtc gttgtggcca gtaggatgtt ctggctaatg     180
tttttcgtgc cgcttcttct tgcgatctgc cccagcgagc ccgcgtacgc cttggcaccc     240
ggatcgagcc gagttgagct gtttaagcgt aagaattcga cggtgccgtt tgaagacaag     300
gccggcaaag tcaccgagcg ggttgtccac tcgttccgcc tccccgccct tgttaatgtg     360
gacggggtga tggttgccat cgcggacgct cgctacgaca catccaatga caactccctc     420
attgatacgg tggcgaagta cagcgtggac gatggggaga cgtgggagac ccaaattgcc     480
atcaagaaca gccgtgtatc gtctgtttct cgtgtggtgg atcccaccgt gattgtgaag     540
ggcaacaagc tttacgtcct ggttggaagc tactatagtt cgagaagcta ctggtcgtcg     600
catggtgatg cgagagactg ggatattctg cttgccgttg gtgaggtcac gaagtccact     660
gcgggcggca agataactgc gagtatcaaa tgggggagcc ccgtgtcact gaagaagttt     720
tttccggcag aaatggaagg catgcacaca aatcaatttc ttggcggcgc gggtgttgcc     780
attgtagcgt ccaacgggaa tcttgtgtac cctgtgcagg ttacgaacaa aaagaagcaa     840
```

-continued

```
gttttctcca agatcttcta ctcggaagat gatggcaaga cgtggaagtt tgggaagggt      900
aggagcgatt ttggctgctc tgaacctgtg gcccttgagt gggagggaa gctcatcata      960 aacacccgag ttgactggaa acgccgtctg gtgtacgagt ccagtgacat ggagaaaccg     1020
tgggtggagg ctgtcggaac cgtctcgcgt gtgtgggcc cctcaccaaa atcgaaccag     1080
cccggcagtc agagcagctt cactgccgtg accatcgaag gaatgcgtgt gatgctcttc     1140
acacacccgc tgaattttaa gggaaggtgg ctgcgcgacc gactgaacct ctggctgacg     1200
gataaccagc gcatttataa cgttgggcaa gtatccattg gtgatgaaaa ttccgcctac     1260
agctccgtcc tgtacaagga tgataagctg tactgtttgc atgagatcaa cacgacgag     1320 gtgtacagcc ttgttttgc acgcctggtt ggcgagctac ggatcattaa atcagtgctg     1380
cggtcctgga agaattggga cagccacctg tccagcattt gcaccctgc tgatccagcc     1440 gcttcgtcgt cagagagtgg ttgtggtccc gctgtcacca cggttggtct tgttggcttt     1500
ttgtccggca acgcctccca aaacgtatgg gaggatgcgt accgctgcgt caacgcaagc     1560
acggcaaatg cggagagggt tcggaacggt ttgaagtttg cggggggttgg cggaggagcg     1620 cttggccgg tgagccagca ggggcagaat cagcggtatc gttttgcaaa ccacgcgttc     1680
acgctggtgg cgtcggtgac gattcacgag gctccgaggg ccgcgagtcc cttgctgggt     1740
gcgagcctgg actcttctgg cggcaaaaaa ctcctggggc tctcgtacga cgagaagcac     1800
cagtggcagc caatatacgg atcaacgccg gtgacgccga cgggatcgtg ggagacgggt     1860
aaaaggtacc acttggttct tacgatggcg aataaaattg gctccgtgta cattgatgga     1920
gaacttctgg agggttcagg acagaccgtt gtgccagacg ggaggacgcc tgacatctcc     1980
cacttctacg ttggcgggta taaaaggagt gatatgccaa ccataagcca cgtgacggtg     2040
aataatgttc ttctttacaa ccgacagctg aataccgagg agatcaggac cttgttcttg     2100
agccaggacc ttattggcac ggaagcacac atg                                   2133
```

<210> SEQ ID NO 2
<211> LENGTH: 666
<212> TYPE: PRT
<213> ORGANISM: Trypanosoma cruzi

<400> SEQUENCE: 2

```
Met Gly Lys Thr Val Val Ala Ser Arg Met Phe Trp Leu Met Phe
 1               5                  10                  15

Phe Val Pro Leu Leu Ala Ile Cys Pro Ser Glu Pro Ala Tyr Ala
                20                  25                  30

Leu Ala Pro Gly Ser Ser Arg Val Glu Leu Phe Lys Arg Lys Asn Ser
            35                  40                  45

Thr Val Pro Phe Glu Asp Lys Ala Gly Lys Val Thr Glu Arg Val Val
        50                  55                  60

His Ser Phe Arg Leu Pro Ala Leu Val Asn Val Asp Gly Val Met Val
    65                  70                  75                  80

Ala Ile Ala Asp Ala Arg Tyr Asp Thr Ser Asn Asp Asn Ser Leu Ile
                85                  90                  95

Asp Thr Val Ala Lys Tyr Ser Val Asp Asp Gly Glu Thr Trp Glu Thr
                100                 105                 110

Gln Ile Ala Ile Lys Asn Ser Arg Val Ser Ser Val Ser Arg Val Val
            115                 120                 125

Asp Pro Thr Val Ile Val Lys Gly Asn Lys Leu Tyr Val Leu Val Gly
        130                 135                 140
```

```
Ser Tyr Tyr Ser Ser Arg Ser Tyr Trp Ser Ser His Gly Asp Ala Arg
145                 150                 155                 160

Asp Trp Asp Ile Leu Leu Ala Val Gly Glu Val Thr Lys Ser Thr Ala
            165                 170                 175

Gly Gly Lys Ile Thr Ala Ser Ile Lys Trp Gly Ser Pro Val Ser Leu
            180                 185                 190

Lys Lys Phe Phe Pro Ala Glu Met Glu Gly Met His Thr Asn Gln Phe
        195                 200                 205

Leu Gly Gly Ala Gly Val Ala Ile Val Ala Ser Asn Gly Asn Leu Val
    210                 215                 220

Tyr Pro Val Gln Val Thr Asn Lys Lys Gln Val Phe Ser Lys Ile
225                 230                 235                 240

Phe Tyr Ser Glu Asp Asp Gly Lys Thr Trp Lys Phe Gly Lys Gly Arg
                245                 250                 255

Ser Asp Phe Gly Cys Ser Glu Pro Val Ala Leu Glu Trp Glu Gly Lys
            260                 265                 270

Leu Ile Ile Asn Thr Arg Val Asp Trp Lys Arg Arg Leu Val Tyr Glu
        275                 280                 285

Ser Ser Asp Met Glu Lys Pro Trp Val Glu Ala Val Gly Thr Val Ser
290                 295                 300

Arg Val Trp Gly Pro Ser Pro Lys Ser Asn Gln Pro Gly Ser Gln Ser
305                 310                 315                 320

Ser Phe Thr Ala Val Thr Ile Glu Gly Met Arg Val Met Leu Phe Thr
            325                 330                 335

His Pro Leu Asn Phe Lys Gly Arg Trp Leu Arg Asp Arg Leu Asn Leu
        340                 345                 350

Trp Leu Thr Asp Asn Gln Arg Ile Tyr Asn Val Gly Gln Val Ser Ile
        355                 360                 365

Gly Asp Glu Asn Ser Ala Tyr Ser Ser Val Leu Tyr Lys Asp Lys
370                 375                 380

Leu Tyr Cys Leu His Glu Ile Asn Thr Asp Glu Val Tyr Ser Leu Val
385                 390                 395                 400

Phe Ala Arg Leu Val Gly Glu Leu Arg Ile Ile Lys Ser Val Leu Arg
            405                 410                 415

Ser Trp Lys Asn Trp Asp Ser His Leu Ser Ser Ile Cys Thr Pro Ala
        420                 425                 430

Asp Pro Ala Ala Ser Ser Glu Ser Gly Cys Gly Pro Ala Val Thr
    435                 440                 445

Thr Val Gly Leu Val Gly Phe Leu Ser Gly Asn Ala Ser Gln Asn Val
    450                 455                 460

Trp Glu Asp Ala Tyr Arg Cys Val Asn Ala Ser Thr Ala Asn Ala Glu
465                 470                 475                 480

Arg Val Arg Asn Gly Leu Lys Phe Ala Gly Val Gly Gly Gly Ala Leu
            485                 490                 495

Trp Pro Val Ser Gln Gln Gly Gln Asn Gln Arg Tyr Arg Phe Ala Asn
        500                 505                 510

His Ala Phe Thr Leu Val Ala Ser Val Thr Ile His Glu Ala Pro Arg
        515                 520                 525

Ala Ala Ser Pro Leu Leu Gly Ala Ser Leu Asp Ser Ser Gly Gly Lys
    530                 535                 540

Lys Leu Leu Gly Leu Ser Tyr Asp Glu Lys His Gln Trp Gln Pro Ile
545                 550                 555                 560
```

-continued

```
Tyr Gly Ser Thr Pro Val Thr Pro Thr Gly Ser Trp Glu Thr Gly Lys
            565                 570                 575
Arg Tyr His Leu Val Leu Thr Met Ala Asn Lys Ile Gly Ser Val Tyr
            580                 585                 590
Ile Asp Gly Glu Leu Leu Glu Gly Ser Gly Gln Thr Val Val Pro Asp
            595                 600                 605
Gly Arg Thr Pro Asp Ile Ser His Phe Tyr Val Gly Tyr Lys Arg
            610                 615                 620
Ser Asp Met Pro Thr Ile Ser His Val Thr Val Asn Asn Val Leu Leu
625                 630                 635                 640
Tyr Asn Arg Gln Leu Asn Thr Glu Glu Ile Arg Thr Leu Phe Leu Ser
            645                 650                 655
Gln Asp Leu Ile Gly Thr Glu Ala His Met
            660                 665
```

<210> SEQ ID NO 3
<211> LENGTH: 34
<212> TYPE: DNA
<213> ORGANISM: Artificial Sequence
<220> FEATURE:
<223> OTHER INFORMATION: Synthetic primer

<400> SEQUENCE: 3
ggaattccat atggcacccg gatcgagccg agtt                              34

<210> SEQ ID NO 4
<211> LENGTH: 32
<212> TYPE: DNA
<213> ORGANISM: Artificial Sequence
<220> FEATURE:
<223> OTHER INFORMATION: Synthetic primer

<400> SEQUENCE: 4
ccgctcgagg ctcaagaaca aggtcctgat cg                                32

<210> SEQ ID NO 5
<211> LENGTH: 29
<212> TYPE: DNA
<213> ORGANISM: Artificial Sequence
<220> FEATURE:
<223> OTHER INFORMATION: Synthetic primer

<400> SEQUENCE: 5
gggaattcgg ttgccaatcg cggacgctc                                    29

<210> SEQ ID NO 6
<211> LENGTH: 26
<212> TYPE: DNA
<213> ORGANISM: Artificial Sequence
<220> FEATURE:
<223> OTHER INFORMATION: Synthetic primer

<400> SEQUENCE: 6
cccctcgaga tttgccgtgc ttgcgt                                       26

<210> SEQ ID NO 7
<211> LENGTH: 31
<212> TYPE: DNA
<213> ORGANISM: Artificial Sequence
<220> FEATURE:
<223> OTHER INFORMATION: Synthetic primer

<400> SEQUENCE: 7

```
ccccctcgagc cgacaaaaag ccaacaaaga c                                 31
```

<210> SEQ ID NO 8
<211> LENGTH: 25
<212> TYPE: DNA
<213> ORGANISM: Artificial Sequence
<220> FEATURE:
<223> OTHER INFORMATION: Synthetic primer

<400> SEQUENCE: 8

```
agatgaagac tccgcgcccc tgagg                                         25
```

<210> SEQ ID NO 9
<211> LENGTH: 23
<212> TYPE: DNA
<213> ORGANISM: Artificial Sequence
<220> FEATURE:
<223> OTHER INFORMATION: Synthetic primer

<400> SEQUENCE: 9

```
ccaggtatgc acccagagtg atg                                           23
```

<210> SEQ ID NO 10
<211> LENGTH: 24
<212> TYPE: DNA
<213> ORGANISM: Artificial Sequence
<220> FEATURE:
<223> OTHER INFORMATION: Synthetic primer

<400> SEQUENCE: 10

```
cggagtcaac ggatttggtc gtat                                          24
```

<210> SEQ ID NO 11
<211> LENGTH: 24
<212> TYPE: DNA
<213> ORGANISM: Artificial Sequence
<220> FEATURE:
<223> OTHER INFORMATION: Synthetic primer

<400> SEQUENCE: 11

```
agccttctcc atggtggtga agac                                          24
```

<210> SEQ ID NO 12
<211> LENGTH: 45
<212> TYPE: PRT
<213> ORGANISM: Artificial Sequence
<220> FEATURE:
<223> OTHER INFORMATION: Synthetic peptide

<400> SEQUENCE: 12

Gln Pro Leu Arg Arg Gln Arg Val Val Val Pro Leu Ser Pro Arg
 1               5                  10                  15

Leu Val Leu Leu Ala Phe Cys Arg Gln Arg Leu Pro Leu Lys Arg Met
                20                  25                  30

Gly Gly Ser Tyr Arg Cys Val Asn Ala Ser Thr Ala Asn
                35                  40                  45

<210> SEQ ID NO 13
<211> LENGTH: 21
<212> TYPE: PRT
<213> ORGANISM: Artificial Sequence
<220> FEATURE:
<223> OTHER INFORMATION: Synthetic peptide

<400> SEQUENCE: 13

Arg Gln Arg Leu Pro Lys Arg Met Gly Gly Ser Tyr Arg Cys Val Asn
1               5                   10                  15

Ala Ser Thr Ala His
            20

<210> SEQ ID NO 14
<211> LENGTH: 14
<212> TYPE: PRT
<213> ORGANISM: Artificial Sequence
<220> FEATURE:
<223> OTHER INFORMATION: Synthetic peptide

<400> SEQUENCE: 14

Arg Gln Arg Leu Pro Lys Arg Met Gly Gly Ser Tyr Arg Cys
1               5                   10

<210> SEQ ID NO 15
<211> LENGTH: 21
<212> TYPE: PRT
<213> ORGANISM: Artificial Sequence
<220> FEATURE:
<223> OTHER INFORMATION: Synthetic peptide

<400> SEQUENCE: 15

Gly Asn Ala Ser Gln Asn Val Trp Glu Asp Ala Tyr Arg Cys Val Asn
1               5                   10                  15

Ala Ser Thr Ala Asn
            20

<210> SEQ ID NO 16
<211> LENGTH: 14
<212> TYPE: PRT
<213> ORGANISM: Artificial Sequence
<220> FEATURE:
<223> OTHER INFORMATION: Synthetic peptide

<400> SEQUENCE: 16

Gly Asn Ala Ser Gln Asn Tyr Trp Glu Asp Ala Tyr Arg Cys
1               5                   10

<210> SEQ ID NO 17
<211> LENGTH: 7
<212> TYPE: PRT
<213> ORGANISM: Artificial Sequence
<220> FEATURE:
<223> OTHER INFORMATION: Synthetic peptide

<400> SEQUENCE: 17

Val Asn Ala Ser Thr Ala Asn
1               5

<210> SEQ ID NO 18
<211> LENGTH: 10
<212> TYPE: PRT
<213> ORGANISM: Artificial Sequence
<220> FEATURE:
<223> OTHER INFORMATION: Synthetic peptide

<400> SEQUENCE: 18

Tyr Ser Val Asp Asp Gly Glu Thr Trp Glu
1               5                   10

<210> SEQ ID NO 19
<211> LENGTH: 12
<212> TYPE: PRT
<213> ORGANISM: Artificial Sequence

```
<220> FEATURE:
<223> OTHER INFORMATION: Synthetic peptide

<400> SEQUENCE: 19

Asp Ser Ser Ala His Gly Thr Pro Ser Thr Pro Ala
 1               5                  10

<210> SEQ ID NO 20
<211> LENGTH: 27
<212> TYPE: DNA
<213> ORGANISM: Artificial Sequence
<220> FEATURE:
<223> OTHER INFORMATION: Synthetic primer

<400> SEQUENCE: 20
gcccatggca cccgatcgag ccgagtt                                           27

<210> SEQ ID NO 21
<211> LENGTH: 20
<212> TYPE: DNA
<213> ORGANISM: Artificial Sequence
<220> FEATURE:
<223> OTHER INFORMATION: Synthetic primer

<400> SEQUENCE: 21
cggaattttc atcaccaatg                                                   20

<210> SEQ ID NO 22
<211> LENGTH: 24
<212> TYPE: DNA
<213> ORGANISM: Artificial Sequence
<220> FEATURE:
<223> OTHER INFORMATION: Synthetic primer

<400> SEQUENCE: 22
gttccgaacg gtttgaagtt tgcg                                              24

<210> SEQ ID NO 23
<211> LENGTH: 24
<212> TYPE: DNA
<213> ORGANISM: Artificial Sequence
<220> FEATURE:
<223> OTHER INFORMATION: Synthetic primer

<400> SEQUENCE: 23
gttccgaacg gtttgaagtt tgcg                                              24

<210> SEQ ID NO 24
<211> LENGTH: 23
<212> TYPE: DNA
<213> ORGANISM: Artificial Sequence
<220> FEATURE:
<223> OTHER INFORMATION: Synthetic primer

<400> SEQUENCE: 24
atgaactcct tctccacaag cgc                                               23

<210> SEQ ID NO 25
<211> LENGTH: 22
<212> TYPE: DNA
<213> ORGANISM: Artificial Sequence
<220> FEATURE:
<223> OTHER INFORMATION: Synthetic primer

<400> SEQUENCE: 25
gaagagccct caggctggac tg                                                22
```

<210> SEQ ID NO 26
<211> LENGTH: 24
<212> TYPE: PRT
<213> ORGANISM: Artificial Sequence
<220> FEATURE:
<223> OTHER INFORMATION: Synthetic peptide

<400> SEQUENCE: 26

Asp Ser Ser Ala His Gly Ala Pro Ser Thr Pro Ala Asp Ser Ser Ala
 1               5                  10                  15
His Gly Thr Pro Ser Thr Pro Val
            20

<210> SEQ ID NO 27
<211> LENGTH: 36
<212> TYPE: PRT
<213> ORGANISM: Artificial Sequence
<220> FEATURE:
<223> OTHER INFORMATION: Synthetic peptide

<400> SEQUENCE: 27

Asp Ser Ser Ala His Gly Ala Pro Ser Thr Pro Ala Asp Ser Ser Ala
 1               5                  10                  15
His Gly Thr Pro Ser Thr Pro Val Asp Ser Ser Ala His Gly Thr Pro
            20                  25                  30
Ser Thr Pro Ala
        35

<210> SEQ ID NO 28
<211> LENGTH: 48
<212> TYPE: PRT
<213> ORGANISM: Artificial Sequence
<220> FEATURE:
<223> OTHER INFORMATION: Synthetic peptide

<400> SEQUENCE: 28

Asp Ser Ser Ala His Gly Ala Pro Ser Thr Pro Ala Asp Ser Ser Ala
 1               5                  10                  15
His Gly Thr Pro Ser Thr Pro Val Asp Ser Ser Ala His Gly Thr Pro
            20                  25                  30
Ser Thr Pro Ala Asp Ser Ser Ala His Ser Thr Pro Ser Thr Pro Ala
        35                  40                  45

<210> SEQ ID NO 29
<211> LENGTH: 60
<212> TYPE: PRT
<213> ORGANISM: Artificial Sequence
<220> FEATURE:
<223> OTHER INFORMATION: Synthetic peptide

<400> SEQUENCE: 29

Asp Ser Ser Ala His Gly Ala Pro Ser Thr Pro Ala Asp Ser Ser Ala
 1               5                  10                  15
His Gly Thr Pro Ser Thr Pro Val Asp Ser Ser Ala His Gly Thr Pro
            20                  25                  30
Ser Thr Pro Ala Asp Ser Ser Ala His Ser Thr Pro Ser Thr Pro Ala
        35                  40                  45
Asp Ser Ser Ala His Ser Thr Pro Ser Thr Pro Ala
    50                  55                  60

<210> SEQ ID NO 30

<211> LENGTH: 200
<212> TYPE: PRT
<213> ORGANISM: Trypanosoma cruzi

<400> SEQUENCE: 30

```
Lys Lys Lys Gln Val Phe Ser Lys Ile Phe Tyr Ser Glu Asp Glu Gly
  1               5                  10                  15

Lys Thr Trp Lys Phe Gly Glu Gly Arg Ser Asp Phe Gly Cys Ser Glu
             20                  25                  30

Pro Val Ala Leu Glu Trp Glu Gly Lys Leu Ile Ile Asn Thr Arg Val
             35                  40                  45

Asp Tyr Arg Arg Arg Leu Val Tyr Glu Ser Ser Asp Met Gly Asn Ser
         50                  55                  60

Trp Val Glu Ala Val Gly Thr Leu Ser Arg Val Trp Gly Pro Ser Pro
 65                  70                  75                  80

Lys Ser Asn Gln Pro Gly Ser Gln Ser Ser Phe Thr Ala Val Thr Ile
             85                  90                  95

Glu Gly Met Arg Val Met Leu Phe Thr His Pro Leu Asn Phe Lys Gly
            100                 105                 110

Arg Trp Leu Arg Asp Arg Leu Asn Leu Trp Leu Thr Asp Asn Gln Arg
            115                 120                 125

Ile Tyr Asn Val Gly Gln Val Ser Ile Gly Asp Glu Asn Ser Ala Tyr
        130                 135                 140

Ser Val Leu Tyr Lys Asp Asp Lys Leu Tyr Cys Leu His Glu Ile
145                 150                 155                 160

Asn Ser Asn Glu Val Tyr Ser Leu Val Phe Ala Arg Leu Val Gly Glu
            165                 170                 175

Leu Arg Ile Ile Lys Ser Val Leu Gln Ser Trp Lys Asn Trp Asp Ser
            180                 185                 190

His Leu Ser Ser Ile Cys Thr Pro
            195                 200
```

<210> SEQ ID NO 31
<211> LENGTH: 200
<212> TYPE: PRT
<213> ORGANISM: Trypanosoma cruzi

<400> SEQUENCE: 31

```
Lys Lys Lys Gln Val Phe Ser Lys Ile Phe Tyr Ser Glu Asp Asp Gly
  1               5                  10                  15

Lys Thr Trp Lys Phe Gly Glu Gly Arg Ser Ala Phe Gly Cys Ser Glu
             20                  25                  30

Ala Val Ala Leu Glu Trp Glu Gly Lys Leu Ile Ile Asn Thr Arg Val
             35                  40                  45

Asp Tyr Arg Arg Arg Leu Val Tyr Glu Ser Ser Asp Met Gly Asn Thr
         50                  55                  60

Trp Leu Glu Ala Val Gly Thr Leu Ser Arg Val Trp Gly Pro Ser Pro
 65                  70                  75                  80

Lys Ser Asn Gln Pro Gly Ser Gln Ser Ser Phe Thr Ala Val Thr Ile
             85                  90                  95

Glu Gly Met Arg Val Met Leu Phe Thr His Pro Leu Asn Phe Lys Gly
            100                 105                 110

Arg Trp Leu Arg Asp Arg Leu Asn Leu Trp Leu Thr Asp Asn Gln Arg
            115                 120                 125

Ile Tyr Asn Val Gly Gln Val Ser Ile Gly Asp Glu Asn Ser Ala His
        130                 135                 140
```

```
Ser Ser Val Leu Tyr Lys Asp Asp Lys Leu Tyr Cys Leu His Glu Ile
145                 150                 155                 160

Asn Ser Asn Glu Val Tyr Ser Leu Val Phe Ala Arg Leu Val Gly Glu
            165                 170                 175

Leu Arg Ile Ile Lys Ser Val Leu Gln Ser Trp Lys Asn Trp Asp Ser
            180                 185                 190

His Leu Ser Ser Ile Cys Thr Pro
        195                 200

<210> SEQ ID NO 32
<211> LENGTH: 12
<212> TYPE: PRT
<213> ORGANISM: Artificial Sequence
<220> FEATURE:
<223> OTHER INFORMATION: Synthetic peptide

<400> SEQUENCE: 32

Asp Ser Ser Ala His Gly Ala Pro Ser Thr Pro Ala
1               5                   10

<210> SEQ ID NO 33
<211> LENGTH: 5403
<212> TYPE: DNA
<213> ORGANISM: Trypanosoma cruzi

<400> SEQUENCE: 33
aaagaccgtt ggaagaagaa agaaggttcc ggagcgtggc caccaccaac gatgaactgc      60
cacaattgcg tgctgtccgc gggcggtacc cggcgctttg agcccacggc gacttgtgtg     120 ttccccttt ct cttcccact ttctccgcgg caatccccct gcaaagagac gatcttgaca     180
ccattgtttt aggcataata gaagttctac aaacaacgcc cgaaggacac acaggcaggc     240
accgactacg atggggaaaa cagtcgttgt ggccagtagg atgttctggc taatgttttt     300
cgtgccgctt cttcttgcga tctgccccag cgagcccgcg tacgccctgg cacccggatc     360
gagccgagtt gagggtttaa gcgtaagaat tcgacggtgc cgtttgaaga caaggccggc     420
aaagtcaccg agcgggttgt ccactcgttc cgcttccccg cccttgttaa tgtggacggg     480
gtgatggttg ccatcgcgga cgctcgctac gaaacatcca gtgaaaactc cctcattgat     540
acggtggcga agtacagcgt ggacgatggg gagacgtggg agacccaaat tgccatcaag     600
aacagccgtg tatcgtctgt ttctcgtgtg gtggatccca ccgtgattgt gaagggcaac     660
aagctttacg tcctggttgg aagctactat agttcgagaa gctactggtc gtcgcatggt     720
gatgcgagag actgggatat tctgcttgcc gttggtgagg tcacgaagtc cactgcgggc     780
ggcaagataa ctgcgagtat caaatggggg agccccgtgt cactgaagaa gttttttccg     840
gcagaaatgg aaggcatgca cacaaatcaa tttcttggcg gcgcgggtgt tgccattgta     900
gcgtccaacg ggaatcttgt gtaccctgtg caggttacga acaaaaggaa gcaagttttc     960
tccaagatct tctactcgga agatgatggc aagacgtgga gtttgggaa gggtaggagc    1020 gattttggct gctctgaacc tgtggccctt gagtgggagg ggaagctcat cataaacacc    1080
cgagttgact ggaaacgccg tctggtgtac gagtccagtg acatggagaa accgtgggtg    1140
gaggctgtcg gaaccgtctc gcgtgtgtgg ggccctcac caaaatcgaa ccagcccggc    1200
agtcagacga gcttcactgc cgtgaccatc gaaggaatgc gtgtgatgct cttcacacac    1260
ccgctgaatt taagggaag gtgcgtgcgc gaccgactga acctctggct gacggataac    1320
cagcgcattt ataacgttgg gcaagtatcc attggtgatg aaaattccgc ctacagctcc    1380
```

-continued

```
gtcctgtaca aggatgataa gctgtactgt ttgcatgaga tcaacacgga cgaggtgtac      1440
agccttgttt ttgcacgcct ggttggcgag ctacggatca ttaaatcagt gctgcggtcc      1500
tggaagaatt ggacagccac ctgtccagca tttgcacccc tgctgatcca gccgcttcgt      1560
cgtcagagag tggttgtggt cccgctgtca ccacggttgg tcttgttggc tttttgtcgg      1620
caacgcctcc caaaacgtat gggaggatcg taccgctgcg tcaacgcaag cacggcaaat      1680
gcggagaggg ttcggaacgg tttgaagttt gcggggttg gcggaggagc gctttggccg       1740
gtgagccagc aggggcagaa tcagcggtat cgtttttgcaa accacgcgtt cacgctggtg     1800
gcgtcggtga cgattcacga ggctccgagg gccgcgagtc ccttgctggg tgcgagcctg      1860
gactcttctg gcggcaaaaa actcctgggg ctctcgtacg acgagaagca ccagtggcag      1920
ccaatatacg gatcaacgcc ggtgacgccg acgggatcgt gggagacggg taaaaggtac      1980
cacttggttc ttacgatggc gaataaaatt ggctccgtgt acattgatgg agaacttctg      2040
gagggttcag gacagaccgt tgtgccagac gggaggacgc ctgacatctc ccacttctac      2100
gttggcgggt ataaaggag tgatatgcca accataagcc acgtgacggt gaataatgtt       2160
cttctttaca accgacgaca gctgaatacc gaggagatca ggaccttgtt cttgagccag      2220
gaccttattg gcacggaagc acacatggac agcagcagcg acagcagtgc ccacagtacg      2280
ccctcaactc ccgctgacag cagtgcccac agtacgccct caactcccgt tgacagcagt     2340
gcccacagta cgccctcgac tcccgctgac agcagtgccc acggtacgcc ctcaactccc     2400
gttgacagca gtgcccacgg tacgccctca actcccgctg acagcagtgc ccacggtacg     2460
ccctcaactc ccgttgacag cagtgcccac agtacgccct caactcccgt tgacagcagt     2520
gcccacagta cgccctcaac tcccgttgac agcagtgccc acggtgcgcc ctcaactccc     2580
gctgacagca gtgcccacgg tacgccctcg actccgttg acagcagtgc ccacggtacg      2640
ccctcgactc ccgctgacag cagtgcccac agtacgccct cgactccgc tgacagcagt      2700 gcccacagta cgccctcgac tcccgctgac agcagtgccc acagtacgcc ctcgactccc     2760
gttgacagca gtgcccacgg tacgccctcg actcccgctg acagcagtgc ccacagtacg     2820
ccctcgactc ccgctgacag cagtgcccac ggtacgccct caactcccgt tgacagcagt     2880
gcccacagta cgccctcgac tccgttgac agcagtgccc acggtacgcc ctcaactccc      2940
gttgacagca gtgcccacag tacgccctcg actcccgttg acagcagtgc cacggtacg      3000 ccctcaactc ccgttgacag cagtgcccac agtacgccct cgactccgc tgacagcagt      3060 gcccacagta cgccctcaac tcccgctgac agcagtgccc acgtacgcc ctcaactccc      3120 gttgacagca gtgcccacag tacgccctcg actcccgctg acagcagtgc ccacagtacg     3180
ccctcaactc ccgttgacag cagtgcccac agtacgccct caactcccgc tgacagcagt     3240
gcccacggta cgccctcaac tcccgttgac agcagtgccc acggtacgcc ctcgactccc     3300
gctgacagca gtgcccacag tacgccctcg actcccgctg acagcagtgc ccacagtacg     3360
ccctcgactc ccgctgacag cagtgcccac agtacgccct caactcccgt tgacagcagt     3420
gcccacagta cgccctcaac tcccgctgac agcagtgccc acagtacgcc ctcaactccc     3480
gctgacagca gtgcccacag tacgccctcg actcccgctg acagcagtgc ccacagtacg     3540
ccctcaactc ccgttgacag cagtgcccac agtacgccct caactcccgc tgacagcagt     3600
gcccacggta cgccctcgac tcccgctgac agcagtgccc acagtacgcc ctcgactccc     3660
gttgacagca gtgcccacag tacgccctcg actcccgctg acagcagtgc ccacggtacg     3720
```

-continued

```
ccctcgactc ccgctgacag cagtgcccac agtacgccct cgactcccgc tgacagcagt    3780
gcccacggta cgccctcgac tcccgctgac agcagtgccc acagtacgcc tcaactccc     3840
gctggcagca cgccaatgg tacggttctg attttgcccg atggcgctgc actttcgacc     3900
ttttcggcg gagggcttct tctgtgtgcg tgtgctttgc tgctgcacgt gttttttatg     3960
gcagttttct gatgtagtga gagagtctcc taacaaatgt agataaattc ataattgtgg    4020
tgtgaaccgt ttgggtaaat gtgtgtgtgc gctctcataa ggaaatgatt ccagtaatg     4080
tttttttttt gttctcgaac attttgaata aatctgcaga cagatgggga cgcgtaattt    4140
gaatttgttt ttcagcgttc ttttgtcact ggccccttgt ttaagtggaa ccgcgttgca    4200
atgcggcgag gcatttctc tgttttgatt ccttcttttt ctcctttgt gtttcttcaa      4260
tttgacggtt tgcacgctgt gcggtggagc gttttcccttt gtgaaataag ggccaactgc   4320
ttcacagtgg cacgagggcg ctcaagagat ccgcgggtcg ccagtgactc actttgtgtg    4380
gcgcagctcg aggaggtgtc tggctgctgt gggggcctcg atggttgcca cttcgcgagt    4440
ttgcaacgag cgtgcttctc gcggagggag caggcgaaat attttgtttt tttttttgt    4500
tttttttgtt tttttgtttt tgtgtgtgtg tgtaagtttt ggttcagtct cccttgaact    4560
gggggacgtt gggcttaatg gaccaaactc tgattcccct aaaacttctt tgttggtttt    4620
tcttttgttt ttgttttttgt gctgctgatt tgcacgcttt ctcactgtca ccgaagcgcg   4680
gcggcggtgt ttgagtgccc cctcacgctg ctgctgtgga atttgcgttg cttgcggaca    4740
tttctgttgg gtcgcattgc tttctacttc gttttttatt tttgtggttt ggtggagggg    4800
agtgtgcagc aggggcggg ccgagatgcc tgtggagaca gcgacgttgc ggggactctc     4860
tctcggcctc gtcattcaac aatccattgc gcagcaggtt gccacgaaca ccagcaccaa    4920
tatttgttcg ttttcccact attaccggcg cgtctagccg cacgatgcca tctgggtgcc    4980
gaggaggcgg ttgagcagcg gaaaaggctt cctgctatga agcgactgcc attgagagaa    5040
cttttagctg cgtggatctt cctcaatgcc cagccgttgg cgcgcagcgg aggtgcctgg    5100
gcattctagg agcagatggc gaaaggtttc ctgcgcgtca actggcgtgt ctgtggaggt    5160
tggctatcct cagtcgggag accgcctcct ggcaccacag aacgggtagc ggtagtgtct    5220
tggcgaatag tacaacgcca cttgttgctg actgggcagt aaagcatgtc agcgggtccg    5280
tgtgccatac gggcgcattc catgttccgt gtgttgtccg gttgccatgg tctgcgtcgc    5340
atgctgagcc gcaggctcgt caacatgcac tccacaatgt ccgtaagaaa actcccggtg    5400
cac                                                                  5403
```

<210> SEQ ID NO 34
<211> LENGTH: 1162
<212> TYPE: PRT
<213> ORGANISM: Trypanosoma cruzi

<400> SEQUENCE: 34

Met Val Ala Ile Ala Asp Ala Arg Tyr Glu Thr Ser Ser Glu Asn Ser
1               5                   10                  15

Leu Ile Asp Thr Val Ala Lys Tyr Ser Val Asp Gly Glu Thr Trp
            20                  25                  30

Glu Thr Gln Ile Ala Ile Lys Asn Ser Arg Val Ser Ser Val Ser Arg
        35                  40                  45

Val Val Asp Pro Thr Val Ile Val Lys Gly Asn Lys Leu Tyr Val Leu
    50                  55                  60

Val Gly Ser Tyr Tyr Ser Ser Arg Ser Tyr Trp Ser Ser His Gly Asp

-continued

```
             65                  70                  75                  80
        Ala Arg Asp Trp Asp Ile Leu Leu Ala Val Gly Glu Val Thr Lys Ser
                        85                  90                  95
        Thr Ala Gly Gly Lys Ile Thr Ala Ser Ile Lys Trp Gly Ser Pro Val
                       100                 105                 110
        Ser Leu Lys Lys Phe Phe Pro Ala Glu Met Glu Gly Met His Thr Asn
                       115                 120                 125
        Gln Phe Leu Gly Gly Ala Gly Val Ala Ile Val Ala Ser Asn Gly Asn
                       130                 135                 140
        Leu Val Tyr Pro Val Gln Val Thr Asn Lys Arg Lys Gln Val Phe Ser
        145                 150                 155                 160
        Lys Ile Phe Tyr Ser Glu Asp Asp Gly Lys Thr Trp Lys Phe Gly Lys
                       165                 170                 175
        Gly Arg Ser Asp Phe Gly Cys Ser Glu Pro Val Ala Leu Glu Trp Glu
                       180                 185                 190
        Gly Lys Leu Ile Ile Asn Thr Arg Val Asp Trp Lys Arg Arg Leu Val
                       195                 200                 205
        Tyr Glu Ser Ser Asp Met Glu Lys Pro Trp Val Glu Ala Val Gly Thr
        210                 215                 220
        Val Ser Arg Val Trp Gly Pro Ser Pro Lys Ser Asn Gln Pro Gly Ser
        225                 230                 235                 240
        Gln Thr Ser Phe Thr Ala Val Thr Ile Glu Gly Met Arg Val Met Leu
                       245                 250                 255
        Phe Thr His Pro Leu Asn Phe Lys Gly Arg Cys Val Arg Asp Arg Leu
                       260                 265                 270
        Asn Leu Trp Leu Thr Asp Asn Gln Arg Ile Tyr Asn Val Gly Gln Val
                       275                 280                 285
        Ser Ile Gly Asp Glu Asn Ser Ala Tyr Ser Ser Val Leu Tyr Lys Asp
                       290                 295                 300
        Asp Lys Leu Tyr Cys Leu His Glu Ile Asn Thr Asp Glu Val Tyr Ser
        305                 310                 315                 320
        Leu Val Phe Ala Arg Leu Val Gly Glu Leu Arg Ile Ile Lys Ser Val
                       325                 330                 335
        Leu Arg Ser Trp Lys Asn Trp Thr Ala Thr Cys Pro Ala Phe Ala Pro
                       340                 345                 350
        Leu Leu Ile Gln Pro Leu Arg Arg Gln Arg Val Val Val Pro Leu
                       355                 360                 365
        Ser Pro Arg Leu Val Leu Leu Ala Phe Cys Arg Gln Arg Leu Pro Lys
                       370                 375                 380
        Arg Met Gly Gly Ser Tyr Arg Cys Val Asn Ala Ser Thr Ala Asn Ala
        385                 390                 395                 400
        Glu Arg Val Arg Asn Gly Leu Lys Phe Ala Gly Val Gly Gly Ala
                       405                 410                 415
        Leu Trp Pro Val Ser Gln Gln Gly Gln Asn Gln Arg Tyr Arg Phe Ala
                       420                 425                 430
        Asn His Ala Phe Thr Leu Val Ala Ser Val Thr Ile His Glu Ala Pro
                       435                 440                 445
        Arg Ala Ala Ser Pro Leu Leu Gly Ala Ser Leu Asp Ser Ser Gly Gly
                       450                 455                 460
        Lys Lys Leu Leu Gly Leu Ser Tyr Asp Glu Lys His Gln Trp Gln Pro
        465                 470                 475                 480
        Ile Tyr Gly Ser Thr Pro Val Pro Thr Gly Ser Trp Glu Thr Gly
                       485                 490                 495
```

-continued

```
Lys Arg Tyr His Leu Val Leu Thr Met Ala Asn Lys Ile Gly Ser Val
            500                 505                 510
Tyr Ile Asp Gly Glu Leu Leu Glu Gly Ser Gly Gln Thr Val Val Pro
            515                 520                 525
Asp Gly Arg Thr Pro Asp Ile Ser His Phe Tyr Val Gly Gly Tyr Lys
            530                 535                 540
Arg Ser Asp Met Pro Thr Ile Ser His Val Thr Val Asn Asn Val Leu
545                 550                 555                 560
Leu Tyr Asn Arg Arg Gln Leu Asn Thr Glu Glu Ile Arg Thr Leu Phe
                565                 570                 575
Leu Ser Gln Asp Leu Ile Gly Thr Glu Ala His Met Asp Ser Ser Ser
                580                 585                 590
Asp Ser Ser Ala His Ser Thr Pro Ser Thr Pro Ala Asp Ser Ser Ala
                595                 600                 605
His Ser Thr Pro Ser Thr Pro Val Asp Ser Ser Ala His Ser Thr Pro
            610                 615                 620
Ser Thr Pro Ala Asp Ser Ser Ala His Gly Thr Pro Ser Thr Pro Val
625                 630                 635                 640
Asp Ser Ser Ala His Gly Thr Pro Ser Thr Pro Ala Asp Ser Ser Ala
                645                 650                 655
His Gly Thr Pro Ser Thr Pro Val Asp Ser Ser Ala His Ser Thr Pro
            660                 665                 670
Ser Thr Pro Val Asp Ser Ser Ala His Ser Thr Pro Ser Thr Pro Val
            675                 680                 685
Asp Ser Ser Ala His Gly Ala Pro Ser Thr Pro Ala Asp Ser Ser Ala
690                 695                 700
His Gly Thr Pro Ser Thr Pro Val Asp Ser Ser Ala His Gly Thr Pro
705                 710                 715                 720
Ser Thr Pro Ala Asp Ser Ser Ala His Ser Thr Pro Ser Thr Pro Ala
                725                 730                 735
Asp Ser Ser Ala His Ser Thr Pro Ser Thr Pro Ala Asp Ser Ser Ala
                740                 745                 750
His Ser Thr Pro Ser Thr Pro Val Asp Ser Ser Ala His Gly Thr Pro
            755                 760                 765
Ser Thr Pro Ala Asp Ser Ser Ala His Ser Thr Pro Ser Thr Pro Ala
            770                 775                 780
Asp Ser Ser Ala His Gly Thr Pro Ser Thr Pro Val Asp Ser Ser Ala
785                 790                 795                 800
His Ser Thr Pro Ser Thr Pro Val Asp Ser Ser Ala His Gly Thr Pro
                805                 810                 815
Ser Thr Pro Val Asp Ser Ser Ala His Ser Thr Pro Ser Thr Pro Val
            820                 825                 830
Asp Ser Ser Ala His Gly Thr Pro Ser Thr Pro Val Asp Ser Ser Ala
            835                 840                 845
His Ser Thr Pro Ser Thr Pro Ala Asp Ser Ser Ala His Ser Thr Pro
            850                 855                 860
Ser Thr Pro Ala Asp Ser Ser Ala His Gly Thr Pro Ser Thr Pro Val
865                 870                 875                 880
Asp Ser Ser Ala His Ser Thr Pro Ser Thr Pro Ala Asp Ser Ser Ala
                885                 890                 895
His Ser Thr Pro Ser Thr Pro Val Asp Ser Ser Ala His Ser Thr Pro
            900                 905                 910
```

-continued

```
Ser Thr Pro Ala Asp Ser Ser Ala His Gly Thr Pro Ser Thr Pro Val
            915                 920                 925

Asp Ser Ser Ala His Gly Thr Pro Ser Thr Pro Ala Asp Ser Ser Ala
        930                 935                 940

His Ser Thr Pro Ser Thr Pro Ala Asp Ser Ser Ala His Ser Thr Pro
945                 950                 955                 960

Ser Thr Pro Ala Asp Ser Ser Ala His Ser Thr Pro Ser Thr Pro Val
            965                 970                 975

Asp Ser Ser Ala His Ser Thr Pro Ser Thr Pro Ala Asp Ser Ser Ala
        980                 985                 990

His Ser Thr Pro Ser Thr Pro Ala Asp Ser Ser Ala His Ser Thr Pro
            995                1000                1005

Ser Thr Pro Ala Asp Ser Ser Ala His Ser Thr Pro Ser Thr Pro Val
           1010                1015                1020

Asp Ser Ala His Ser Thr Pro Ser Thr Pro Ala Asp Ser Ser Ala
1025                1030                1035                1040

His Gly Thr Pro Ser Thr Pro Ala Asp Ser Ser Ala His Ser Thr Pro
                1045                1050                1055

Ser Thr Pro Val Asp Ser Ser Ala His Ser Thr Pro Ser Thr Pro Ala
            1060                1065                1070

Asp Ser Ser Ala His Gly Thr Pro Ser Thr Pro Ala Asp Ser Ser Ala
        1075                1080                1085

His Ser Thr Pro Ser Thr Pro Ala Asp Ser Ser Ala His Gly Thr Pro
    1090                1095                1100

Ser Thr Pro Ala Asp Ser Ser Ala His Ser Thr Pro Ser Thr Pro Ala
1105                1110                1115                1120

Gly Ser Ser Ala Asn Gly Thr Val Leu Ile Leu Pro Asp Gly Ala Ala
            1125                1130                1135

Leu Ser Thr Phe Ser Gly Gly Gly Leu Leu Leu Cys Ala Cys Ala Leu
            1140                1145                1150

Leu Leu His Val Phe Phe Met Ala Val Phe
            1155                1160
```

T. CRUZI-DERIVED NEUROTROPHIC AGENTS AND METHODS OF USE THEREFOR

RELATED APPLICATION

This application claims the benefit of U.S. Provisional Application No. 60/172,881, filed on Dec. 20, 1999, the entire teachings of which are incorporated herein by reference.

GOVERNMENT SUPPORT

The invention was supported, in whole or in part, by grants RO1 AI24837 and AI40574 from the National Institutes of Health. The Government has certain rights in the invention.

BACKGROUND OF THE INVENTION

Neuronal degeneration and death normally occur during development and result in the elimination of cells which fail to make crucial inter-neural or neuro-muscular contacts. Neuronal degeneration and death also occur during senescence and as a result of pathological events (e.g., infections, acute trauma) and some genetic diseases (e.g., Huntington's disease).

Neurotrophic factors are a group of proteins that can regulate the survival, development, differentiaiton and many of the functions of neuronal cells. Several neurotrophic factors have been described including members of the NGF-family of neurotrophins, such as nerve growth factor (NGF), brain-derived neurotrophic factor (BNGF), neurotrophin-3 (NT-3) and neurotrophin-4 (NT-4), and members of the IL-6 family, including interleukin-6 (IL-6), interleukin-11 (IL-11), leukemia inhibitory factor (LIF), cilliary neurotrophic factor (CNTF) and oncostatin-M (OSM). The discovery of neurotrophic factors lead to the possibility that these factors could be administered to mammals as therapeutic agents to treat or prevent neuronal degeneration. However, the proteins which have been identified as neurotrophic factors generally mediate multiple biological functions (e.g., immune regulation, hematopoiesis). Thus, the ability to safely administer neurotrophic factors to mammals is severely limited due to undesirable side effects. For example, the administration of CNTF can result in muscle atrophy, cachexia and anorexia (Martin, D., et al., *Am. J. Physiol.* 271: 1422–1428 (1996)).

One example of an infectious disease which leads to neuronal degeneration is Chagas' disease, which is produced by the obligate intracellular protozoan *Tyrpanosoma cruzi*. This disease is an important cause of cardiac and gastrointestinal (GI) morbidity and mortality in millions of people in Latin America. The disease is usually transmitted to man by infected reduviid bugs or by blood transfusion. For a few months parasites circulate in the bloodstream as a result of their invasion of, and rapid replication in a variety of cell types, particularly muscle cells in the heart and GI tract, and glial cells in the nervous system (acute infection). Most patients survive the acute infection to enter a subclinical, asymptomatic stage that lasts years to decades (the indeterminate phase). The vast majority of patients in the indeterminate phase (~90%) show no signs of peripheral neuropathy (Genovese, O., et al., *Arq. Neuropsiquiatr* 54: 190–196 (1996)). In fact, the average numbers of both cardiac and GI ganglia actually increase with the age of the chagasic patient (Köberle, F. *Adv. Parasitol.* 6: 63–71 (1968)).

The relative increase in the number of neuronal cells observed in infected individuals is dramatically different from the age-related physiological reduction in the number of cells found in ganglia of normal uninfected individuals (Köberle, F. *Adv. Parasitol.* 6: 63–71 (1968); Meciano Filho, J. *Gerantology* 41. 18–21 (1995)). The neuroprotective/neuroproliferative effect of *T. cruzi* infection in humans, is consistent with histological and electrophysiological findings in laboratory animals infected with the trypanosome. For example, infected mice showed signs of neuron development, axon regeneration and axon sprouts, in addition to some neuron degeneration. Furthermore, studies with rats infected with *T. cruzi* provide pharmacological evidence for axonal regrowth and sprouting in sympathetic and parasympathetic nerve fibers of the heart and colon (Machado, C. R., et al., *Am. J, Trop. Med. Hyg.* 27: 20–24 (1978); Machado, C. R., et al., *Braz. J. Med. Biol. Res.* 20: 697–702 (1987)).

In contrast to indeterminate phase, extensive destruction of the autonomous nervous system in the heart and GI tract occurs in individuals with chronic Chagas' disease. Histologically, the neurons in the heart are shrunk and disintegrated, with or without perineural and intraneural inflammation. This neurological pathology likely contributes to the generation of cardiomegaly (Mott, K. E. and Hagstrom, J. W. C., *Cicrulcation* 31: 273–286 (1965); Oliveira, J. S. M., et al., *Am. Heart J.* 109: 304–308 (1985)). In the GI tract, myenteric (Auerbach's) and submucosal (Meissner's) ganglia can be more than 95% destroyed (Köberle, F. *Adv. Parasitol.* 6: 63–71 (1968)). This neuronal destruction provides one explanation for the tremendous enlargement of the esophagus and colon (megaesophagus and megacolon) of chronic Chagas' disease (Köberle, F. *In Ciba Foundation Symposium* 20: 137–147 (1974)).

The biochemical pathways that rescue neurons from death in the indeterminate phase are unknown, as are the pathways that drive neurons to die in the chronic disease. An intriguing possibility is that *T. cruzi* secretes a factor(s) that promote(s) development and survival of neurons. Such a factor(s) could help neurons counterbalance neurotoxic insults resulting from the infection process.

A need exists for a method of providing neurotrophic support in a mammal, and for neurotropic factors which significantly reduce or eliminate the above-mentioned problems.

SUMMARY OF THE INVENTION

The invention relates to *T. cruzi* trans-sialidase (TS) and to the neurotrophic and IL-6 secretion-inducing activities of the protein. In one aspect, the invention relates to a method of providing trophic support for neurons and/or glial cells (e.g., Schwann cells) in a mammal (e.g., a human, *Homo sapiens*), comprising administering to the mammal a therapeutically effective amount of TS or a neurotrophic varient thereof. In one embodiment, a synergistic amount of a mammalian neurotrophic factor, such as ciliary neurotrophic factor (CNTF) or leukemia inhibitory factor (LIF), is co-administered with TS or a neurotrophic varient thereof The neurotrophic variant can comprise the amino acid sequence of peptide C44 (SEQ ID NO:12) or of peptide C14 (SEQ ID NO:14). The neurotrophic variant can also be a fusion protein comprising TS or a neurotrophic variant thereof as a first moiety and a suitable fusion partner as a second moiety. In one embodiment, the fusion protein comprises a fusion partner which is a mammalian (e.g., human) neurotrophic factor. In an additional embodiment, TS or a neurotrophic varient thereof is administered to a mammal having a condition selected from the group consisting of amyotrophic lateral sclerosis, Alzheimer's disease, Parkinson's disease, Huntington's disease, Chagas' disease, peripheral neuropathy, palsies (e.g., cerebral, facial, Bell's, bulbar, gaze, oculomotor, progressive supranuclear, trochler), multiple sclerosis, stroke, brain trauma, spinal cord trauma and peripheral nerve trauma.

In another embodiment, the invention is a method of providing trophic support for neurons and/or glial cells in a mammal (e.g., a human), comprising administering to the mammal a therapeutically effective amount of a peptide comprising the amino acid sequence of peptide C14 (SEQ ID NO:14) or a neurotrophic varient thereof. In one embodiment, the peptide further comprises an amino-protecting group, a carboxyl-protecting group or a combination thereof. In another embodiment, the peptide is co-administered with a synergistic amount of a mammalian neurotrophic factor, such as CNTF or LIF.

In another aspect, the invention relates to a method of inducing the secretion of IL-6 in a mammal (e.g., a human), comprising administering to the mammal a therapeutically effective amount of TS or an IL-6 secretion-inducing variant thereof. In one embodiment, the variant comprises an amino acid sequence in which the amino acid sequence of peptide TR1 (SEQ ID NO:32) occurs at least twice. In another embodiment, the variant is a fusion protein, comprising TS or an IL-6 secretion-inducing variant thereof as a first moiety and a suitable fusion partner as a second moiety.

In another embodiment, the invention is a method of inducing the secretion of IL-6 in a mammal (e.g., a human), comprising administering to the mammal a therapeutically effective amount of a peptide comprising an amino acid sequence in which the amino acid sequence of peptide TR1 (SEQ ID NO:32) or an IL-6 secretion-inducing variant thereof occurs at least twice. In an additional embodiment, the peptide further comprises an amino-terminal protecting group, a carboxyl-terminal protecting group or a combination thereof.

In another aspect, the invention is a neurotrophic peptide. In one embodiment, the peptide comprises the amino acid sequence of peptide C14 (SEQ ID NO:14) or a neurotrophic variant thereof. In another embodiment, the invention is a fusion protein comprising the amino acid sequence of peptide C14 (SEQ ID NO:14) or a neurotrophic variant thereof and a suitable fusion partner. The invention also relates to a composition comprising a neurotrophic peptide or neurotrophic fusion protien and a physiologically acceptable carrier. In one embodiment, the composition comprises a peptide comprising the amino acid sequence of peptide C14 (SEQ ID NO:14) or a neurotrophic variant thereof. In another embodiment, the composition comprises a fusion protein comprising the amino acid sequence of peptide C14 (SEQ ID NO:14) or a neurotrophic variant thereof and a suitable fusion partner. In additional embodiments, the composition further comprises a mammalian neurotrophic factor, such as CNTF or LIF.

In another aspect, the invention is an IL-6 secretion-inducing peptide. In one embodiment, the peptide comprises an amino acid sequence in which the amino acid sequence of peptide TR1 (SEQ ID NO:32) or an IL-6 secretion-inducing variant thereof occurs at least twice. In another embodiment, the invention is a fusion protein comprising an amino acid sequence in which the amino acid sequence of peptide TR1 (SEQ ID NO:32) or an IL-6 secretion-inducing variant thereof occurs at least twice, and a suitable fusion partner. The invention also relates to a composition comprising an IL-6 secretion-inducing peptide or an IL-6 secretion-inducing fusion protein and a physiologically acceptable carrier. In one embodiment, the composition comprises a peptide comprising an amino acid sequence in which the amino acid sequence of peptide TR1 (SEQ ID NO:32) or an IL-6 secretion-inducing variant thereof occurs at least twice. In another embodiment, the composition comprises a fusion protein having an amino acid sequence in which the amino acid sequence of peptide TR1 (SEQ ID NO:32) or an IL-6 secretion-inducing variant thereof occurs at least twice, and a suitable fusion partner. In additional embodiments, the composition further comprises a mammalian neurotrophic factor, such as CNTF or LIF.

In an additional embodiment, the invention is a composition comprising TS or a neurotrophic variant thereof, a mammalian neurotrophic factor and a physiologically acceptable carrier.

BRIEF DESCRIPTION OF THE DRAWINGS

FIGS. 1A–B illustrate the nucleotide sequence of the *T. cruzi* trans-sialidase gene, clone 19Y (SEQ ID NO:1) deposited in GenBank under accession number AJ002174, having an open-reading frame beginning at position 370. The entire teachings of each of the information deposited in GenBank under accession number AJ002174 are incorporated herein by reference.

FIG. 1C illustrates the amino acid sequence of the *T. cruzi* trans-sialidase (SEQ ID NO:2) encoded by clone 19Y deposited in GenBank under accession number AJ002174.

7F, recombinant TS from clone 7F; 19Y, recombinant TS from clone 19Y; TS-F, recombinant fragment consisting of amino acid residues 33–666 of TS (SEQ ID NO:2); TS-CC-47, recombinant fragment consisting of amino acid residues 79–478 of TS (SEQ ID NO:2); TS-Cat-47, recombinant fragment consisting of amino acid residues 79–415 of TS (SEQ ID NO:2); BSA, bovine serum albumin.

Figure 3A:
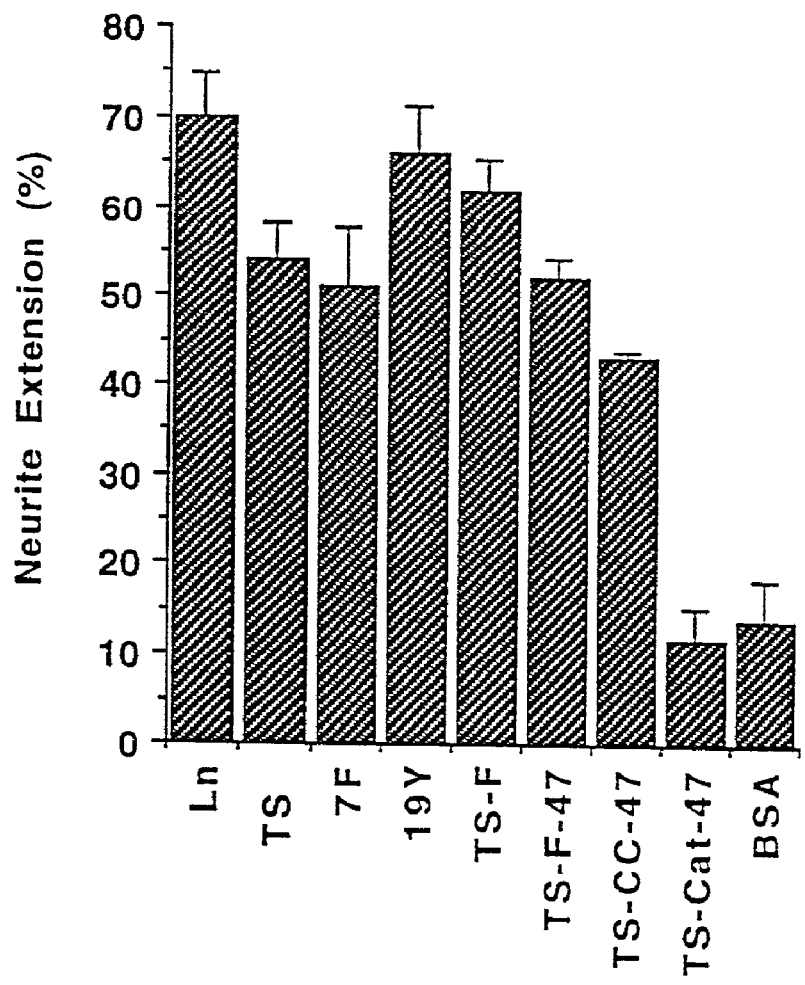
FIG. 3A is a graph showing that neurite outgrowth in N18 cells is induced by immobilized laminin (Ln), immobilized TS and immobilized fragments of TS. Proteins were immobilized by incubating plates which contained wells filled with solutions of the proteins (protein concentration was 500 µg/ml) at 4° C. overnight. The protein solutions were removed and the plates were further incubated with 1% BSA at room temperature for one hour. N18 cells were cultured in the coated wells in serum-free RPMI-1640/0.2% BSA for 17 hours, and neurite outgrowth was measured by phase-contrast microscopy. Cells exhibiting neurite outgrowth were those having one or more cytoplasmic extension >2 µm in length. Ln, laminin; TS, purified *T. cruzi* trans-sialidase.
Figure 3B:
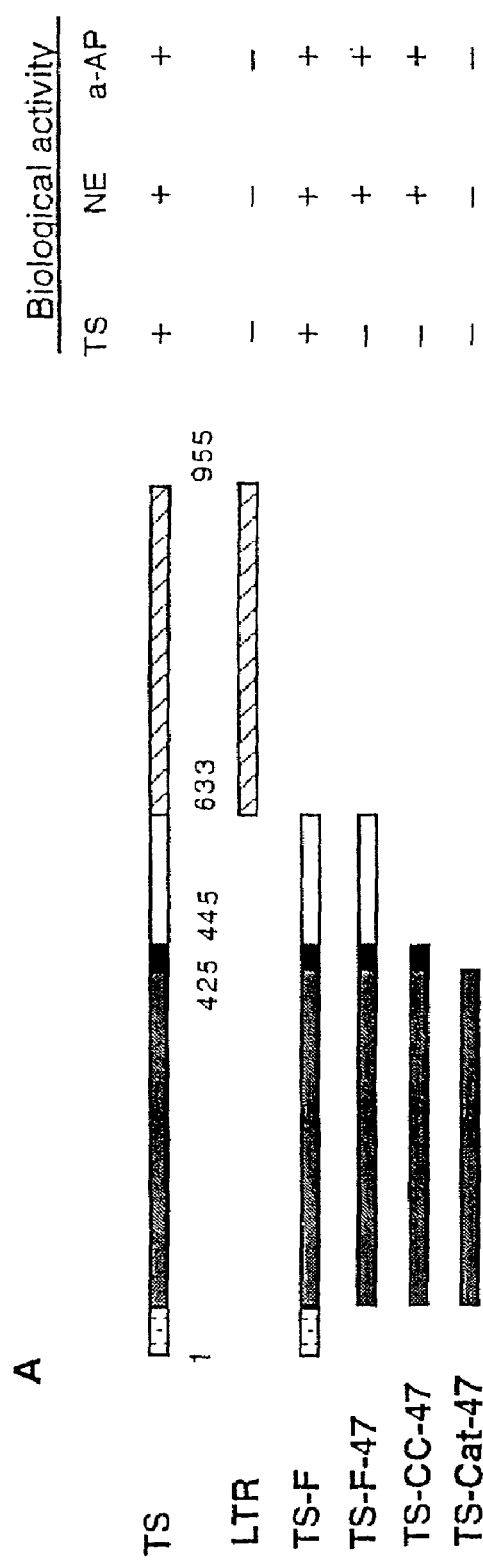

FIG. 3B is a schematic diagram of the linear structure of TS from *T. cruzi* clone 19Y and recombinant fragments thereof. The biological activities indicated on the right of the diagram are: trans-sialidase activity (TS), neurite extension inducing activity (NE) and antiapoptotic activity (a-AP). Numbers under the TS diagram represents amino acid number of TS from clone 19Y (GenBank accession number AJ002174). Trans-sialidase activity, neurite extension activity and antiapoptotic activities were measured at 0.1 µg/ml of purified polypeptides. + indicates that the polypeptide displayed significant dose-dependent extension of neurites or anti-apoptosis activity under the conditions tested. – indicates that the polypeptide was inactive.

Figure 3C:
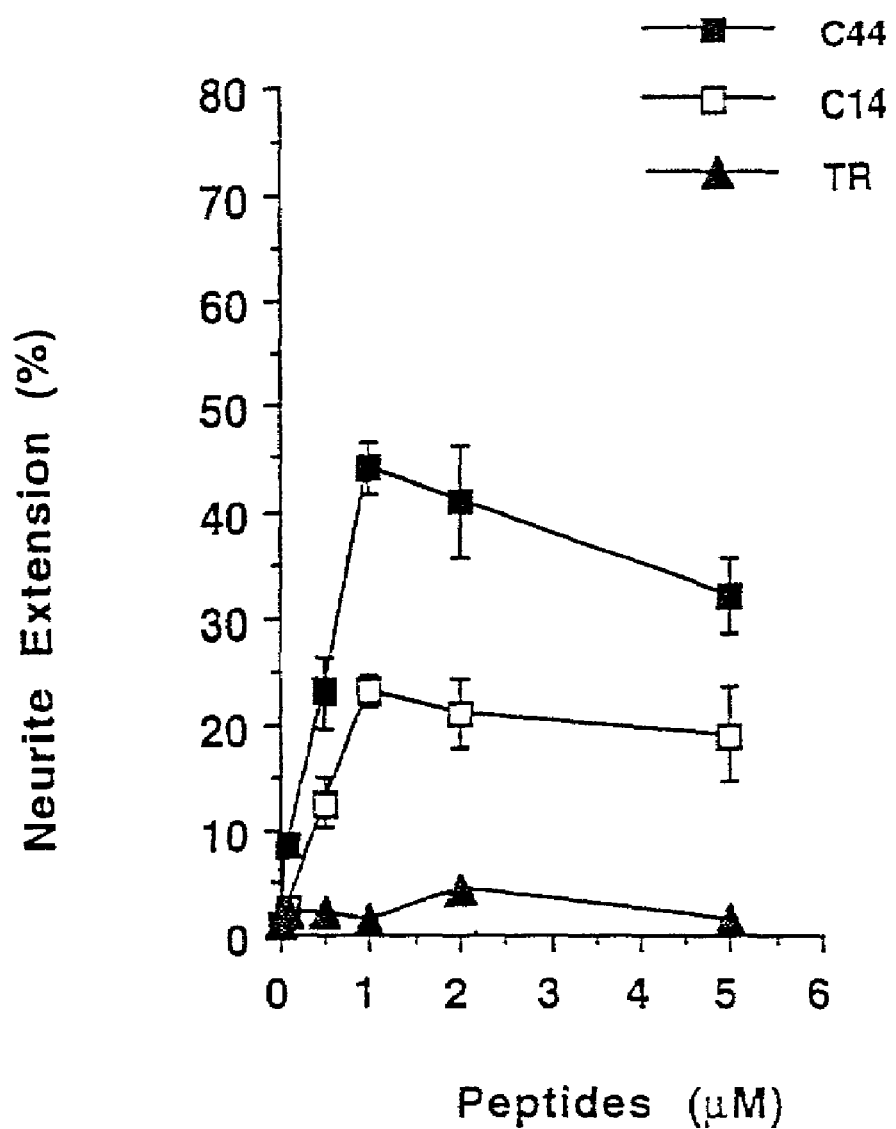

FIG. 3C is a graph showing that synthetic peptide C44 (SEQ ID NO:12) or synthetic peptide C14 (SEQ ID NO:14) induce dose dependent outgrowth of neurites in PC12 cells cultured on collagen coated dishes.

Figure 4A:
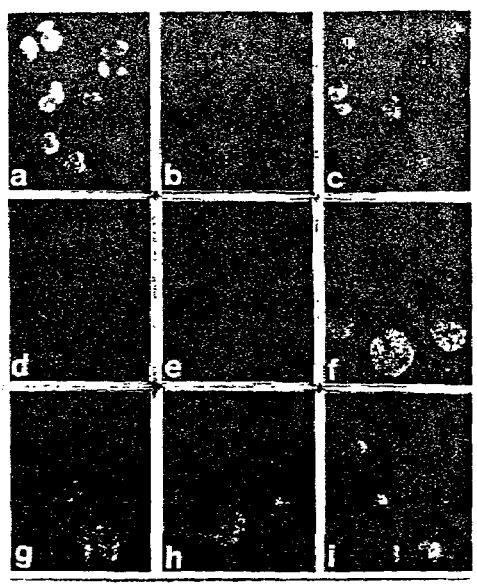
Figure 4B:
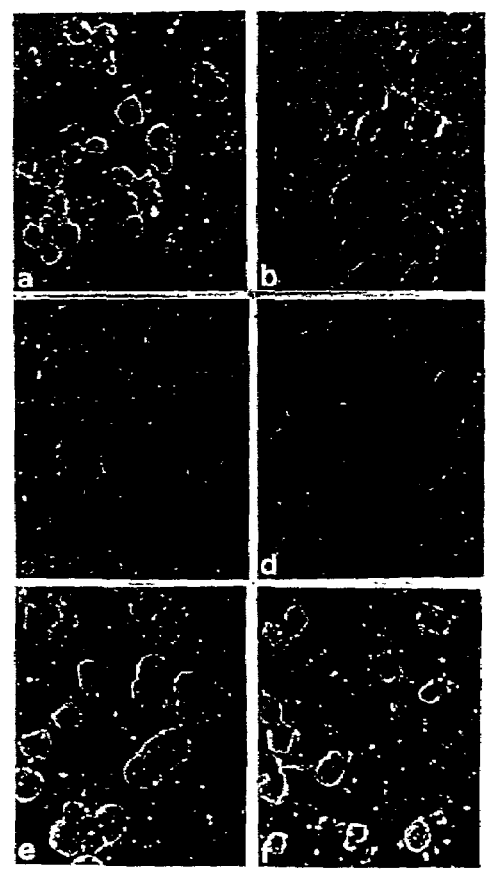

FIGS. 4A and 4B are series of photomicrographs showing that TS inhibits trophic factor withdrawal-induced apoptosis of PC12 cells. PC12 cells were cultured on collagen-coated plastic dishes in serum-free RPM/0.2% BSA supplemented with various reagents for 17 hours. Apoptotic cells were detected by staining with 4,6-diamino-2-phenylindole (DAPI) (FIG. 4A) or by DNA nick end-labeling (TUNEL) (FIG. 4B). The additions in FIG. 4A were: a) no addition; b) 0.1 µg/ml NGF; c) 2.4 µg/ml VCNA; d) 0.1 µg/ml TS; e) 0.1 µg/ml TS-F-47 (amino acid residues 79–666 of SEQ ID NO:34); f) 0.1 µg/ml TS-CC-47; g) 2 µg/ml peptide CF1; h) 2 µg/ml peptide CY1; and i) 0.1 µg/ml TS-Cat-47. Additions in FIG. 4B were: a) no addition; b) 0.1 µg/ml NGF; c) 0.1 µg/ml TS; d) 0.1 µg/ml TS-F-47; e) 0.1 µg/ml TS-CC-47; f) 0.1 µg/ml TS-Cat-47. Magnification, 1000×.

Figure 5A:
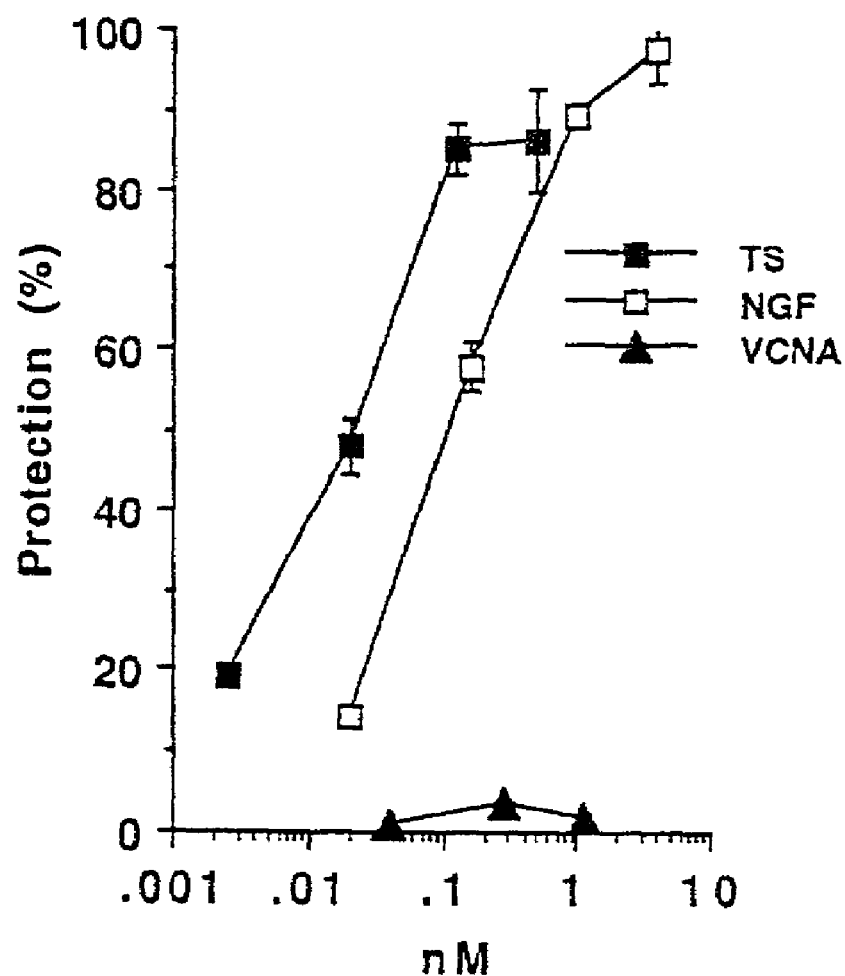

FIG. 5A is a graph showing that TS protects PC12 cells from apoptosis induced by trophic factor withdrawal in a dose dependent manner. PC12 cells were cultured in serum-free RPMI-1640/0.2% BSA or in the same medium supplemented with TS, NGF or VCNA for 17 hours. The molar concentration of TS, NGF and VCNA was based on a MW of 200 kDa for TS, 26 kDa for NGF, and 90 kDa for VCNA. Apoptosis was measured by staining the cells with DAPI.

Figure 5B:
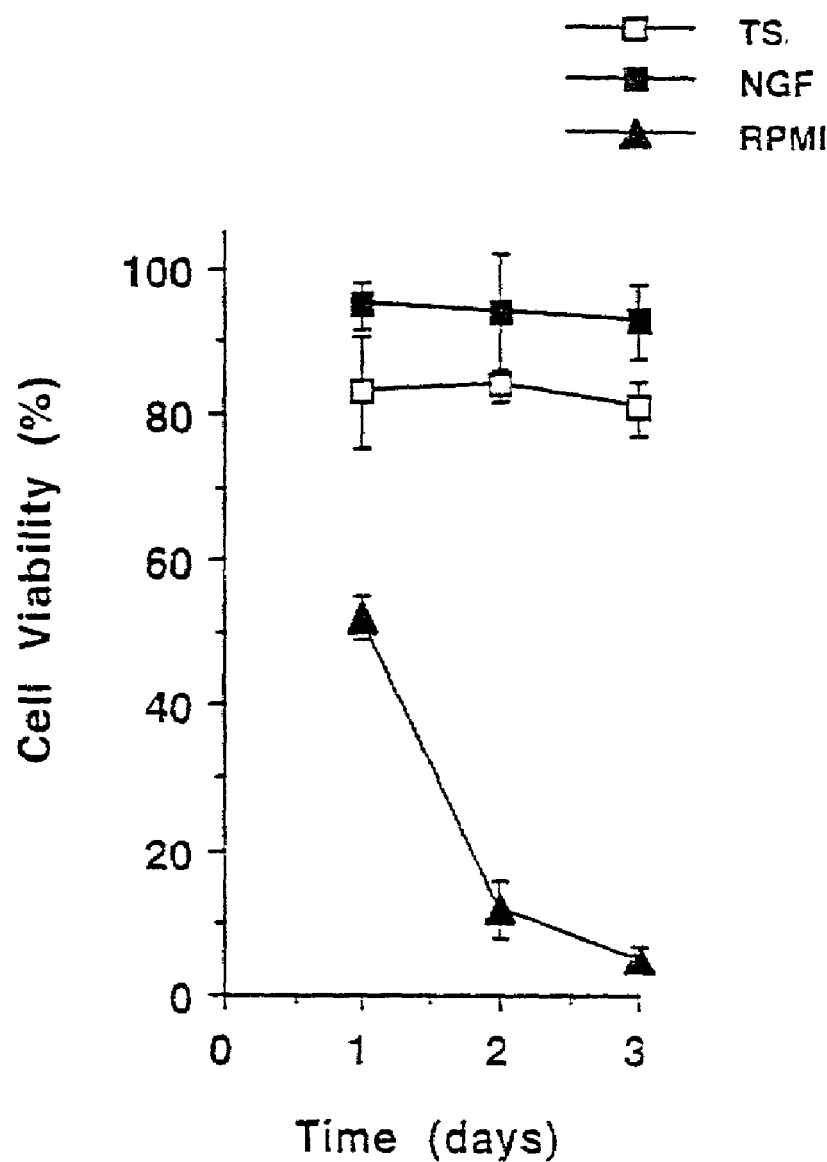

FIG. 5B is a graph showing that TS delayed trophic factor withdrawal-induced apoptotic death of PC12 cells. PC12 cells were cultured in serum-free RPMI-1640/0.2% BSA supplemented with TS (0.5 nM) or NGF (4.0 nM). Cell viability was measured by determining the number of cells without nuclear fragmentation relative to those with nuclear fragmentation by staining with DAPI. 300–400 cells were analyzed in each sample. The presented data are the average of two tests in which each data point represents the average of 3 determinations.

Figure 6A:
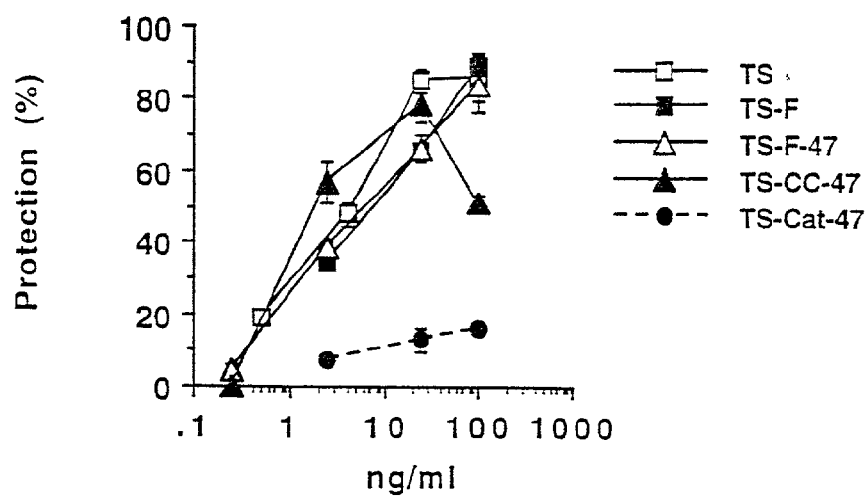

FIG. 6A is a graph showing that TS and certain fragments of TS protected PC12 cells from apoptosis induced by trophic factor withdrawal in a dose dependent manner. PC12 cells were cultured in serum-free RPMI-1640/0.2% BSA in the presence of the indicated concentration of TS or recombinant TS polypeptides for 17 hours. Apoptosis was measured by staining the cells with DAPI.

Figure 6B:
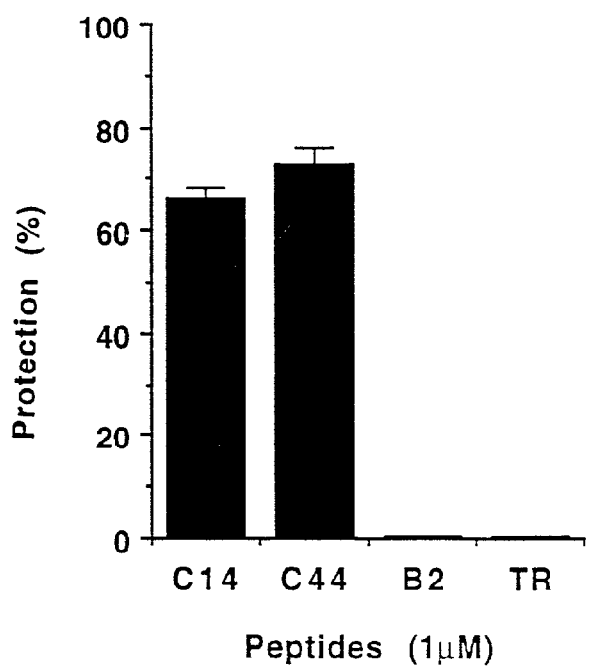

FIG. 6B is a graph showing that synthetic peptides C14 (SEQ ID NO:14) and C44 (SEQ ID NO:12) protected PC12 cells from apoptosis induced by trophic factor withdrawal. PC12 cells were cultured in serum-free RPMI-1640/0.2% BSA supplemented with synthetic peptides (1 µM) for 17 hours. Apoptosis was measured by staining the cells with DAPI. Peptide B2 (SEQ ID NO:18), Peptide TR (SEQ ID NO:19).

Figure 7:
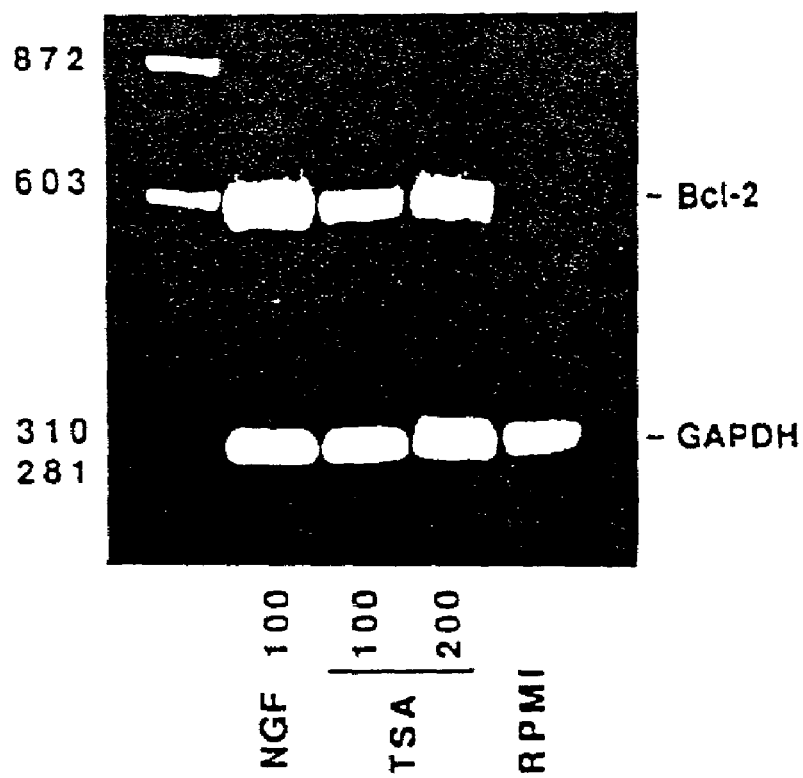

FIG. 7 is a photograph of an ethidium bromide stained electrophoresis gel showing that TS induces the expression of Bcl-2 mRNA in PC12 cells. PC12 cells were cultured for 17 hours in serum-free RPMI-1640/0.2% BSA (RPMI) and in the same medium supplemented with NGF (100 ng/ml) or TS (100 and 200 ng/ml). Gene expression was assessed by RT-PCR analysis of total RNA using primers which specifically amplified Bcl-2 or GAPDH cDNA.

Figure 8A:
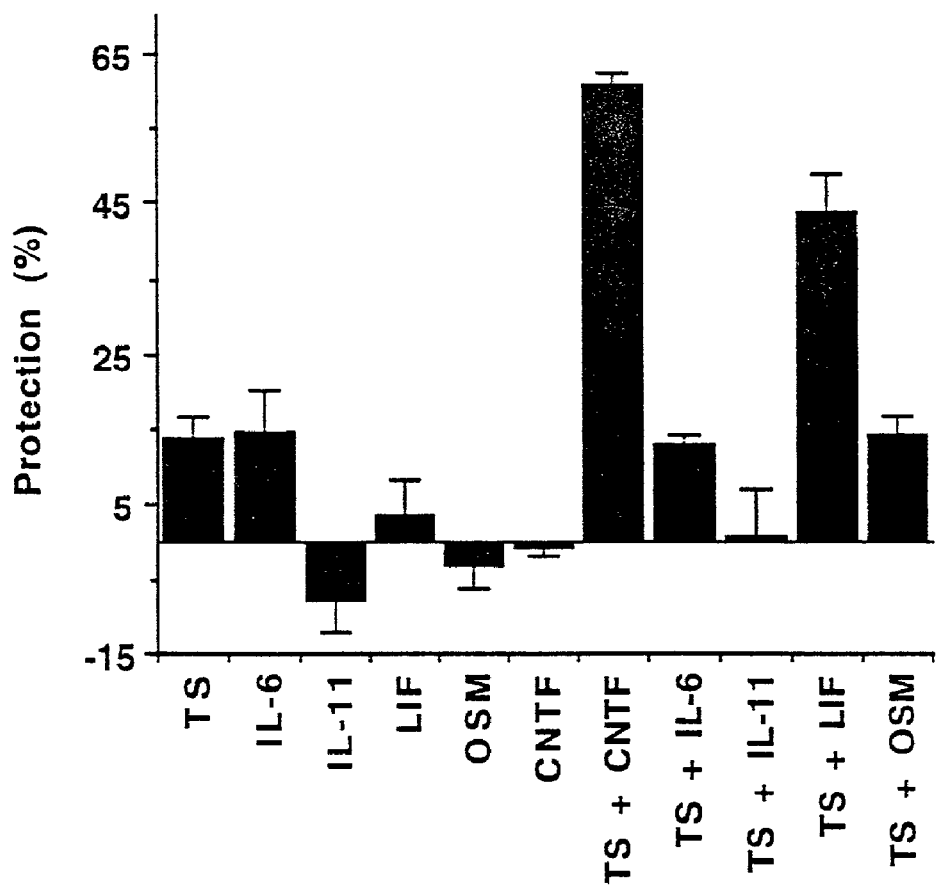

FIG. 8A is a graph showing synergy between TS and CNTF or LIF in protecting PC12 cells from apoptosis induced by trophic factor withdrawal. PC12 cells were cultured for 17 hours in serum-free RPMI-1640/0.2% BSA (negative control, 0% protection), or in the same medium supplemented with the indicated cytokines. TS was used at a concentration of 10 pM (2.5 ng/ml), CNTF was used at 2 nM (50 ng/ml), LIF was used at 1 ng/ml and all other cytokines were used at 5 nM. Apoptosis was measured by DAPI staining.

Figure 8B:
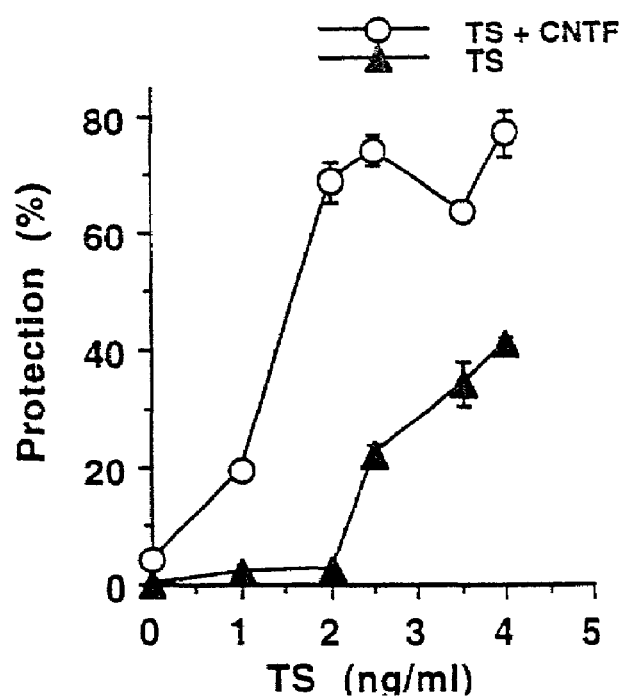

FIG. 8B is a graph showing the dose-response of the synergistic anti-apoptotic action of TS with CNTF. PC12 cells were cultured for 17 hours in serum-free RPMI-1640/ 0.2% BSA (0% protection), in the same medium supplemented with the indicated concentration of TS, or in medium supplemented with 50 ng/ml CNTF and with the indicated concentrations of TS (TS+CNTF). Apoptosis was measured by DAPI staining.

Figure 8C:
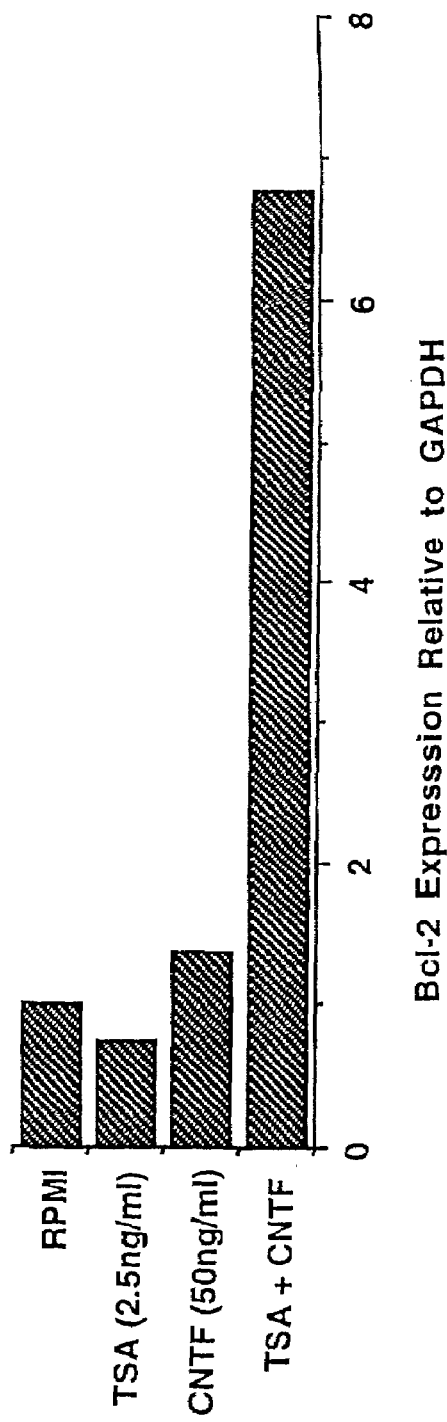

FIG. 8C is a graph showing that quantities of TS and CNTF which did not induce bcl-2 gene expression individually were synergistic, and dramatically induced the expression of bcl-2 mRNA. PC12 cells were cultured in serum-free RPMI-1640/0.2% BSA medium (RPMI) and the same medium supplemented with TS (2.5 ng/ml), CNTF (50 ng/ml) or TS (2.5 ng/ml) +CNTF (50 ng/ml). Total RNA was isolated 17 hours after addition of the growth factors and bcl-2 gene expression was assessed by RT-PCR. The amplified Bcl-2 transcripts in the agarose gels were quantified using a scanning densitometer and normalized to the expression of the GAPDH gene.

Figure 8D:
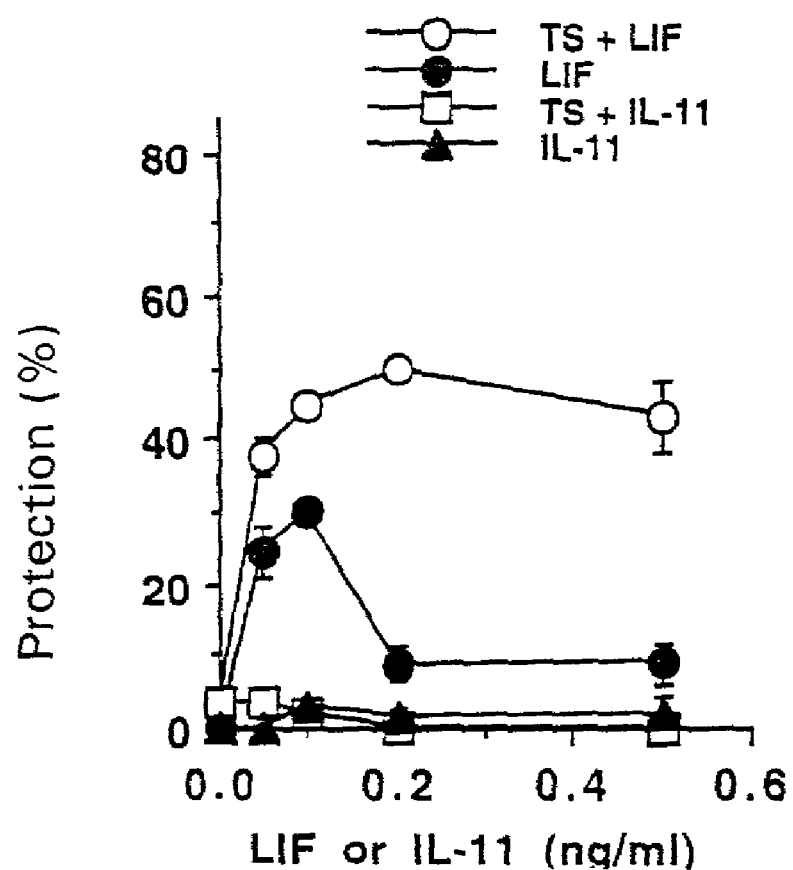

FIG. 8D is a graph illustrating the dose-response relationship of the synergistic anti-apoptotic action of TS with LIF. PC12 cells were cultured for 17 hours in serum-free RPMI-1640/0.2% BSA (0% protection), in the same medium supplemented with 2.5 ng/ml of TS, or in medium supplemented with 2.5 ng/ml of TS which further contained the indicated concentrations of LIF or IL-11 (TS+LIF and TS+IL-11).

Figure 9:
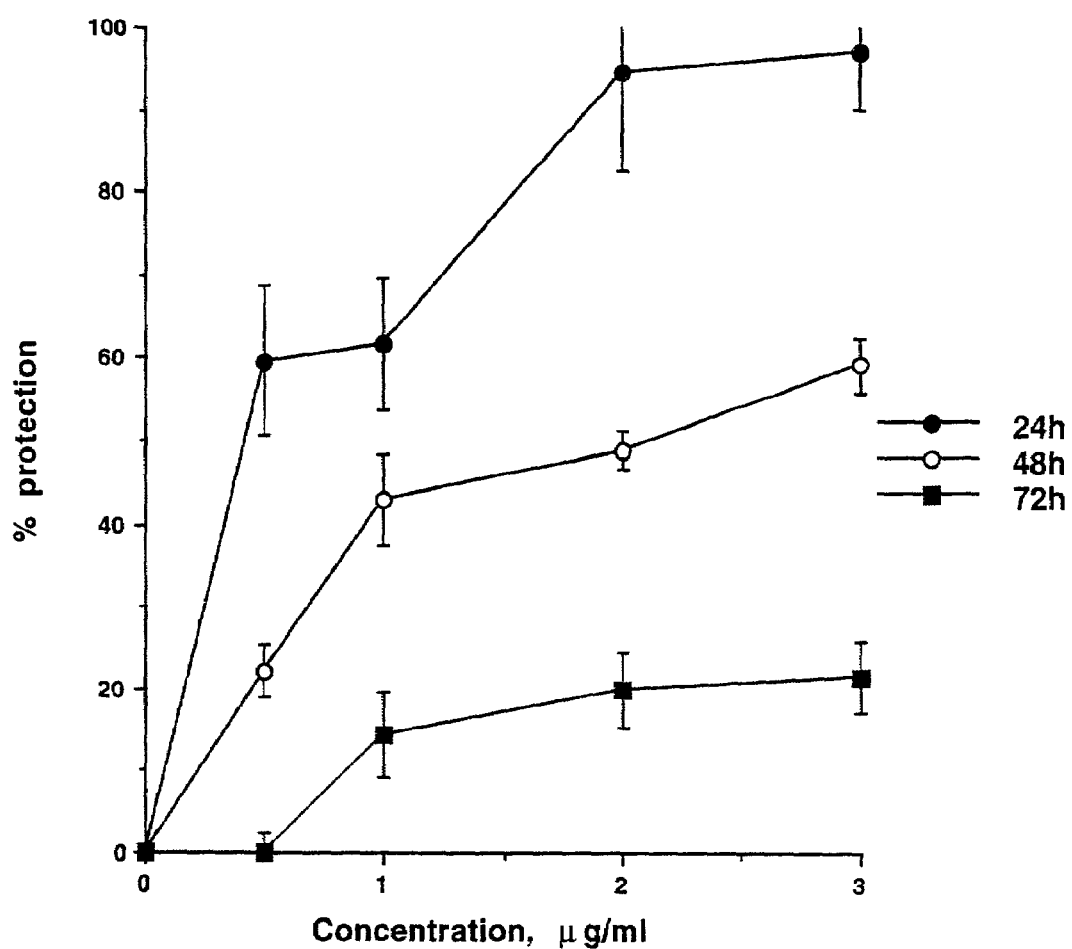

FIG. 9 is a graph showing dose-dependent inhibition of serum withdrawal-induced apoptosis of human Schwann cells by TS. Immortalized Schwann cells (Rambukkana et al., *Science*, 282:2076–2079 (1998)) which had been maintained in DMEM supplemented with 10% fetal calf serum were washed 3 times with serum-free DMEM. The cells were then cultured in serum-free DMEM or in serum-free DMEM containing recombinant TS. After culture for 24, 48 or 72 hours, cells were fixed in 4% formaldehyde in phosphate buffered saline (PBS) for 10 minutes, washed with PBS and stained with DAPI (5 µg/mL) for 2 minutes. Cells with fragmented nuclei (apoptotic cells) were quantified by inspection of 300–400 cells using a fluorescence microscope.

Figures 10A, 10B, 10C, 10D, 10E, 10F, 10G:
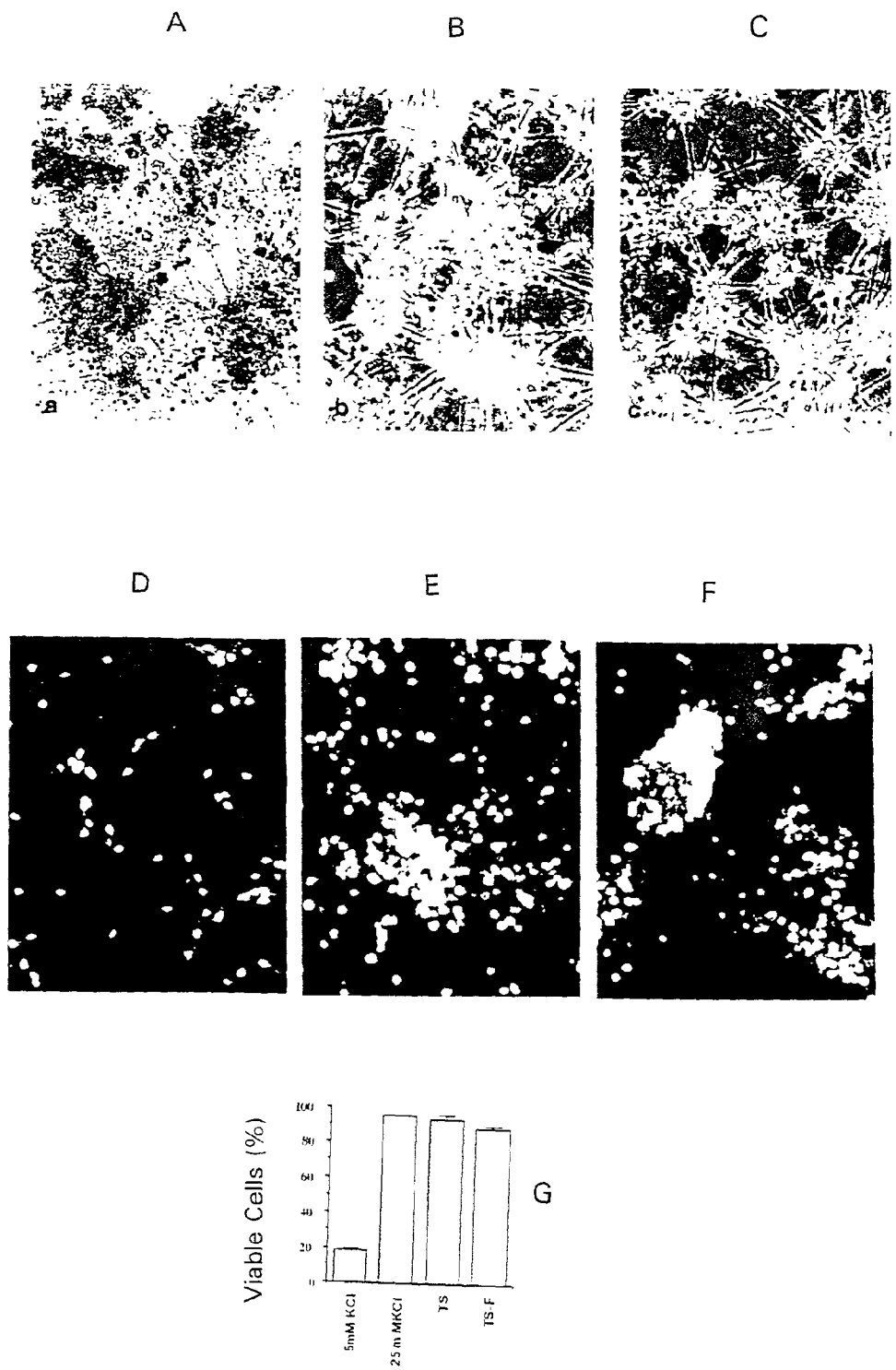

FIGS. 10A–10F are photomicrographs of primary granule neurons. The neurons were maintained in basal Eagle medium (BME) containing high K$^+$ (25 mM KCl) supplemented with 10% FCS (FIGS. 10B and 10E). After 7 days, the medium was changed to serum-free BME containing low K$^+$ (5 mM KCl) (FIGS. 10A and 10D), or to serum-free BME containing low K$^+$ and TS (FIGS. 10C and 10D) and the cells were cultured for a further 24 hours. Then, the cells were stained with fluorescein diacetate (FDA). FIGS. 10A–10C are photomicrographs taken under phase contrast illumination. FIGS. 10D–10F are photomicrographs of cells that were stained with FDA taken under UV illumination. Under these conditions, viable cells are fluorescent. Note the increased number of viable cells in medium containing high K$^+$ or low K$^+$ supplemented with TS (100 ng/ml) (FIGS. 10E and 10F). Original magnification, 400×.

FIG. 10G is a graph which shows the percentage of viable cells found in cultures of granule neurons. Granule neurons were maintained in BME medium containing high K$^+$ (25 mM KCl) supplemented with 10% FCS (FIGS. 10B and 10E) for 7 days. Then the medium was changed to serum-free BME containing low K$^+$ (5 mM KCl), or to serum-free BME containing low K$^+$ and TS (100 ng/ml) or the catalytic domain of TS (TS-F, 100 ng/ml) and the cells were cultured for a further 24 hours. Control cells were cultured for the further 24 hours in high K$^+$ media (25 mM KCl). Viable cells were quantified by staining with FDA and fluorescence microscopy.

Figures 11A, 11B, 11C, 11D:
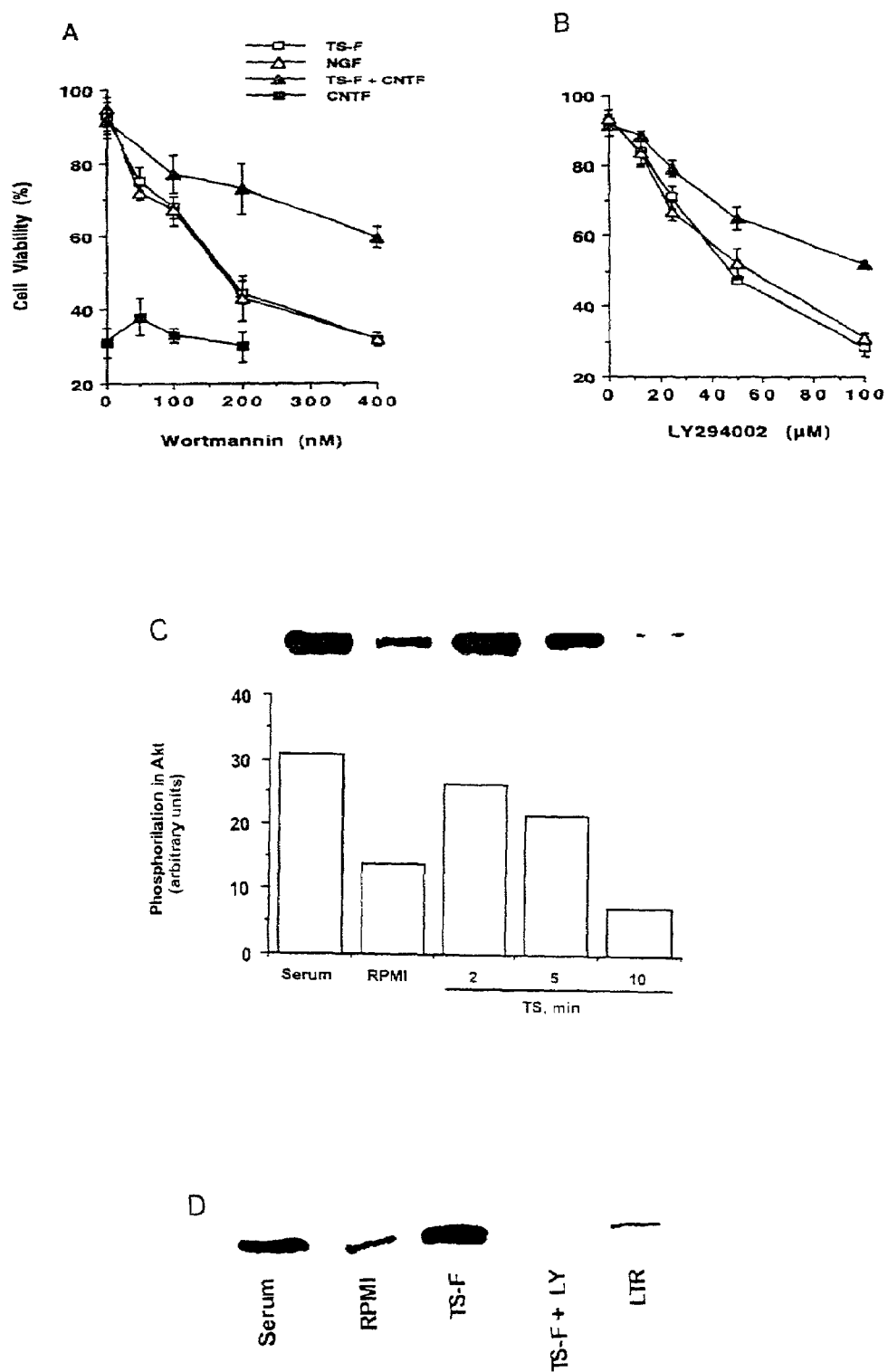

FIGS. 11A and 11B are graphs showing reversal of the survival-promoting activity of TS by wortmannin (FIG. 11A) or LY294002 (LY, FIG. 11B), which are inhibitors of PI-3 kinase. Cultures of PC12 were switched to serum-free RPMI or to serum-free RPMI supplemented with a polypeptide consisting of the catalytic domain of TS (TS-F, 100 ng/ml), NGF (100 ng/ml), CNTF (50 ng/ml) or TS-F (5 ng/ml)+CNTF (50 ng/ml) and cultured for 24 hours. Then, wortmannin or LY was added to the cultures at the indicated concentrations. Neuronal cell viability was measured 24 hours later by staining with DAPI. Viability of PC12 cells cultured in RPMI alone (33%) was similar to the viability of PC12 cells cultured in RPMI+CNTF.

FIG. 11C is a photograph of a Western blot showing that TS induces serine phosphorylation of Akt kinase, and a graph showing the quantities of serine phosphorylated Akt kinase detected in the Western blot. PC12 cells were washed in serum-free RPMI and kept in RPMI containing 0. 1% FCS. After 2 days, the medium was changed to serum free medium for two hours. Then the cells were challenged with 10% FCS (serum), serum free media (RPM1) or TS (100 ng/ml) for 2, 5 or 10 minutes. Cells were lysed in 2% sodium dodecylsulfate (SDS) and proteins in the lysates were resolved by SDS-PAGE through 10% gels. The proteins were transferred to nitrocellulose membranes and probed using an antibody which specifically binds to Akt kinase that is phosphorylated on Ser 473 (phospho-Akt antibody, New England BioLabs, Beverly, Mass.). The bands detected by the antibody were quantified by scanning densitometry.

FIG. 11D is a photograph of a Western blot showing that the PI-3 kinase inhibitor LY294002 (LY) prevents TS-induced serine phosphorylation of Akt kinase in PC12 cells. PC12 cells were washed in serum-free RPMI and kept in RPMI containing 0.1% FCS. After 2 days, the medium was changed to serum free medium for two hours. Then the cells were challenged with 10% FCS (serum), serum free media (RPMI) or TS (100 ng/ml) for 2, 5 or 10 minutes. An additional group of cells were preincubated with LY (1 μM) prior to the addition of the catalytic domain of TS (TS-F, 100 ng/ml). Cells were lysed in 2% sodium dodecylsulfate (SDS) and proteins in the lysates were resolved by SDS-PAGE through 10% gels. The proteins were transferred to nitrocellulose membranes and probed using an antibody which specifically binds to Akt kinase that is phosphorylated on Ser 473 (phospho-Akt antibody, New England BioLabs, Beverly, Mass.). LY completely blocked TS-F-induced phosphorylation of Akt kinase. LY was similarly effective in blocking TS-induced phosphorylation of Akt kinase in PC12 cells.

Figures 12A, 12B, 12C:
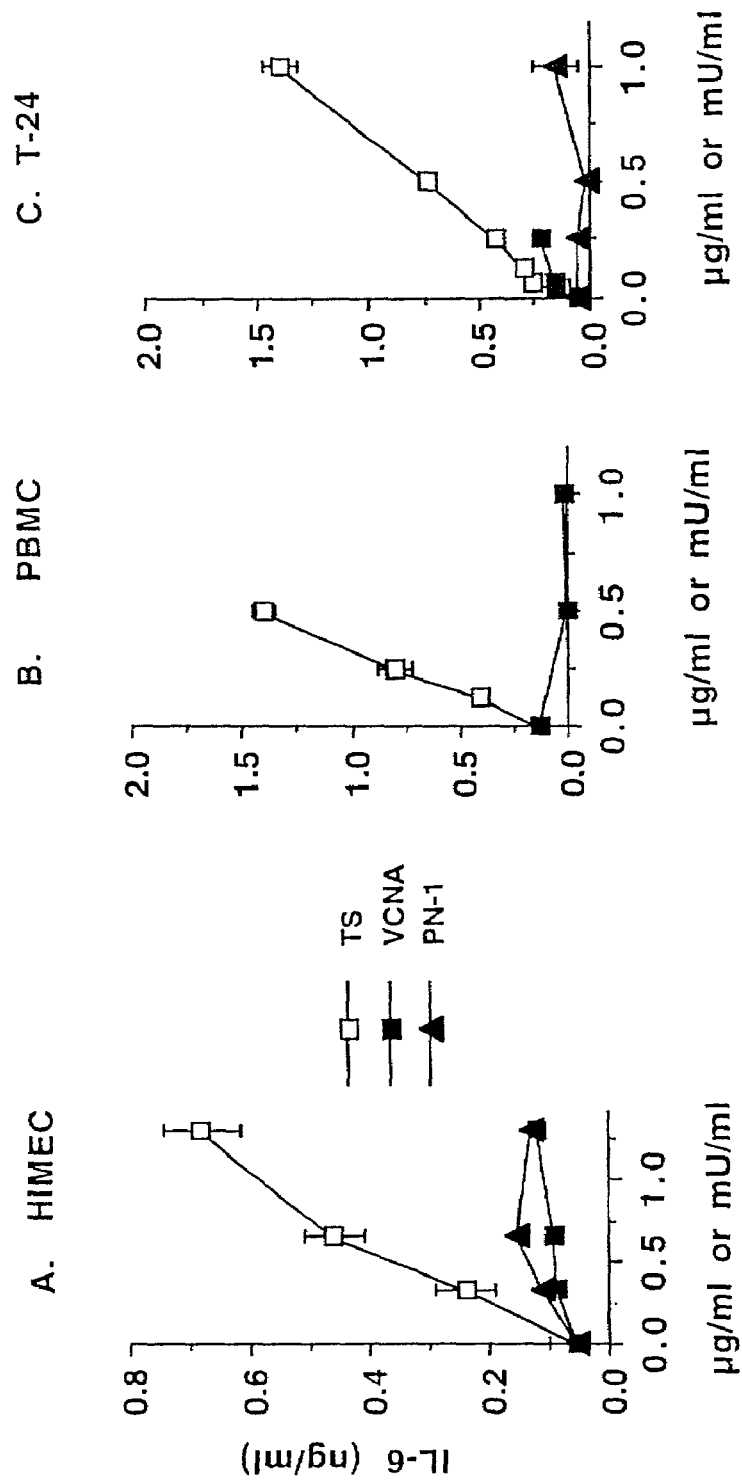

FIGS. 12A–12C are graphs showing dose dependent release of IL-6 by cells stimulated with TS, VCNA and penetrin (PN-1). HIMEC cells (FIG. 12A), PBMC (FIG. 12B) or T-24 carcinoma cells (FIG. 12C) were cultured for 24 hours in media containing various concentrations of TS, VCNA or PN-1. The supernatants of the cultures were then assayed for IL-6 and other cytokines by ELISA. The quantity of TS or PN-1 added to the culture media is expressed as 1 μg/ml, the quantity of VCNA added to the culture media is expressed as mU/ml (the unit corresponded to the neuraminidase activity of TS). The presented data are representative of at least 9 independent studies.

Figures 12D, 12E:
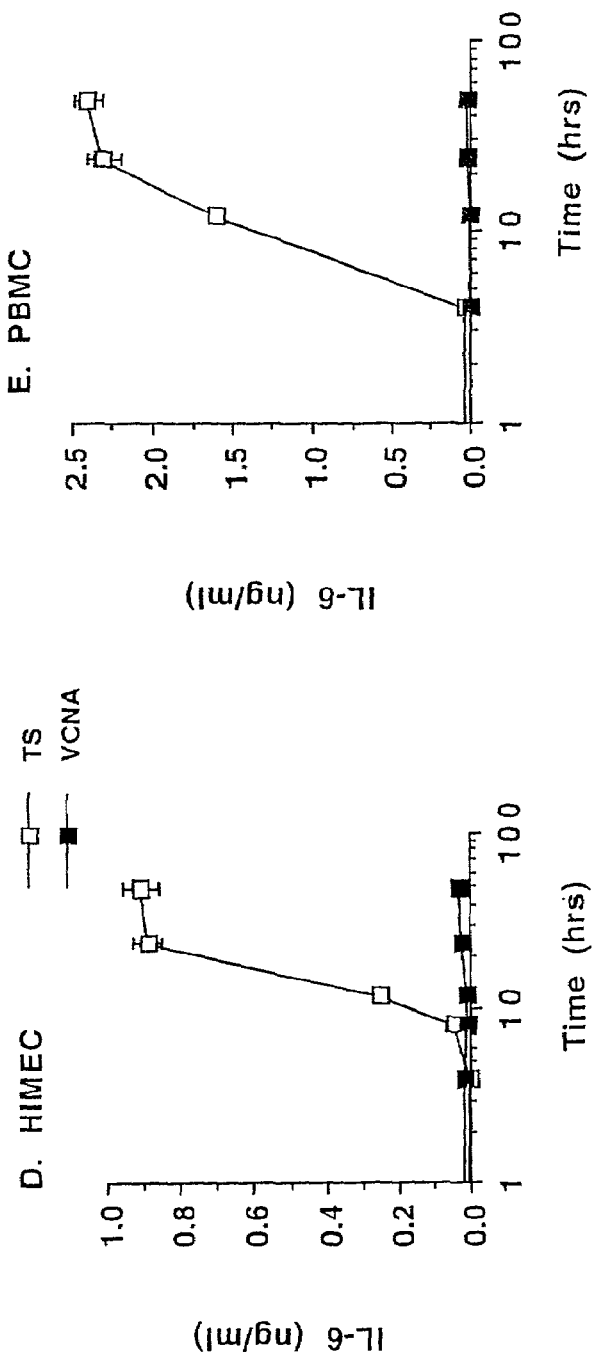

FIGS. 12D and 12E are graphs showing the time course of IL-6 secretion by TS stimulated cells. HIMEC cells (FIG. 12D) or PBMC (FIG. 12B) were cultured in media containing TS (1 μg/ml) or VCNA (1 mU/ml). After culture for predetermined amounts of time, the supernatants of the cultures were assayed for IL-6.

Figures 13A, 13B:
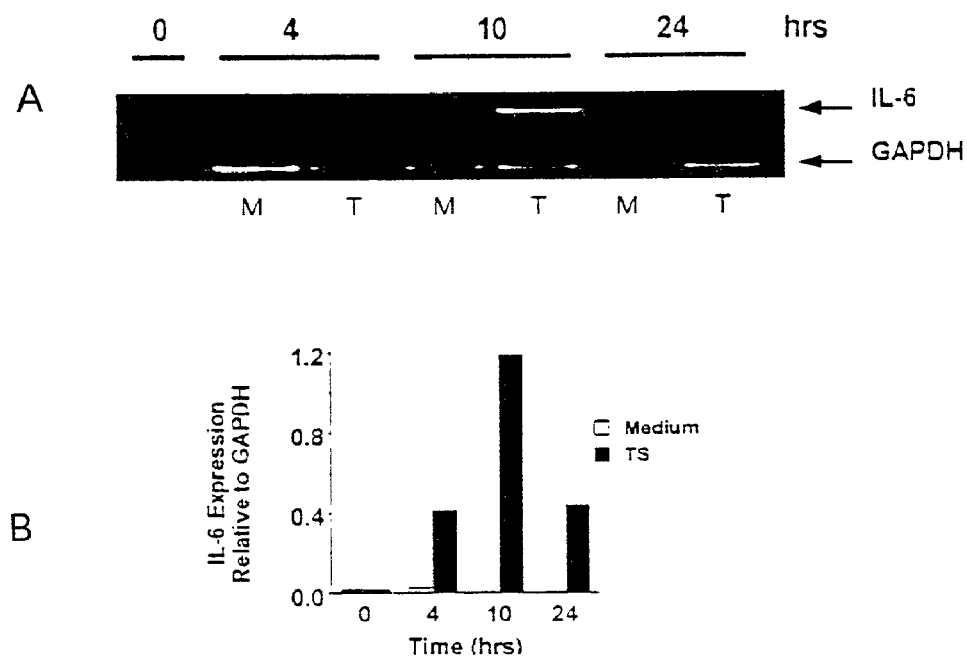

FIGS. 13A is a photograph of an ethidium bromide stained agarose gel showing that TS stimulation induces expression of IL-6 mRNA in PBMC. PBMC were cultured in media (M) or media containing 1 μg/ml of TS (T) for 4, 10 or 24 hours. Gene expression was assessed by RT-PCR analysis of total RNA using primers which specifically amplified IL-6 or GAPDH cDNA.

FIG. 13B is a graph showing that TS stimulation induces expression of IL-6 mRNA in PBMC. Expression of IL-6 mRNA relative to GAPDH mRNA was determined by densitometric measurement of the bands in FIG. 13A.

Figure 14:
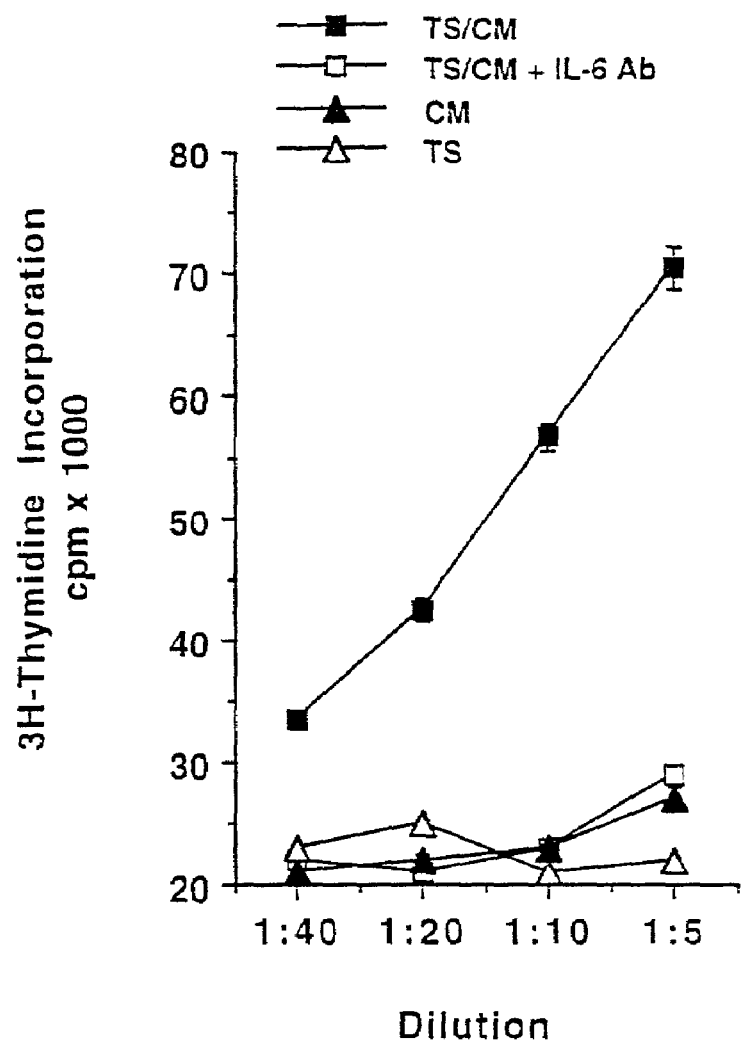

FIG. 14 is a graph showing that TS-conditioned medium restores growth of the IL-6-dependent B-lymphoma, DS-1. PBMC were cultured in media (CM) or in media supplemented with TS (TS/CM) for 24 hours. The conditioned media from these cultures were diluted into IL-6 free media at 1:40, 1:20, 1:10 and 1:5, and DS-1 cells were cultured in the resulting mixture. DS-1 cell proliferation was assessed by measuring the amount of $^3$H-thymidine incorporated into the DNA of cells. TS/CM induced dose dependent proliferation of DS-1 cells. Addition of a neutralizing rabbit anti-IL-6 IgG (1 μg/ml, TS/CM+IL-6 Ab) blocked DS-1 cell proliferation in response to TS/CM, but normal rabbit IgG had no effect on the TS/CM-induced proliferation. IL-6 free media supplemented with 1 μg/ml TS (TS), which corresponds to 1:5 dilution of conditioned media, did not induce proliferation of the DS-1 cells.

Figure 15A:
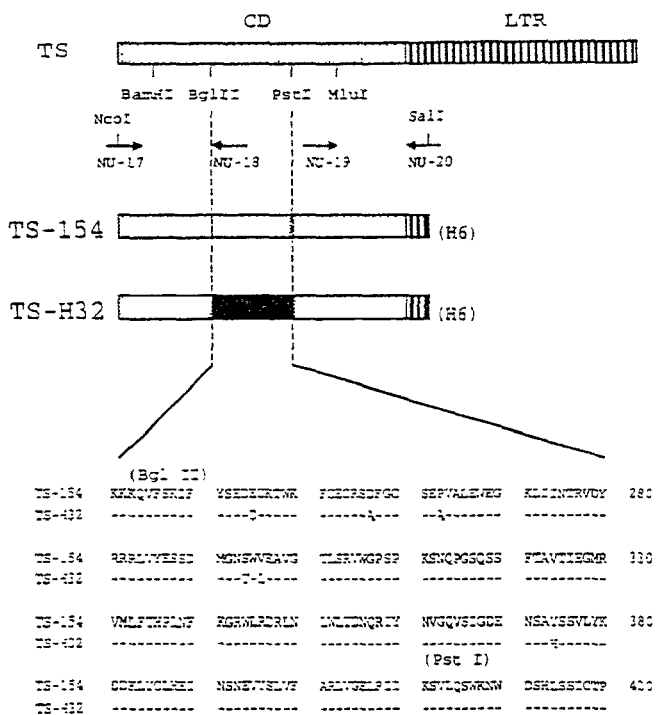

FIG. 15A is a schematic diagram of TS clone 7F and of recombinant fragments TS-154 and TS-H32. NU-17, NU-18, NU-19 and NU-20 are synthetic primers used to make constructs encoding recombinant fragments TS-154 and TS-H32. H6 is a 6× His tag. The amino acid sequences encoded by the Bgl II/Pst I fragments of constructs TS-154 (SEQ ID NO:30) and TS-H32 (SEQ ID NO:31) are presented. The sequences are identical (identical residues indicated by -) except were indicated with the amino acid letter code.

Figure 15B:
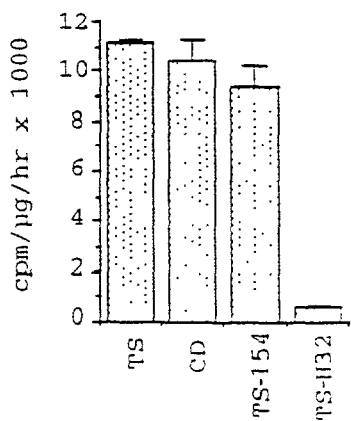

FIG. 15B is a graph showing the catalytic activity of TS, the catalytic domain of TS (CD), and recombinant fragments TS-154 and TS-H32.

Figure 15C:
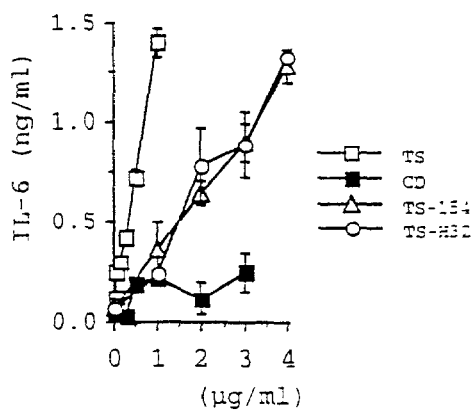

FIG. 15C is a graph showing the IL-6 secretion inducing activity of TS, the catalytic domain of TS (CD), and recombinant fragments TS-154 and TS-H32. The IL-6 secretion inducing activity of the polypeptides was assessed in cultures of PBMC. Similar activity was detected in cultures of T-24 cells.

Figures 16A, 16B:
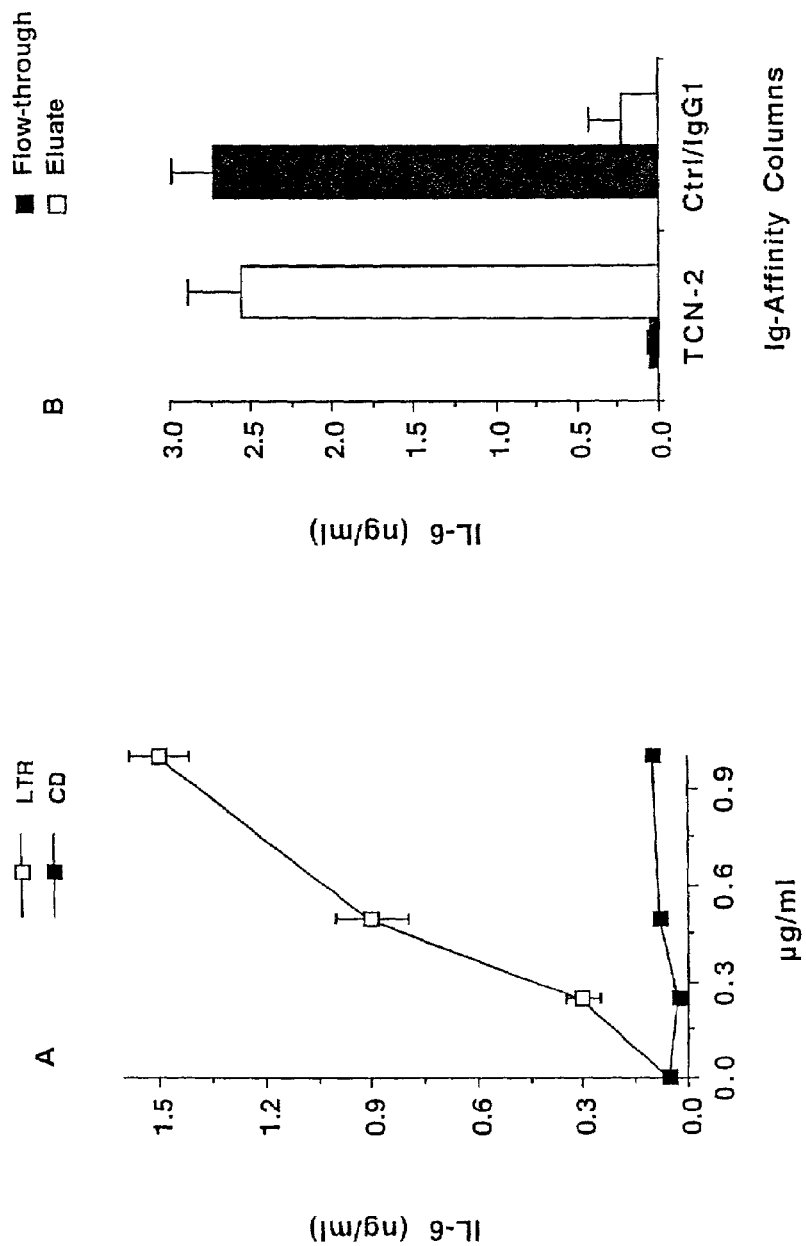

FIG. 16A is a graph showing dose dependent secretion of IL-6 by T-24 cells stimulated with recombinant tandem repeat domain (LTR) of TS. T-24 cells were cultured for 24 hours in media or in media containing LTR or the catalytic domain of TS (CD). IL-6 secreted into the culture media was assessed by ELISA. Similar results were obtained in studies using PBMC.

FIG. 16B is a graph showing that immunodepletion of LTR removes IL-6 secretion-inducing activity. An LTR solution was passed through a protein G-Sepharose column adsorbed with either anti-LTR mAb TCN-2 (TCN-2) or a control anti-p-azo-phenylarsonate IgG1 (Ctrl/IgG1). The flow-through of each column was added to cultures of T-24 cells. The cells were cultured for 24 hours and the culture media was assayed for IL-6 by ELISA. Eluates from each column were obtained by mechanical stirring of the agarose followed by centrifugation and tested for IL-6 secretion inducing activity in the same way as the flow-throughs.

Figure 17:
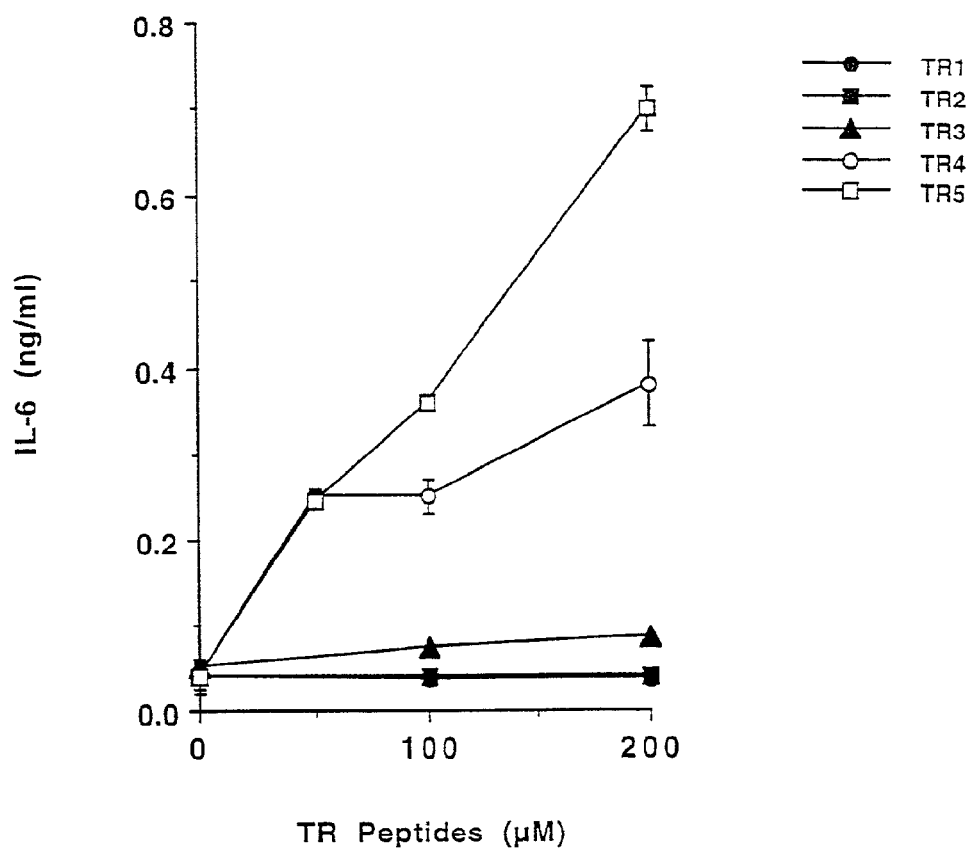

FIG. 17 is a graph showing synthetic peptides having amino acid sequences based upon the LTR of TS stimulate IL-6 release by PBMC. PBMC were cultured in media or in media containing a synthetic peptide at 50 mM, 100 mM or 200 MM. The synthetic peptides tested were TR1 (SEQ ID NO:32), TR2 (SEQ ID NO:26), TR3 (SEQ ID NO:27), TR4 (SEQ ID NO:28) or TR5 (SEQ ID NO:29).

Figures 18A, 18B, 18C:
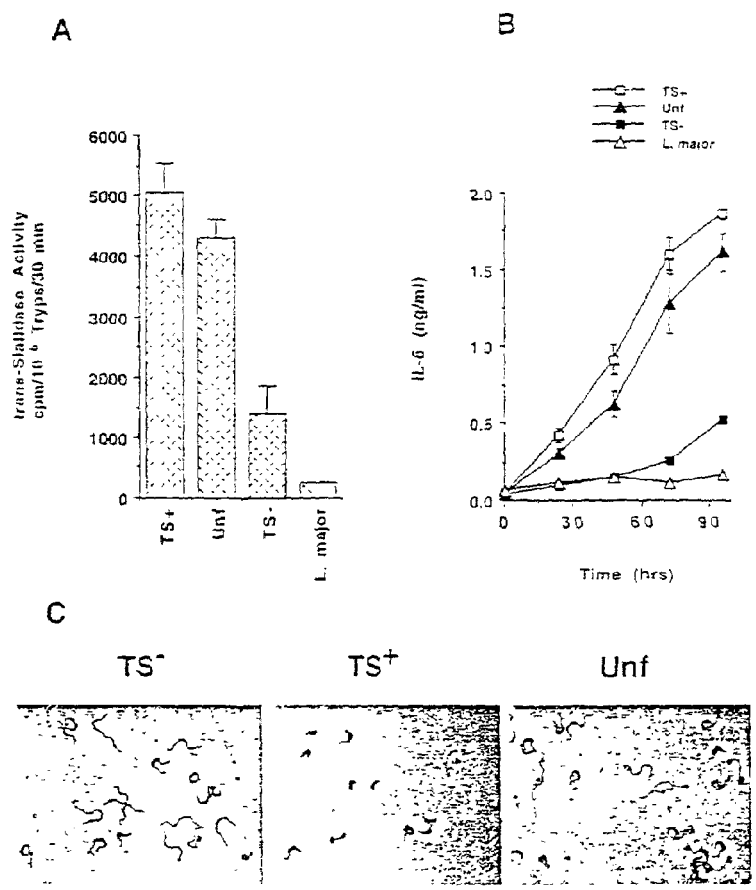

FIG. 18A is a graph showing the trans-sialidase activity of unfractionated *T. cruzi* trypomastigotes (Unf), or TS$^+$ *T. cruzi* trypomastigotes (TS$^+$), of TS$^-$ *T. cruzi* trypomastigotes (TS$^-$) and of *L. major* promastigotes (*L. major*).

FIG. 18B is a graph showing the quantity of IL-6 released by HIMEC after infection with and of *L. major* promastigotes (*L. major*).

FIG. 18C is a series of three photomicrographs showing the morphology of TS$^-$ *T. cruzi* trypomastigotes (TS$^-$), TS$^+$ *T. cruzi* trypomastigotes (TS$^+$) or unfractionated *T. cruzi* trypomastigotes (Unf).

Figure 19:
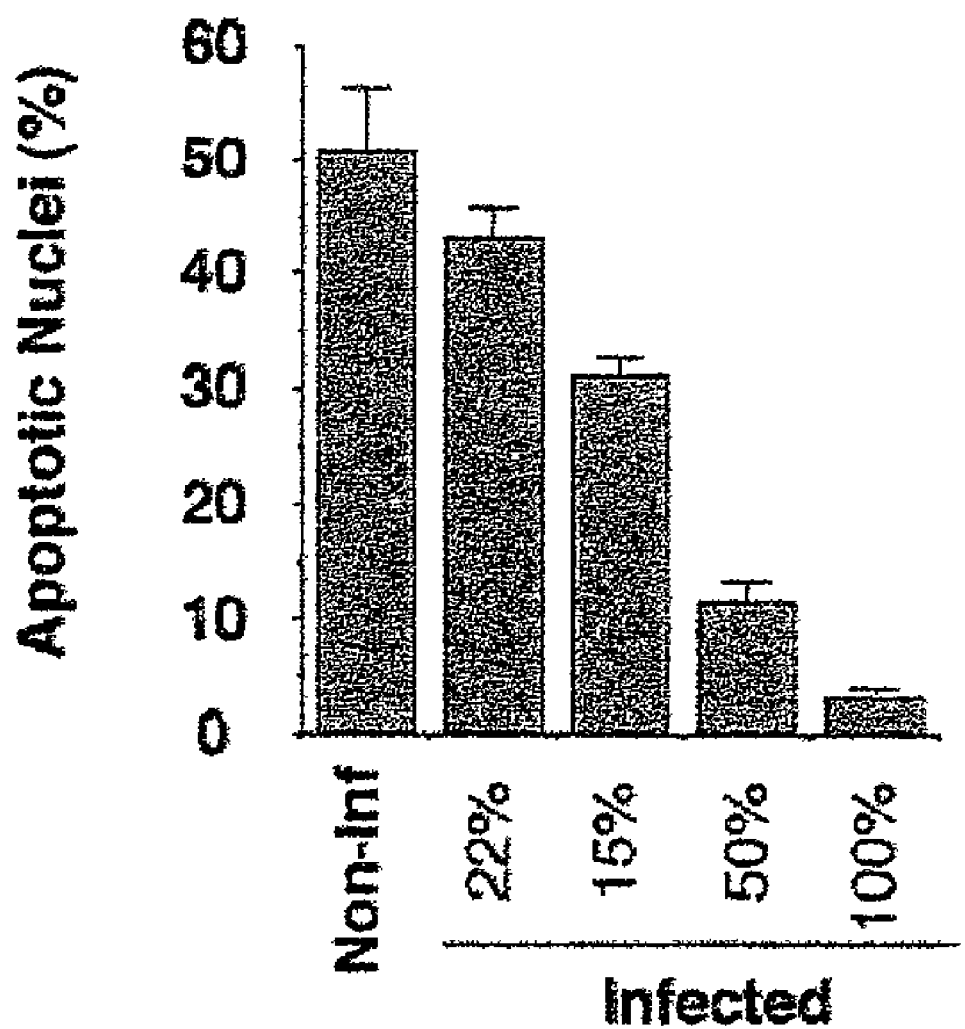

FIG. 19 is a bar graph showing that *T. cruzi* infection protected human Schwann cells from apoptosis. Monolayers of Schwann cells were infected with *T. cruzi* for 2 hours in DMEM/10% FCS and cultured for a further 72 hours in serum-free medium. To quantify apoptotic cells and infected cells, infected cell monolayers were examined by fluorescence microscopy after staining with DAPI, to reveal fragmented or condensed nuclei, and after staining with Chagasic IgG followed by Alexa 594-labeled anti-human IgG to reveal intracellular parasites. The bar graph illustrates the quantitative results.

Figures 20A, 20B, 20C:
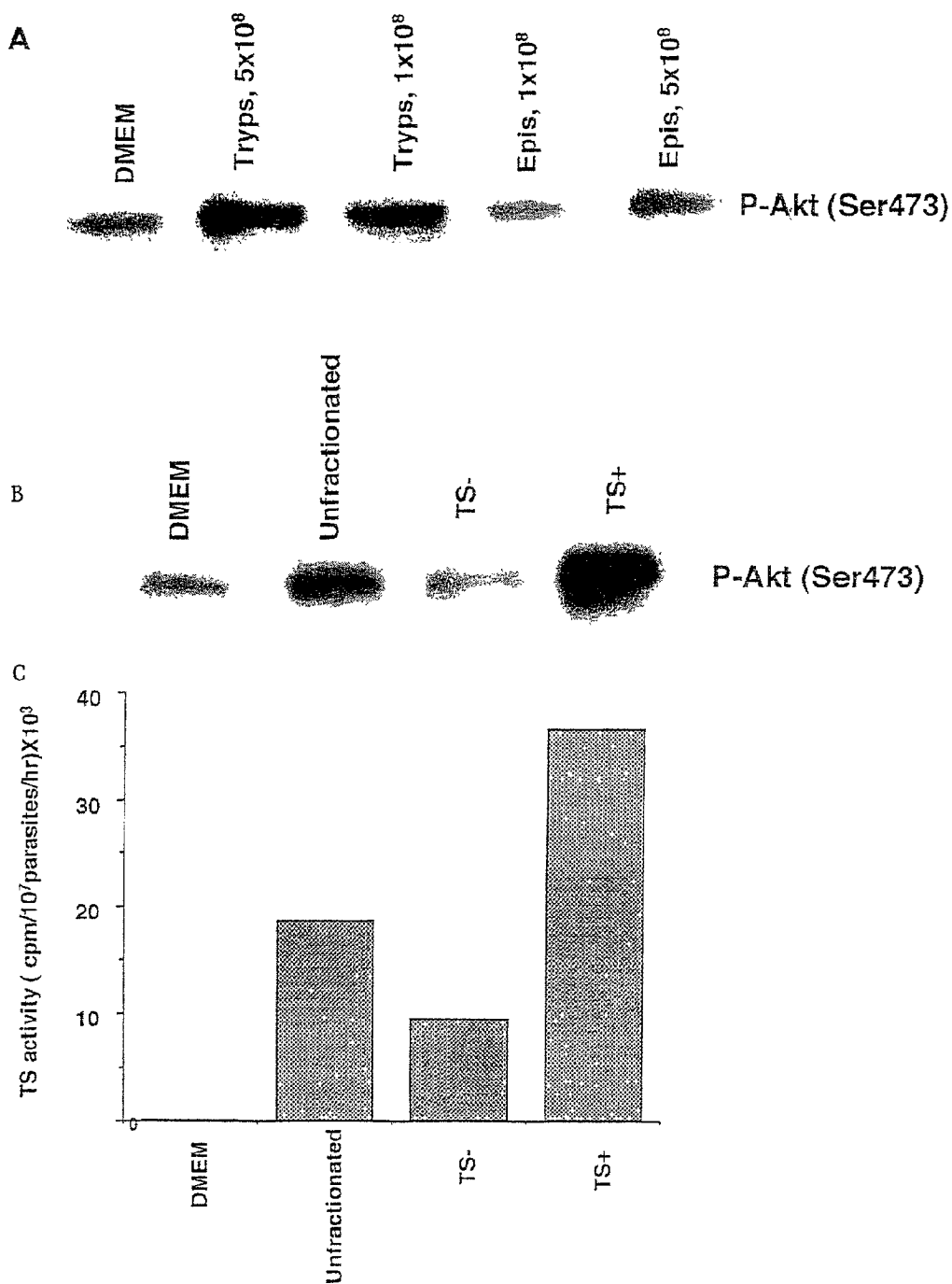

FIGS. 20A is a photograph of a Western blot showing that Akt kinase was activated in human Schwann cells infected with *T. cruzi* trypomastigotes. Schwann cells were grown in DMEM with 0.1% FCS for 2 days, changed to serum free medium for 1 hour, treated for 10 minutes with the indicated concentrations of invasive trypomastigotes (Tryps) and non-invasive epimastigotes (Epis), washed, lysed, and the lysates tested for Akt phosphorylation (Ser473) by Western blot. Infection with the invasive trypomastigotes resulted in the generation of phosphorylated Akt kinase (P-Akt (Ser473)).

FIGS. 20B and 20C are a photograph of a Western blot and a bar graph, respectively, showing that Akt kinase was activated in human Schwann cells infected with TS$^+$ *T. cruzi* trypomastigotes. Schwann cells were grown as described in the legend to FIG. 20A, and challenged for 20 minutes with $1\times10^7$ TS$^+$ trypomastigotes (TS$^+$; invasive form), TS$^-$ trypomastigotes (TS$^-$; noninvasive form), or unfractionated trypomastigotes. The cells were then washed, lysed, and the lysates tested for Akt phosphorylation (Ser473) by Western blot.

FIG. 20B shows that TS$^+$ trypomastigotes induced phosphorylation of Akt (P-Akt (Ser473)).

FIG. 20C shows the trans-Sialidase activity of the trypomastigotes populations used to infect the Schwann cells (note the heterogenous distribution of TS activity in the TS$^+$ and TS$^-$ subsets).

Figures 21A, 21B:
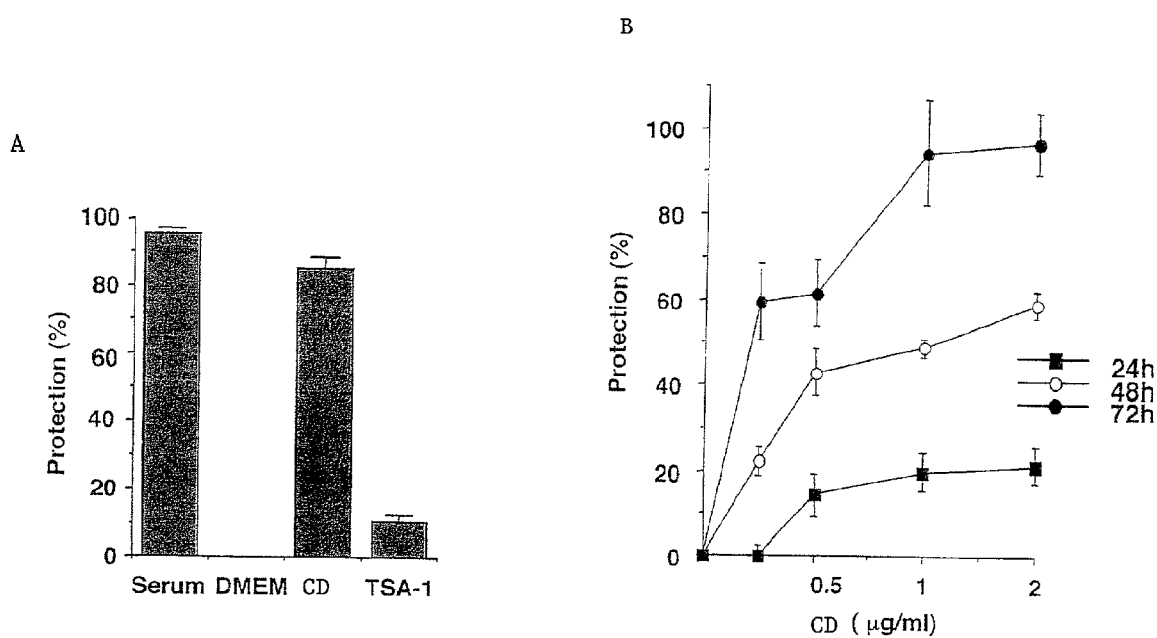

FIG. 21A is a bar graph showing that the catalytic domain of TS (CD, also referred to as TS-F or ΔTS) protected human Schwann cells from apoptosis. Nearly confluent Schwann cells were detached from the substratum by trypsinization, washed with serum-free DMEM, plated in the same medium with or without additives for 72 hours. Apoptotic cells were quantified by fluorescence microscopy after staining with DAPI, to reveal fragmented or condensed nuclei. The bar graph illustrates that CD was nearly as effective as 2% serum at inhibiting apoptosis. In contrast TSA-1 did not inhibit apoptosis in the assay.

FIG. 21B is a graph illustrating dose-dependent inhibition of serum withdrawal-induced apoptosis of human Schwann cells by CD. Immortalized Schwann cells were detached from the substratum by trypsinization, washed with serum-free DMEM, and plated in the same medium or in medium supplemented with CD at the indicated concentrations. After culture for 24, 48 or 72 hours, cells were fixed in 4% formaldehyde in phosphate buffered saline (PBS) for 10 minutes, washed with PBS and stained with DAPI (5 μg/mL) for 2 minutes. Cells with fragmented nuclei (apoptotic cells) were quantified by inspection using a fluorescence microscope.

Figure 22A:
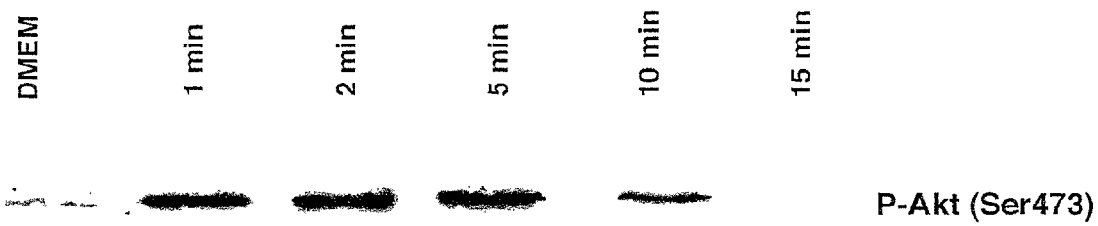

FIG. 22A is a photograph of a Western blot showing that CD induced transient phosphorylation of Akt kinase in human Schwann cells. Schwann cells were maintained in DMEM supplemented with 0.1% FCS for 2 days, switched to serum-free DMEM medium for 1 hour and challenged with CD (500 ng/ml) for 1, 2, 5, 10 or 14 minutes, lysed in lysis buffer and tested for phosphorylation of Akt kinase by immunoblot.

Figure 22B:
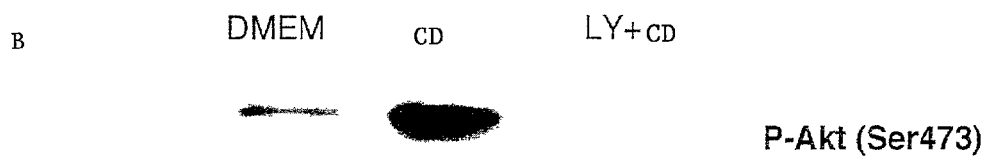
Figure 22C:
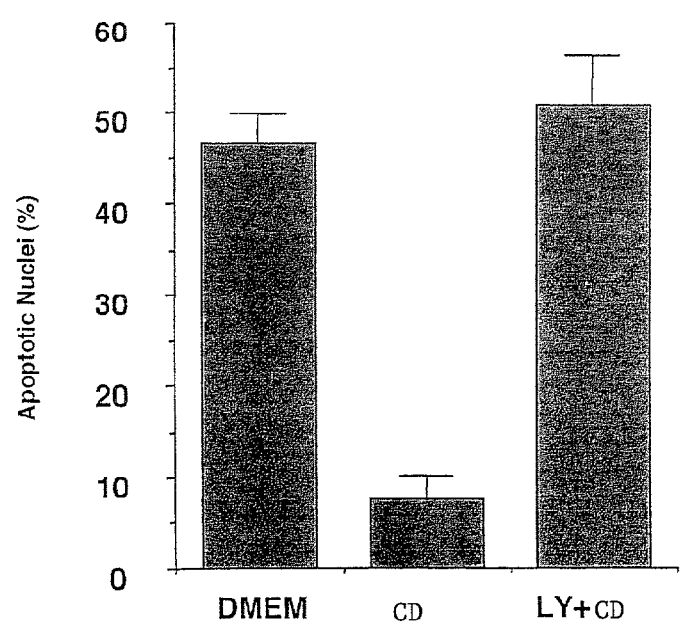

FIGS. 22B and 22C are a photograph of a Western blot and a bar graph, respectively, showing that CD activated P13K/Akt kinase signaling in human Schwann cells. Schwann cells were maintained in serum-free DMEM, in DMEM supplemented with 500 ng/ml CD for 2 minutes, or in DMEM that contained LY294002 (20 μg) for 30 minutes after which CD was added (final concentration of CD 500 ng/ml) and the cells were cultured for an additional 2 minutes (LY +CD). The resulting monolayers were fixed, stained with DAPI and the percentage of cells with fragmented (apoptotic) nuclei was calculated for each sample in triplicate.

FIG. 22B shows that CD induced phosphorylation of Akt kinase (P-Akt(Ser473)) and that the CD-induced phosphorylation of Akt kinase was inhibited by the P13 kinase inhibitor LY294002.

FIG. 22C shows that CD protected Schwann cells from apoptosis and that LY294002 inhibited the protective activity of CD. The CD-induced protection of Schwann cells from apoptosis correlated with CD-induced phosphoryl of Akt kinase.

Figures 23A, 23B:
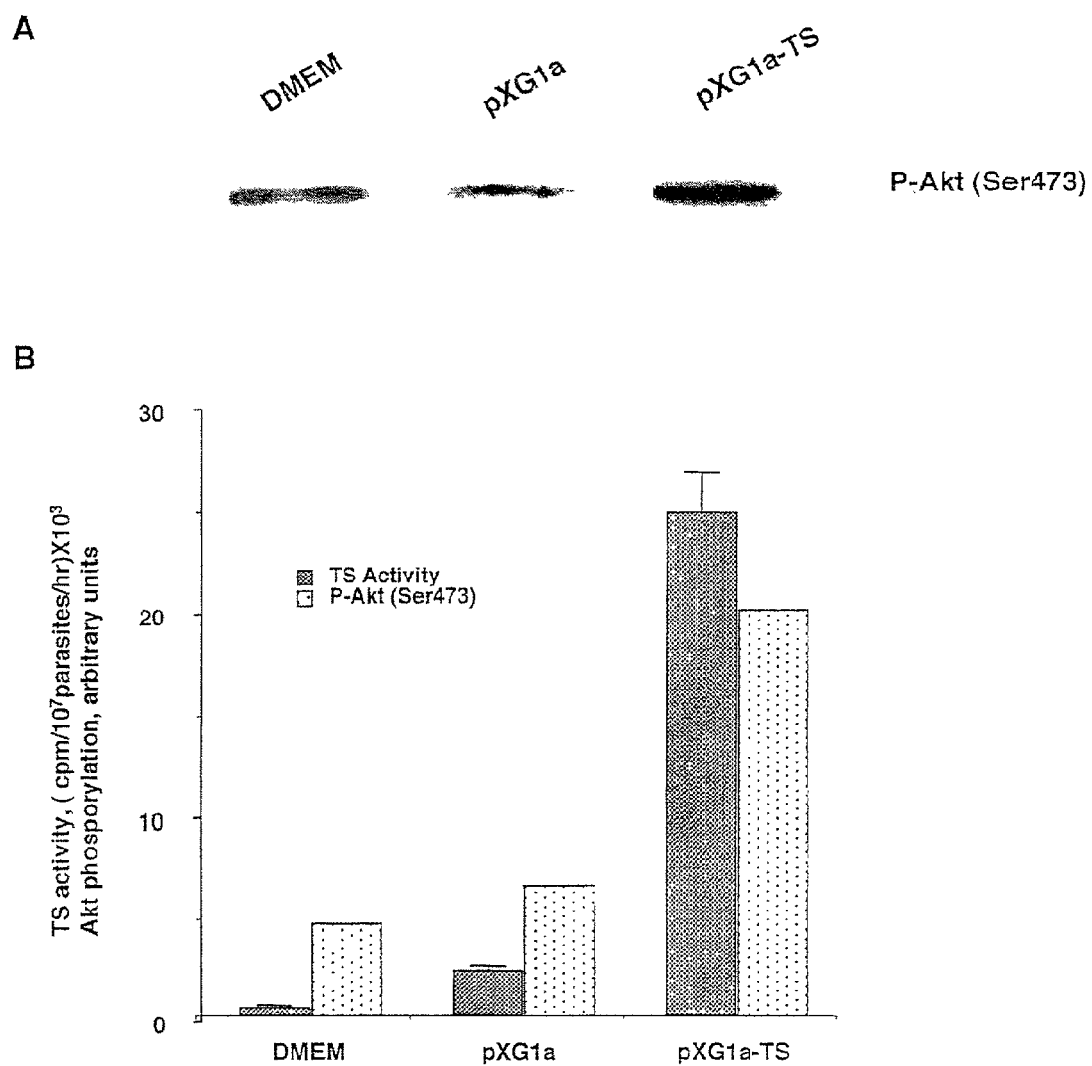

FIG. 23A is a photograph of a Western blot showing that *L. major* which expressed *T. cruzi* TS activated Akt in Schwann cells. Schwann cells were maintained as described in the legend for FIG. 22A and challenged with $10^8$/ml *L. major* promastigotes that were transfected with an empty vector (pXG1a) or with vector pXGl a-TS which encodes *T. cruzi* TS. Monolayers were washed, lysed and the lysates tested for Akt phosphorylation by immunoblot. The analysis revealed that *L. major* that expressed *T. cruzi* TS induced phosphoryation of Akt kinase (P-Akt(Ser473)).

FIG. 23B is a bar graph showing that *L. major* which expressed *T. cruzi* TS activated Akt in Schwann cells. The graph shows the relative amount of phosphorylated Akt kinase that was detected in Schwann cells challenged with $10^8$/ml *L. major* promastigotes transfected with an empty vector (pXG1a) or with vector pXG1a-TS which encodes *T. cruzi* TS, and the TS activity of *L. major* transfected with empty vector (PXG1a) or with vector pXG1a-TS which encodes *T. cruzi* TS. The results show that *L. major* that expressed TS induced phosphorylation of Akt kinase in Schwann cells.

Figures 24A, 24B:
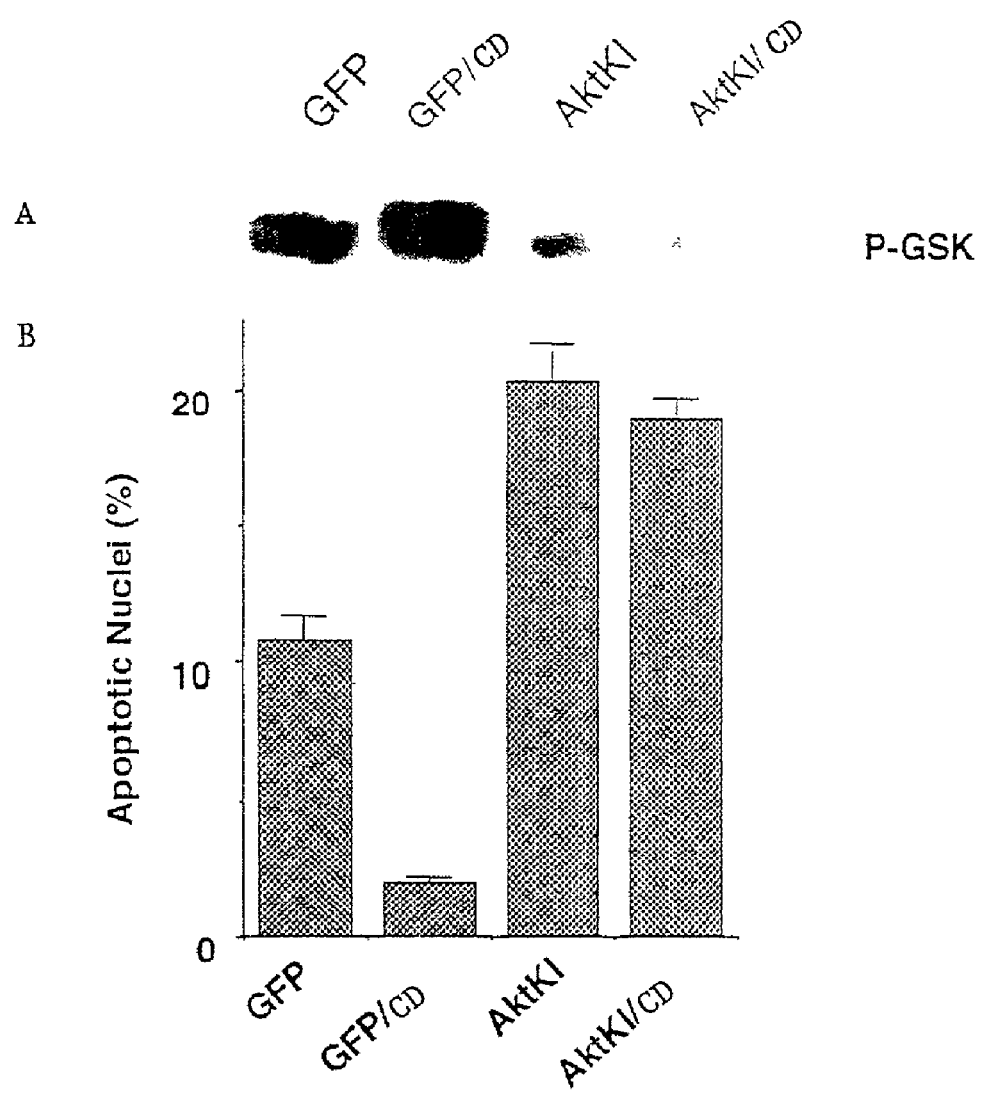

FIG. 24A is a photograph of a Western blot showing that CD did not activate Akt kinase in Schwann cells that over expressed a kinase-inactive mutant Akt (AktKI). Schwann cells were transfected with a vector encoding green fluorescent protein (GFP), or with vectors encoding GFP and a dominant negative mutant Akt kinase (AktKI). The transfected Schwann cells were maintained in 0.1% FCS for 48 hours without tetracycline to induce GFP and AktKI expression (GFP and AktKI, respectively) or maintained in 0.1% FCS for 48 hours without tetracycline and then challenged for 2 minutes with CD at 500 ng/ml (GFP/CD and AktKI/CD, respectively). The cells were then lysed on ice with nonionic detergent. Akt was immunoprecipitated from the lysates with an Akt-specific antibody and its kinase activity toward GSK-3a substrate assessed by immunoblot.

FIG. 24B is a bar graph showing that CD did not promote survival of Schwann cells that over expressed a kinase-inactive mutant Akt (AktKI). Schwann cells were cultured as described in the legend for FIG. 24A, except that the cells were maintained in serum-free medium for 48 hours without (GFP and AktKI) and with 500 ng/ml CD (GFP/CD and AktKI/CD). Cells that contained apoptotic nuclei were quantified after staining with DAPI. The resutls presented in FIGS. 24A and 24B show that CD did not promote survival or activate Akt kinase in Schwann cells which over expressed kinase-inactive Akt (AktKI).

Figures 25A, 25B:
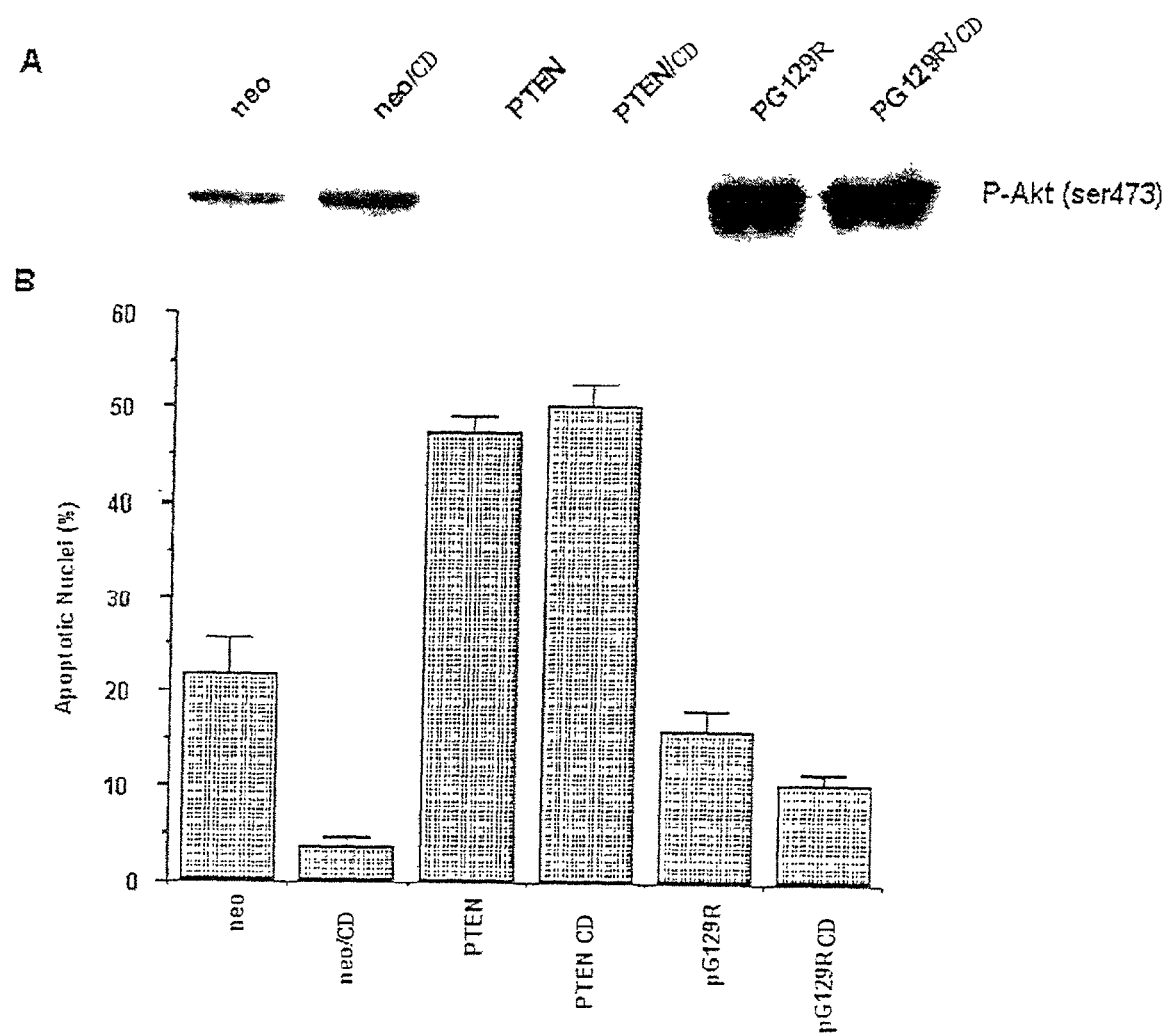

FIG. 25A is a photograph of a Western blot showing that CD did not induce phosphorylation of Akt kinase in Schwann cells that over expressed PTEN. Schwann cells were transfected with an empty vector pCDNA3-neo (neo), pCDNA3-neo-PTEN which encoded PTEN (PTEN) or with a vector that encoded a phosphatase-inactive pG129R PTEN mutant (pG129R). Transfected Schwann cells were grown in serum-free medium for 2 days without (neo, PTEN, pG129R) or with 500 ng/ml of CD (neo/CD, PTEN/CD, pG129R/CD). Then, the cells were lysed and the lysates examined for phosphorylation of Akt (Ser473) by Western blot. The results revealed that PTEN inhibited CD-induced phosphorylation of Akt kinase (P-Akt (Ser473)), but that an inactive mutant PTEN (PG129R) did not inhibit CD-induced phosphorylation of Akt kinase.

FIG. 25B is a bar graph showing that CD did not rescue Schwann cells that over expressed PTEN from apoptosis. Schwann cells were transfected with an empty vector pCDNA3-neo (neo), pCDNA3-neo-PTEN which encoded PTEN (PTEN) or with a vector that encoded a phosphatase-inactive pG129R PTEN mutant (pG129R) and were cultured as described in the legend to FIG. 25A, except the Schwann cell monolayers were fixed and the cells analyzed for apoptotic nuclei after DAPI staining.

FIGS. 26A–B illustrate the nucleotide sequence of the *T. cruzi* trans-sialidase gene, clone 7F (SEQ ID NO:33) deposited in GenBank under accession number M61732, having an open-reading frame beginning at position 484. The entire teachings of each of the information deposited in GenBank under accession number M61732 are incorporated herein by reference.

FIG. 26C illustrates the amino acid sequence of the *T. cruzi* trans-sialidase (SEQ ID NO:34) encoded by clone 7F deposited in GenBank under accession number M61732. TS comprises a catalytic domain (amino acid residues 33–666 of SEQ ID NO:34), and a tandem repeat domain (amino acid residues 667–1162 or SEQ ID NO:34).

DETAILED DESCRIPTION OF THE INVENTION

Acute Chagas' disease is characterized by robust growth of *T. cruzi* in several tissues throughout the body, which, in turn, can lead to severe damage of the nervous system. Humans with acute Chagas' disease, particularly young children, can suffer from fulminating encephalitis, and the autonomic nervous system is partially destroyed in experimental animals with acute *T. cruzi* infection (Alcantâra, F. G. *Parasit.* 10: 296–301(1959); Tafuri, W. L. *Am. J. Trop. Med. Hyg.* 19: 405–417 (1970); de Souza, M. M., et al., *Mem. Inst. Oswaldo Cruz* 91: 217–224 (1996)). The disease progresses from the acute phase to the indeterminate phase, which is distinguished by very low tissue parasitism, absence of symptoms, and paucity of lesions in the nervous system and other organs. Therefore, neuron regeneration must occur when Chagas' disease progresses from the acute disease to the indeterminate phase. Evidence for such neuron regeneration includes an increase in neurotransmitters in the heart, GI tract, and salivary glands (Machado, C. R., et al., *Am. J. Trop. Med. Hyg.* 27: 20–24 (1978); Tanowitz, H. B., et al., *Exp. Parasitol* 51: 269–278 (1981); Machado, C. R., et al., *Braz. J. Med. Biol. Res.* 20: 697–702 (1987)); motor unit remodeling; axonal sprouts; and remyelination in peripheral nerves (Gonzalez Cappa et al., *Am J Trop Med Hyg* 36:41–45 (1987); Losavio, A., et al., Am. J. Trop. Med. Hyg. 41: 539–547 (1989)). The disease can progresses to a lethal chronic stage. In this stage, patients exhibit autonomic neuropathy characterized by extensive fibrotic and inflammatory lesions in the muscles, autonomic ganglia, and nerves of the heart and GI tract (Köberle, F., *Adv. Parasitol* 6: 63–71 (1968); Andrade, Z. A., *Ciba Found Symp.* 99: 214–233 (1983); Adad, S. J., et al., *Rev. Inst. Med. Trop. São Paulo* 33: 443–450 (1991)). The molecular mechanisms that account for the long-lasting absence of neuropathy in the indeterminate phase and for the neurological manifestations in the chronic disease are unknown.

As described herein, a study of the effects of *T. cruzi* extracts and proteins on neurons and glial cells (e.g., Schwann cells) was conducted. In the course of this study it was determined that the *T. cruzi* neuraminadase (also referred to as trans-sialidase (TS)) can induce neurite outgrowth in neuronal cell lines, and can inhibit (i.e., reduce or prevent) neurotrophic factor withdrawal-induced apoptotic death of neuronal cells, glial cells and primary neurons. In fact, TS was more effective on a molar base than the prototypic mammalian neurotrophic factor NGF in preventing apoptosis of neuronal cells and primary neurons.

In further studies, the regions of TS which confer neurotrophic activity on the protein were identified. It was determined that TS and peptides derived from the catalytic domain of TS can directly induce neurite outgrowth and can protect neurons from neurotrophic factor withdrawal-induced apoptosis. In addition, it was determined that TS and peptides derived from the tandem-repeat domain of TS can induce the secretion of IL-6, a recognized neurotrophic factor that can protect neurons from apoptosis. Thus, TS can promote the differentiation and inhibit apoptosis of neurons directly and/or indirectly. For example, TS can induce production of endogenous neurotrophic factors (e.g., IL-6) and/or provide trophic support for glial cells (e.g., Schwann cells) which in turn support neurons.

The invention relates to TS and to the neurotrophic and IL-6 secretion-inducing activities of the protein. In one aspect, the invention relates to a method of providing trophic support for neurons and/or glial cells (e.g. Schwann cells) in a mammal (e.g., a human), comprising administering to the mammal a therapeutically effective amount of TS (e.g., SEQ ID NO:2, SEQ ID NO:34) or a neurotrophic variant thereof. The TS can be a naturally occurring enzyme which has neurotrophic and/or IL-6 secretion-inducing activity, an active variant thereof or an active fragment of a naturally occurring enzyme or active variant thereof. As used herein, "active variant" refers to variant proteins and/or peptides which have neurotrophic and/or IL-6 secretion-inducing activity. An "active variant" does not have to have neuraminadase or trans-sialidase catalytic activity. An active variant TS differs in amino acid sequence from a reference TS, such as the TS encoded by clone 19Y deposited in GenBank under accession number AJ002174 (SEQ ID NO:2) or the TS encoded by clone 7F deposited in GenBank under accession number M61732 (SEQ ID NO:34), but retains neurotrophic and/or L-6 secretion-inducing activity. Generally, differences are limited so that the sequences of the reference polypeptide and the active variant are closely similar overall and, in many regions, identical. An active variant TS and a reference TS can differ in amino acid sequence by one or more amino acid substitutions, additions, deletions, truncations, fusions or any combination thereof. Preferably, amino acid substitutions are conservative substitutions. A conservative amino acid substitution refers to the replacement of a first amino acid by a second amino acid that has chemical and/or physical properties (e.g, charge, structure, polarity, hydrophobicity/hydrophilicity) which are similar to those of the first amino acid. Conservative substitutions include replacement of one amino acid by another within the following groups: lysine (K), arginine (R) and histidine (H); aspartate (D) and glutamate (E); asparagine (N), glutamine (Q), serine (S), threonine (T), tyrosine (Y), K, R, H, D and E; alanine (A), valine (V), leucine (L), isoleucine (I), proline (P), phenylalanine (F), tryptophan (W), methionine (M), cysteine (C) and glycine (G); F, W and Y; C, S and T.

Active variant TSs include naturally occurring variants (e.g., allelic forms) and variants which are not known to occur naturally. As used herein, the term "active variant" includes fusion proteins.

Fusion proteins encompass polypeptides comprising TS (e.g., SEQ ID NO:2, SEQ ID NO:34) or an active variant thereof as a first moiety, linked via a covalent bond (e.g., a peptide bond) to a second moiety (a fusion partner) not occurring in the TS as found in nature. Thus, the second moiety can be an amino acid, oligopeptide or polypeptide. The second moiety can be linked to the first moiety at a suitable position, for example, the N-terminus, the C-terminus or internally. In one embodiment, the fusion protein comprises an affinity ligand (e.g., an enzyme, an antigen, epitope tag, a binding domain) and a linker sequence as the second moiety, and TS or a active portion thereof a the first moiety. Additional (e.g., third, fourth) moieties can be present as appropriate. The second (and additional moieties) can be any amino acid, oligopeptide or polypeptide that does not interfere with the neurotrophic or IL-6 secretion-inducing activity of TS.

Active variants of TS can be prepared using suitable methods, for example, by direct synthesis, mutagenesis (e.g., site directed mutagenesis, scanning mutagenesis) and other methods of recombinant DNA technology. Active variants can be identified and/or selected using a suitable assay, such as the neurite outgrowth, apoptosis and IL-6 assays described herein.

In one embodiment, an active variant of TS (e.g., neurotrophic variant, IL-6 secretion inducing variant) shares at least about 80% amino acid sequence similarity or identity with a naturally occurring TS (e.g., SEQ ID NO:2, SEQ ID NO:34), preferably at least about 90% amino acid sequence similarity or identity, and more preferably at least about 95% amino acid sequence similarity or identity with said TS. In another embodiment, a fusion protein comprises a first moiety which shares at least about 85% sequence similarity or identity with a TS (e.g., SEQ ID NO:2, SEQ ID NO:34), preferably at least about 90% sequence similarity or identity, and more preferably at least about 95% sequence similarity or identity with a TS. In another embodiment, the active variant comprises fewer amino acid residues than a naturally occurring TS. In this situation, the variant can share at least about 80% amino acid sequence similarity or identity with a corresponding portion of a naturally occurring TS (e.g., catalytic domain (amino acid residues 33–666 of SEQ ID NO:2, amino acid residues 33–666 of SEQ ID NO:34)), preferably at least about 90% amino acid sequence similarity or identity, and more preferably at least about 95% amino acid sequence similarity or identity with a corresponding portion of said TS. Portions of the amino acid sequence of TS which correspond to a variant and amino acid sequence similarity or identity can be identified using a suitable sequence alignment algorithm, such as 'BLAST 2 Sequences' using default parameters (Tatusova, T. A. et al., *FEMS Microbiol Lett,* 174:187–188 (1999)).

In one embodiment, the active variant comprises the amino acid sequence of peptide C44 (SEQ ID NO:12). In another embodiment, the active variant comprises the amino acid sequence of peptide C14 (SEQ ID NO:14).

In a preferred embodiment, TS or a neurotrophic variant thereof is co-administered to the mammal with a synergistic amount of a mammalian neurotrophic factor, such as a factor selected from the IL-6 family (e.g., IL-6, IL-11, LIF, CNTF, OSM). As used herein, the term "synergistic amount" refers to a quantity of a mammalian neurotrophic factor which, when co-administered with TS, produces a neurotrophic effect that is greater than the sum of the effects of each agent individually. A synergistic amount can be an amount which provides little or no trophic support when administered without TS. Thus, the amount of each agent that is administered to the mammal can be greatly reduced and undesirable side effects, such as those observed when certain mammalian neurotrophic factors are administered (e.g., CNTF), can be substantially reduced or eliminated. Preferably, the co-administered neurotrophic factor is CNTF or LIF.

In additional embodiments, the active variant is a fusion protein comprising TS or a neurotrophic variant thereof as a first moiety and a suitable fusion partner as a second moiety. In one embodiment, the fusion protein comprises the amino acid sequence of peptide C14 (SEQ ID NO:14) or a neurotrophic variant thereof. In another embodiment, the fusion protein comprises two or more of the 12 amino acid repeats (e.g., peptide TR1 (SEQ ID NO:32)) of the TS tandem repeat domain. In another embodiment, the fusion protein comprises an amino acid sequence in which the amino acid sequence of peptide TR1 (SEQ ID NO:32) or an IL-6 inducing variant thereof occurs at least twice. In another embodiment, the fusion protein comprises a second moiety (fusion partner) which is a mammalian (e.g., human) neurotrophic factor. In a particular embodiment, the fusion protein comprises a second moiety (fusion partner) that is selected from the group consisting of CNTF and LIF.

Under certain circumstances it can be advantageous to administer one or more neurotrophic and/or IL-6 secretion-inducing peptides which are based on the sequence of TS to the mammal. For example, peptides which are directly neurotrophic can be administered, thereby providing neurotrophic support without inducing the expression of IL-6 or other growth factors which can be undesirable in certain circumstances.

Peptides C44 (SEQ ID NO:12), CFN-1 (SEQ ID NO:13) and C14 (SEQ ID NO:14) which are based on the sequence of the TS catalytic domain can be administered to a mammal to provide trophic support for neurons and/or glial cells. It is anticipated that variants of these peptides can retain neurotrophic activity and be suitable for use in the method of the invention. Such active variants can differ in amino acid sequence from the reference peptide by one or more amino acid substitutions, additions, deletions, truncations, fusions or any combination thereof as described herein. It is farther anticipated the peptides which comprise fewer than fourteen amino acids can have neurotrophic activity. Such peptides can be prepared by deleting one or more terminal and/or internal amino acids from peptide C14 (SEQ ID NO:14) using conventional methods and assaying the peptides for neurotrophic activity as described. For example, the peptide can have about 3 to about 13 amino acids.

In another embodiment, the invention is a method of providing neurotrophic support for neurons and/or glial cells in a mammal, comprising administering to said mammal a therapeutically effective amount of a peptide comprising the amino acid sequence of peptide C14 (SEQ ID NO:14) or a neurotrophic variant thereof. In another embodiment, the neurotrophic peptide is co-administered with a synergistic amount of a mammalian neurotrophic factor.

The amino and carboxyl termini of the peptides described herein can each, independently, be unprotected or protected by a suitable protecting group. Suitable groups for protecting amino and carboxyl groups are known in the art. See, for example, Greene and Wuts, "Protective Groups in Organic Synthesis", John Wiley & Sons (1991), the teachings of which are incorporated herein by reference.

The method can be employed to provide trophic support for neurons and/or glial cells in a mammal in need thereof. For example, the method can be employed to treat a mammal with a congenital or acquired condition characterized by neural degeneration, such as amyotrophic lateral sclerosis, Alzheimer's disease, Parkinson's disease, Huntington's disease, Chagas' disease, peripheral neuropathy, palsies (e.g., cerebral, facial, Bell's, bulbar, gaze, oculomotor, progressive supranuclear, trochler), multiple sclerosis and the like. The method can also be employed to treat a mammal which has experienced a stroke (ischemic stroke) or trauma to the brain, spinal cord or peripheral nerves.

TS and peptides which induce the secretion of IL-6 can be administered to a mammal to provide neurotrophic support or for other therapeutic purposes. As described herein, TS and peptides which comprise an amino acid sequence in which the amino acid sequence of peptide TR1 (SEQ ID NO:32) occurs at least twice can induce the secretion of IL-6. Preferably, the amino acid sequence of peptide TR1 (SEQ ID NO:32) occurs about five or about six times in tandem (i.e., one occurrence of the sequence is immediately preceded and/or followed by another occurrence of the sequence). It is anticipated that peptides comprising an amino acid sequence in which the amino acid sequence of a variant of peptide TR1 (SEQ ID NO:32) occurs at least twice can induce the secretion IL-6. Such variants can be prepared using conventional methods and assessed for IL-6 secretion inducing activity as described herein.

In another aspect, the invention is a method of stimulating the secretion of IL-6 in a mammal (e.g., a human), comprising administering to the mammal a therapeutically effective amount of TS or an IL-6 secretion-inducing variant thereof. In one embodiment, the variant comprises an amino acid sequence in which the amino acid sequence of peptide TR1 (SEQ ID NO:32) occurs at least twice. In another embodiment, the variant is a fusion protein. In another embodiment, a peptide comprising an amino acid sequence in which the amino acid sequence of peptide TR1 (SEQ ID NO:32) or an IL-6 secretion-inducing variant thereof occurs at least twice is administered to a mammal to stimulate the secretion of IL-6.

IL-6 is a cytokine with a variety of biological activities including regulation of the immune response, hematopoiesis and inflammation, in addition to neurotrophic activity. Thus, the method of the stimulating the secretion of IL-6 can be used to treat a mammal in need of neurotrophic support or modulation of the immune response, hematopoiesis or inflammatory response.

According to the methods of the invention, TS, active variants thereof (e.g., peptides, fusion proteins) and/or other therapeutic agents (e.g., CNTF, LIF) can be administered to the mammal by any appropriate route. A therapeutically effective amount is administered. A therapeutically effective amount is an amount sufficient to achieve the desired therapeutic or prophylactic effect, under the conditions of administration, such as an amount which is sufficient to induce neural development or regeneration, inhibit (i.e., reduce or prevent) apoptosis of neurons and/or glial cells, improve the neurological functions of the mammal, induce the expression of the bcl-2 gene, activate Akt kinase or induce the secretion of IL-6. TS, active variants thereof (e.g., peptides, fusion proteins) and any other agent (e.g., mammalian neurotrophic factor) to be administered can be administered in a single dose or multiple doses. The dosage can be determined by methods known in the art and is dependent, for example, upon the type of disorder, the mammal's age, sensitivity and tolerance to drugs, and overall well-being. Typically, an effective amount can range from about 0.001 mg/kg per day to about 10 mg/kg per day for an adult.

A variety of routes of administration are possible including, for example, oral, dietary, topical, transdermal, rectal, parenteral (e.g., intravenous, intraarterial, intraperitoneal, intramuscular, intrathecal, intracerebral, subcutaneous injection, intradermal injection), and inhalation (e.g., intrabronchial, intranasal or oral inhalation, intranasal drops) routes of administration, depending on the condition to be treated. Administration can be local or systemic as indicated. The preferred mode of administration can vary depending upon the particular condition (e.g., disease) being treated, however, parenteral or oral administration is generally preferred.

TS and/or active variants thereof (e.g., peptides, fusion proteins) and any additional therapeutic agents can be administered as neutral compounds or as physiologically acceptable salts. Salts of compounds containing an amine or other basic group can be obtained, for example, by reacting with a suitable organic or inorganic acid, such as hydrogen chloride, hydrogen bromide, acetic acid, perchloric acid and the like. Compounds with a quaternary ammonium group also contain a counteranion such as chloride, bromide, iodide, acetate, perchlorate and the like. Salts of compounds containing a carboxylic acid or other acidic functional group can be prepared by reacting with a suitable base, for example, a hydroxide base. Salts of acidic functional groups contain a countercation such as sodium, potassium and the like.

TS and/or active variants thereof (e.g., peptides, fusion proteins) can be administered to the mammal as part of a composition comprising an isolated TS and/or active variant thereof (e.g., peptides, fusion proteins) and a pharmaceutically or physiologically acceptable carrier. The composition can further comprise an additional therapeutic agent, such as a mammalian neurotrophic factor (e.g., CNTF, LIF). Formulation will vary according to the route of administration selected (e.g., solution, emulsion, capsule). Suitable physiological carriers can contain inert ingredients which do not interact with TS, variants, peptides and agents. Standard pharmaceutical formulation techniques can be employed, such as those described in Remington's Pharmaceutical Sciences, Mack Publishing Company, Easton, Pa. Suitable physiological carriers for parenteral administration include, for example, sterile water, physiological saline, bacteriostatic saline (saline containing about 0.9% benzyl alcohol), phosphate-buffered saline, Hank's solution, Ringer's-lactate and the like. Methods for encapsulating compositions (such as in a coating of hard gelatin or cyclodextran) are known in the art (Baker, et al., "Controlled Release of Biological Active Agents," John Wiley and Sons, 1986). For inhalation, the agent can be solubilized and loaded into a suitable dispenser for administration (e.g., an atomizer, nebulizer or pressurized aerosol dispenser).

Furthermore, TS and/or active variants thereof (e.g., peptides, fusion proteins) can be administered via in vivo expression of the recombinant protein. In vivo expression can be accomplished via somatic cell expression according to suitable methods (see, e.g. U.S. Pat. No. 5,399,346). In this embodiment, a nucleic acid encoding the protein or peptide can be incorporated into a retroviral, adenoviral or other suitable vector (preferably, a replication deficient infectious vector) for delivery, or can be introduced into a transfected or transformed host cell capable of expressing the protein or peptide for delivery. In the latter embodiment, the cells can be implanted (alone or in a barrier device), injected or otherwise introduced in an amount effective to express the protein or peptide in a therapeutically effective amount.

In another aspect, the invention relates to the active peptides described herein. In one embodiment, the invention is a neurotrophic peptide comprising the amino acid sequence of peptide C14 (SEQ ID NO:14) or a neurotrophic variant thereof. In another embodiment, the neurotrophic peptide comprises an amino-terminal protecting group, a carboxyl-terminal protecting group or a combination thereof In another embodiment, the invention is an IL-6 secretion-inducing peptide comprising an amino acid sequence in which the amino acid sequence of peptide TR1 (SEQ ID NO:32) or an IL-6 secretion-inducing variant thereof occurs at least twice. The IL-6 secretion-inducing peptide can further comprise an amino-terminal protecting group, a carboxyl-terminal protecting group or a combination thereof.

In another aspect, the invention relates to the active TS variants described herein. In one embodiment, the invention is a fusion protein wherein the TS component comprises the amino acid sequence of peptide C14 (SEQ ID NO:14) or a neurotrophic variant thereof. In another embodiment, the fusion partner is a mammalian neurotrophic factor, such as CNTF or LIF. In an additional embodiment, the fusion protein comprises an amino acid sequence in which the amino acid sequence of peptide TR1 (SEQ ID NO:32) or an IL-6 secretion-inducing variant thereof occurs at least twice, and a suitable fusion partner.

In another aspect, the invention relates to compositions comprising TS, active variants thereof (e.g., neurotrophic and/or IL-6 secretion-inducing peptides, as described herein), and a physiologically acceptable carrier. The compositions can further comprise a mammalian neurotrophic factor. In one embodiment, the composition comprises a neurotrophic peptide comprising the amino acid sequence of peptide C14 (SEQ ID NO:14) or a neurotrophic variant thereof. In another embodiment, the composition comprises a fusion protein wherein the TS component comprises the amino acid sequence of peptide C14 (SEQ ID NO:14) or a neurotrophic variant thereof. In another embodiment, the composition comprises an IL-6 secretion-inducing peptide comprising an amino acid sequence in which the amino acid sequence of peptide TR1 (SEQ ID NO:32) or an IL-6 secretion-inducing variant thereof occurs at least twice. In another embodiment, the composition comprises an IL-6 secretion-inducing fusion protein comprising an amino acid sequence in which the amino acid sequence of peptide TR1 (SEQ ID NO:32) or an IL-6 secretion-inducing variant thereof occurs at least twice. In a particular embodiment, the composition comprises TS or a neurotrophic variant thereof, a mammalian neurotrophic factor and a physiologically acceptable carrier.

The invention further relates to TS, active variants thereof (e.g., neurotrophic and/or IL-6 secretion-inducing peptides having amino acid sequences based on TS) as described herein for use in therapy (including prophylaxis) or diagnosis, and to the use of TS, active variants thereof and active peptides having amino acid sequences based on TS for the manufacture of a medicament for the treatment of a particular disease or condition as described herein (e.g., amyotrophic lateral sclerosis, Alzheimer's disease, Parkinson's disease, Huntington's disease, Chagas' disease, peripheral neuropathy, palsies (e.g., cerebral, facial, Bell's, bulbar, gaze, oculomotor, progressive supranuclear, trochler), multiple sclerosis, stroke, brain trauma, spinal cord trauma and peripheral nerve trauma).

EXEMPLIFICATION

Example 1

TS and Peptides Derived from TS Promote Survival of Neurons

Materials And Methods

Growth Factors, Cytokines, and Synthetic Peptides

Mouse 7S nerve growth factor (NGF) was purchased from Collaborative Biomedical Products (Bedford, Mass.); human ciliary neurotrophic factor (CNTF) was a gift of Dr. E. Granowitz (New England Medical Center, Boston, Mass.); and recombinant human and rat CNTF, as well as the neuraminidases from *V. cholera, C. perfringens*, and Newcastle disease virus, were from Calbiochem. Recombinant human IL-11, leukemia inhibitory factor (LIF), and oncostatin-M were from Sigma (St. Louis, Mo.), while recombinant human IL-6 was from Endogen. Synthetic peptides were made at the Tufts Biotechnology Center (Tufts University, Boston, Mass.). The peptides were dissolved in RPMI/0.2% BSA prior to the neuronal assays.

Purification of TS

TS was purified by immuno-affinity chromatography as described previously (Scudder et al., *J. Biol. Chem.* 268: 9886–9891(1993)). In brief, supernatants from T. cruzi-infected Vero cells were passed on a protein-G Sepharose (Pharmacia) column adsorbed with mAb TCN-2 specific for the LTR domain of TS. Bound TS was eluted with TR1 peptide (SEQ ID NO:32) in the presence of 0.1% octyl glucopyranoside. TS was concentrated by ultrafiltration in Amicon-10 and washed extensively with PBS pH 7.8 to remove the TR1 (SEQ ID NO:32) peptide.

The neuraminidase from *Vibrio cholera* was purchased from Calbiochem. Penetrin was isolated by heparin-affinity chromatography as described previously (Ortega-Barria et al., *Cell* 67: 411–421 (1991)). All reagents, glassware and plasticware used in the isolation of the various proteins were LPS-free. To eliminate residual LPS, the purified materials were passed through two distinct resins that remove endotoxin by different mechanisms, END-X B 15 (Associates of Cape Cod, Woods Hole, Mass.) and AffinityPak Detoxi-Gel (Pierce, Rockford, Ill.), following the recommendations of the manufacturers.

Cloning and Expression of Recombinant Fragments of Trans-sialidase

The DNA fragments corresponding to the catalytic domain of TS were amplified by PCR using, as templates, TS clone 19Y (SEQ ID NO:1) or clone 7F (SEQ ID NO:33) from a genomic DNA library of *T. cruzi* trypomastigote clone MV-13 (Pereira, M. E. A., et al., *J. Exp. Med.* 174: 179–191 (1991), incorporated herein by reference). A 1899 bp segment of DNA encoding the full catalytic domain of TS, referred to herein a TS-F (also referred to herein as CD), was obtained with synthetic DNA primers TS 1 respectively. DNA encoding fragment TS-F-47 was prepared using clone 7F as template. DNAs encoding fragments TS-CC-47 or TS-Cat-47 were prepared using clone 19Y as template. The amplified DNA fragments were cloned into pET 23b (Novagen) to generate a construct encoding a stretch of 6 histidine residues at the C-terminus of the expressed proteins. A plasmid encoding CD from clone 7F and a plasmid encoding CD from clone 19Y were produced. CD from clone 19Y or from 7F was active in the studies using PC12 cells.

For protein production, plasmids were transferred to *E. coli* strain B12-1 DE3 (Novagen), containing a chromosomal copy of the T7 RNA polymerase gene. Expression was induced by Isopropyl-β-D-thiogalactopyranoside (IPTG.) To isolate the recombinant TS fragments, bacterial lysates were prepared by osmotic shock in 40 mM phosphate buffer, 0.3 M NaCl, 1% Triton X-100, 1 mM PMSF, followed by brief sonication. In the lysates containing TS-F-47, TS-CC-47 and TS-Cat-47 urea was added to 8 M, to facilitate solubilization. Suspensions were centrifuged for 30 minutes at 20,000×g and the supernatant loaded on a $Ni^{2+}$-nitrilotriacetic acid/agarose column as recommended by the manufacturer (Novagen). For refolding of the urea-soluble proteins the purified polypeptides were incubated in a solution containing 8M urea, 50 mM Tris/HCl, pH 8.0, 5 mM 1.4-dithio-DL-threitol, and 1 mM EDTA. Reduction was performed overnight at 4° C. The solution was then diluted with 4 vol of 50 mM Tris/HCl, pH 8.0 containing 1.25 mM reduced and oxidized glutathione, followed by dialysis overnight against 10 mM Tris/HCl, pH 8.0 at 4° C. (see, for example, Marti, D., et al., *Eur. J. Biochem.* 219: 455–462 (1994)) Urea was not required for solubilization of TS-F fragment, which was purified by affinity chromatography on $Ni^{2+}$-agarose and by FPLC on the anion-exchange column MonoQ HR (Pharmacia), as previously described (Scudder, P. et al., *J. Biol. Chem.* 268: 9886–9891 (1993)).

The full-length C-terminal long tandem repeat (LTR fragment) of TS was generated in insect cells. LTR, sucloned from a pMelBac plasmid (Invitrogen) containing the TS gene of clone 7F (Pereira, M. E. A., et al., *J. Exp. Med.* 174: 179–191 (1991), incorporated herein by reference), was digested with Pvu II/Sal I and ligated into EcoR V/Sal I sites

```
5'-GGAATTCCATATGGCACCCGGATCGAGCCGAGTT-3'     (SEQ ID NO:3) and

MP10 5'-CCGCTCGAGGCTCAAGAACAAGGTCCTGATCG-3'  (SEQ ID NO:4).
```

For amplification of DNA encoding fragments TS-F-47, TS-CC-47 and TS-Cat-47 of TS, a common forward synthetic DNA primer Mp13 5'

```
Mp13 5'-GGGAATTCGGTTGCCAATCGCGGACGCTC-3' (SEQ ID
NO:5)
``` was used together with reverse DNA primer MP10 (SEQ ID NO:4), of pET20b (Novagen). The LTR DNA was introduced into the Nco I/Hind m sites of pFASTBAC HTh vector (Gibco BRL). The Bac-to Bac system (Gibco BRL) was used to generate recombinant baculovirus, which in turn was used to infect Sf9 cells. Recombinant LTR protein was purified by $Ni^{2+}$-NTA column (Novagen), followed by affinity chromatography on mAb TCN-2 (Prioli, R. P., et al., *Mol. Biochem. Parasitol* 52: 85–96 (1992)). The LTR fragment thus generated contains the full-length tandem repeat of clone 7F

```
MP12 5'-CCCCTCGAGATTTGCCGTGCTTGCGT-3'      (SEQ ID NO:6) or

MP11 5'-CCCCTCGAGCCGACAAAAAGCCAACAAAGAC-3' (SEQ ID NO:7),
``` plus a TS sequence of 26 amino acids upstream and 40 amino acids downstream of the repeat.

The relative amount of recombinant protein produced by the bacteria was determined by quantifying Pro Blue (Integration Separation System) stained proteins separated by 10% SDS-PAGE using a Gel Doc 1000 apparatus (Bio Rad). Various quantities of BSA were run on the gels as standards. Alternatively, the recombinant proteins were blotted to nitrocellulose membrane and visualised with T7-Tag antibody (Novagen) or with a mouse polyclonal antibody against TS.

Cell Cultures

PC12 cells were obtained from ATCC (Manassas, Va. (Accession No. CRL-1721)) and cultured on collagen-coated dishes in RPMI 1640 supplemented with 10% horse serum and 5% fetal bovine serum (Greene, L. A. and Tishler, A. S., *Proc. Natl. Acad. Sci. USA,* 73: 2424–2428 (1976)). For differentiation and survival experiments, cells were washed three times in serum-free RPMI/0.2% BSA, plated in the same medium in collagen-coated plastic dishes at $2\times10^5$/ml, without and with growth factors, TS, recombinant proteins, synthetic peptides, for the time and concentrations indicated in the Figures.

Neurite Outgrowth Assay 96-well microtiter plates were coated overnight at 4° C. with the TS or peptides or fragments thereof, or with control proteins laminin (Ln) or bovine serum albumin (BSA) at 500 µg/ml. After removing the compounds, the plates were further incubated with 1% BSA for 1 hour at room temperature and immediately used as substratum for PC12 or N18 (Prasad, K. N., *Biol Rev Camb Philos Soc,* 66:431–451 (1991)) cells in serum-free RPMI/0.2% BSA. Neurite outgrowth was measured using a phase-contrast microscope 17 hours later. Cells exhibiting neurite outgrowth were those having one or more cytoplasmic extension >2 µm in length.

Assays for Cell Survival

Cell staining with 4,6-diamino-2-phenylindole (DAPI). Cells were fixed with 4% formaldehyde in PBS for 5 minutes, washed with PBS, stained with 10 µg/ml DAPI (Sigma) for 2 minutes, washed with PBS, and visualized under UV light using a fluorescent microscope. About 300–400 cells were examined under the microscope to determine the percentage of apoptotic cells.

Cell DNA nick end labeling (TUNEL) (Gavrieli, Y., et al., *J. Cell. Biol.* 119: 493–501 (1992)) assay was performed using a kit purchased from Boehringer Mannheim as described by the manufacturer.

Protection against apoptosis of PC12 cells in serum-free medium containing a test agent (agent N )(e.g., protection induced by TS, TS fragments, NGF or other growth factors), was calculated by the formula: 100%−[(apoptosis(%) of cells kept in RPMI containing test agent N÷apoptosis (%) of cells kept in RPMI)×100%]. Testing the effect of wortmannin (Sigma) and LY294002 (Sigma) in inhibiting the neuroprotection of TS was performed following the protocol described by others (Yao and Cooper, *Science,* 267:2003–2006 (1995); D'Mello et al., *J. Neurosci* 17:1548–1560 (1997)). In brief, PC12 cells were switched from growth medium to RPMI without and with TS or various other growth factors. After 24 hr, wortmannin and LY294002 were added to the cultures. After another 24 hrs, cells were examined for apoptosis by the DAPI assay, as above.

RNA Preparation and Reverse Transcription Reactions

Total RNA was extracted from PC12 cells by the acid guanidinum isothiocyanate method (Chomchinski, P., et al., *Biotechniques* 15: 532–535 (1993)) using TR1-reagent (Molecular Research Center, Inc.). cDNA synthesis was performed according to the instruction of the manufacturer (Gibco-BRL). Reverse transcription reactions were carried out for 50 minutes at 42° C. and were heated to 70° C. for 15 minutes to terminate the reaction using a MiniCycler (MJ Research). Samples were cooled to 4° C. and stored at −20° C. until use.

Quantitative PCR of Bcl-2 Gene Transcripts

PCR reactions were performed in 50 µl containing 1.5 µl of template DNA (corresponding to cDNA synthesized from 100 ng of total RNA), 1× PCR buffer, 100 µM of deoxynucleotides, 2.5 mM $MgCl_2$, 10 mM DTT, 10 pM of Bcl-2 primers, and 2 U of Taq DNA polymerase (Gibco-BRL). The synthetic DNA primers for the rat Bcl-2 were: 5'-AGAT-GAAGACTCCGCGCCCCTGAGG-3' (SEQ ID NO:8) and 5'-CCAGGTATGCACCCAGAGTGATG-3'(SEQ ID NO:9) to give a PCR product of 566 bp. The sequences for synthetic GAPDH DNA primers (Wong, H., et al., *Anal. Biochem.* 223: 251–258 (1994)) were: 5'-CGGAGT-CAACGGATTTGGTCGTAT-3' (SEQ ID NO:10) and 5'-AGCCTTCTCCATGGTGGTGAAGAC-3' (SEQ ID NO:11) giving a PCR produce of 306 base pairs. Amplifications were carried out in MiniCycler (MJ Research) using following conditions: 98° C. for 5 minutes (initial heat denaturation), 3 cycles of 94° C. for 1 minute, 63° C. for 1 minute, 72° C. for 1.5 minutes; 3 cycles of 94° C. for 1 minutes, 60° C. for 1 minute, 72° C. for 1.5 minutes, followed by 72° C. for 10 minutes. Primers for GAPDH (10 pM) were added at cycle 7 by the "primer-dropping" method. Aliquots of PCR reaction products were separated by electrophoresis in 2% agarose gels (Ultrapure, Gibco-BRL), containing 0.2 µg/ml ethidium bromide. Gels were analyzed by computerized densitometric scanning using Gel doc 1000 (Bio Rad) and Molecular Analyst Software, version 2.1.

Trans-Sialidase Assay

The trans-sialidase assay was performed as described (Scudder et al., *J. Biol Chem.* 268:9886–9891 (1993)) with slight modifications. Various amounts of intact enzyme or enzyme fragments were added to 50 mM PBS, Ph 7.2, containing 15% fetal calf serum and 0.25 mmol of [$^{14}$C]N-acetyllactosamine ($4\times10^5$ dpm), 50 µg BSA and 0.02% $NaN_3$ in a volume of 60 µl. After incubation for a predetermined amount of time at room temperature, the reaction mixture was diluted to 1.0 ml with distilled water and applied to a column containing 1.0 ml Q-Sepharose equilibrated with water. Sialylated product was eluted with 1 M NaCl and quantified by scintillation counting.

Primary Neuronal Cultures

Cultures enriched in granule neurons were obtained from the cerebellum of 8-days-old Wistar rats (Charles River, Wilmington, Mass.) as described by D'Mello et al., *J. Neurosci* 17:1548–1560 (1997). Cells were plated in basal Eagle medium (BME, Gibco BRL, Gaithersburg, Md.), supplemented with 10% FCS, 25 mM KCl and 2 mM glutamine (Gibso BRL) on dishes coated with poly-L-lysine and laminin. Cytosine arabinofurnoside (10 µM) was added to the culture medium 18–22 hrs after plating to prevent replication of non-neuronal cells. Replacement of culture medium with serum-free BME medium was performed 7–10 days after plating. Cells were maintained in serum-free BME with 5 mM KCl for 3 hrs and challenged with different stimuli. Neuronal survival was assayed after 24 hours by staining with 10 µg/ml fluorescein diacetate (FDA, Sigma) (Jones and Senft, 1985) and with DAPI (see above). Chicken dorsal root ganglia neurons were prepared as described (Cox and Dunlap, *J. Gen. Physiol* 104:311–336 (1994)).

Immunodetection of Activated Akt

PC12 cells were deprived of serum for 24–48 hours, stimulated with TS, TS-F or LTR for 2, 5 or 10 minutes and immediately lysed with 2% SDS. In studies using the PI-3 kinase inhibitor, LY294002 (LY), cells were pre-treated with the inhibitor (1 µM) for 30 min prior to the addition of TS-F or TS. The proteins in the cell lysate were separated in SDS-10% polyacrylamide gels, transferred to nitrocellulose membrane (Bio-Rad) and the phosphorylated form of protein kinase Akt was detected with phospho-Akt (Ser 473) antibody (New England BioLabs, Beverly, Mass.), followed by alkaline phosphatase-conjugated secondary antibody (Promega, Madison, Wis.). Bands corresponding to phospho-Akt (60 kDa) were quantified using a scanning densitometer (Bio-Rad).

Results

TS Promotes Neurite Extension in PC12 and N18 Neuronal Cells

Undifferentiated PC12 and N18 cells extended multiple neurites when live T. cruzi trypomastigotes were added to the liquid overlay of the cultured cells. In addition, conditioned medium prepared by incubating live trypomastigotes in RPMI at 4° C. for 24 hours, also induced neurite outgrowth in both PC12 and N18 cells. Trypomastigote is a mobile, invasive form of *T. cruzi* that shuttles from the heart, GI tract, and other organs to the circulation, and from the circulation back to peripheral tissues and internal organs. Therefore, trypomastigotes and trypomastigote-secretory products can associate with, and modify the properties of, various cells and proteins throughout the body, including, for example, neurons and neurotrophic factors.

The trypomastigote-conditioned medium comprises TS, proteases such as cruzipain (Murta, A. C., et al, *Mol. Biochem. Parasitol.* 43: 27–38 (1990)), the adhesion molecule penetrin (Pereira, M., et al., *J. Exp. Med.* 174: 179–191 (1991)), and other factors thought to mediate *T. cruzi* infection (Pereira, M., in Russell, D. Ed., Bailliè re's Clinical Infectious Diseases, pp. 305–334, Bailliè re Tindall, London, (1994)). To identify the neurotrophic factor(s) present in the trypomastigote extract, purified preparations of proteins which are reported to mediate *T. cruzi* infection (e.g., TS, cruizipain, penetrin) were tested in the neurite outgrown assay. Of the proteins tested, only TS induced neurite outgrowth of both PC12 and N18 neuronal cells. TS induced neurite extension either as a soluble factor in the liquid overlay of the neuronal cell monolayers (FIGS. 2D and 2E) or as a ligand immobilized on the plastic substratum that served as support for cell attachment (FIG. 3A). In solution, TS was active at very low concentrations, namely, in the range of 0.125 nM (25 ng/ml to 200 ng/ml). PC12 neurites became visible 3 hours after a single dose of TS, and remained extended for about 24 hours.

Figure 2A:
FIG. 2A is a photomicrograph of PC12 cells cultured on collagen coated dishes for 16 hours in serum-free RPMI-1640/0.2% bovine serum albumin (BSA). The photomicrograph shows that PC12 cells do not extend neurites when cultured under these conditions. Magnification 400×.
Figure 2B:
FIG. 2B is a photomicrograph of PC12 cells cultured on collagen coated dishes for 16 hours in serum-free RPMI-1640/0.2% BSA supplemented with NGF (0.1 µg/ml). The photomicrograph shows that NGF induces neurite outgrowth in PC12 cells. Magnification 400×.
Figure 2C:
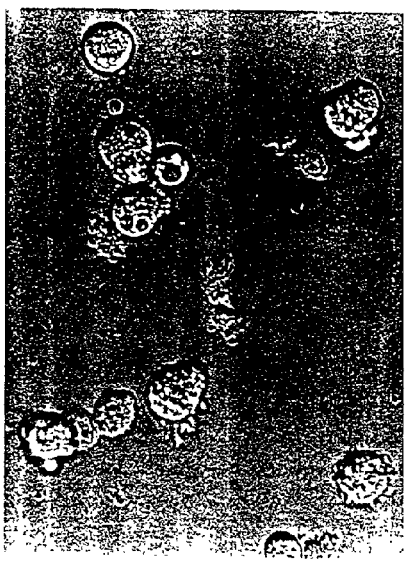
FIG. 2C is a photomicrograph of PC12 cells cultured on collagen coated dishes for 16 hours in serum-free RPMI-1640/0.2% BSA supplemented with *V. cholera* neuraminidase (VCNA)(2.4 µg/ml). The photomicrograph shows that VCNA does not induce neurite outgrowth in PC12 cells. Magnification 400×.
Figure 2D:
FIG. 2D is a photomicrograph of PC12 cells cultured on collagen coated dishes for 16 hours in serum-free RPMI-1640/0.2% BSA supplemented with TS (1 µg/ml). The photomicrograph shows that TS induces neurite outgrowth in PC12 cells. Magnification 400×.
Figure 2E:
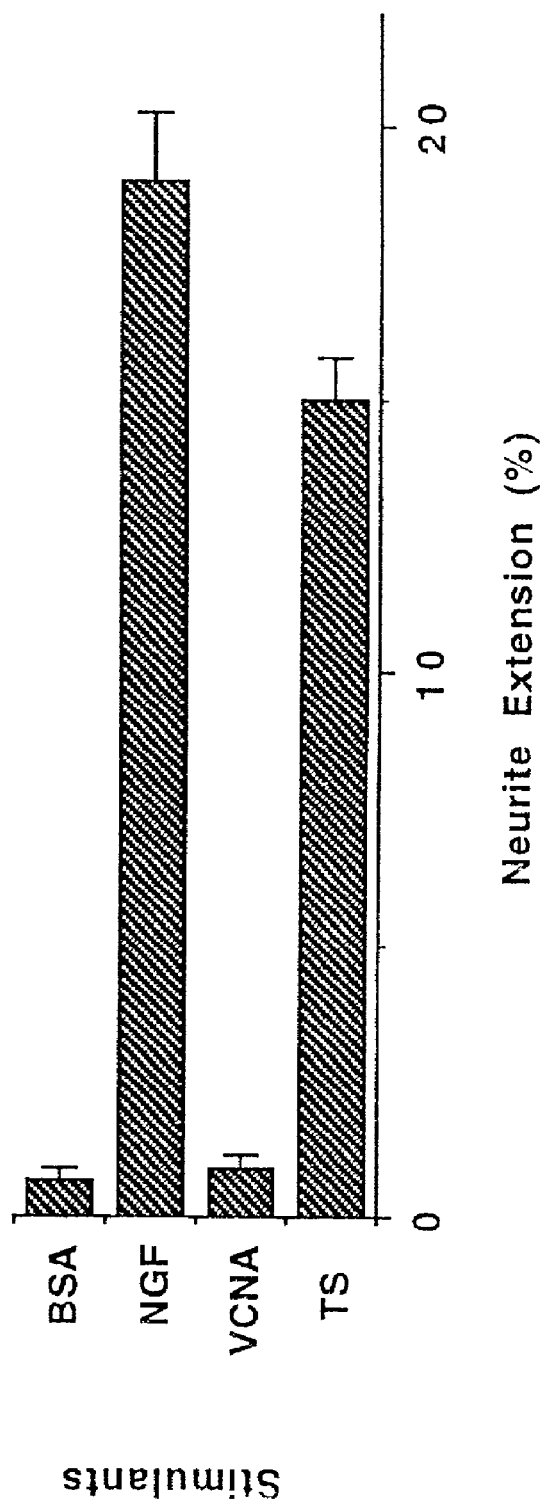
FIG. 2E is a graph showing that TS induces neurite outgrowth in PC12 cells. The graph presents data from triplicate samples of the cultures shown in FIGS. 2A–2D. The experiment was repeated more than ten times.

The neurotrophic action of TS was specific for the *T. cruzi* enzyme as cruzipain and penetrin did not induce neurite extension. Additionally, neuraminidases (sialidases) from other microbes, namely from the bacteria *Vibrio cholera* (VCNA), *Clostridium perfringens* and from the Newcastle disease virus did not induce neurite outgrowth (FIGS. 2C and 2E).

TS Protects PC12 Cells from Death Caused by Trophic Factor Deprivation and Induces the Expression of Bcl-2

Neurotrophic factors such as NGF and CNTF regulate the differentiation and maintenance of the nervous system, and are critical to the survival of neuronal cells. Depriving neuronal cells of neurotrophic factors results in the induction of programmed cell death or apoptosis (Deshmukh, M. and Johnson, E. M. Jr., *Mol Pharmacol.* 51: 897–906 (1997); Pettman, B. and Henderson, C. E. *Neuron* 20: 633–647 (1998)). PC12 cells maintain a neuronal phenotype when differentiated in the presence of NGF but undergo apoptosis if deprived of NGF (Rukenstein, A., et al., *J. Neurosci.* 11: 255202563 (1991); Mesner, P. W., et al., *J. Cell. Biol.* 119: 1669–1680 (1992)).

PC12 cells were culture in serum-free medium without and with various concentrations of TS to determine whether TS can rescue neurons from apoptotic death caused by trophic factor (NGF) deprivation. Apoptosis was assessed by counting the number of cells with internucleosomal DNA fragmentation after staining with DAPI (FIG. 4A) or with antibodies to free 3'-OH termini labeled with modified nucleotides (TUNEL assay (FIG. 4B)). TS effectively protected PC12 cells from apoptosis at concentrations in the low pM range under conditions in which the sialidase from *V. cholera* did not (FIGS. 4A, 4B and 5A). A concentration of TS as low as 62 pM (equivalent to 12.5 ng/ml) protected 45% of PC12 cells from death (FIG. 5A). Protection by a single dose of TS lasted up to several days (FIG. 5B).

TS Induces Bcl-2 Gene Expression in PC12 Cells

The members of the Bcl-2 family are key regulators of apoptosis in many types of mammalian cells, including neurons (Merry, D. E. and Korsmeyer, S. J., *Ann. Rev Neurosci.* 20: 245–267 (1997)). NGF promotes survival of PC12 cells by inducing overexpression of the anti-apoptotic Bcl-2 gene (Mah, S. P., et al., *J. Neurochem.* 60: 1183–1186 (1993)). To determine whether TS promotes neuron survival through a similar mechanism, Bcl-2 transcripts were quantified by RT-PCR in PC12 cells grown in serum-free medium with or without TS. TS at low concentrations dramatically increased Bcl-2 mRNA in the neuronal cells starved of mammalian neurotrophic factors, similar to the effect of NGF (FIG. 7). While not being bound by any particular theory, the data presented herein indicate that TS can protect PC12 cells from apoptosis by inducing the expression of the Bcl-2.

Identification of a TS Epitope that Induces Neurite Extension

The TS of trypomastigotes comprises a Cys-rich catalytic domain of 666 amino acids in the N-terminus and a long 12-amino acid tandem repeat domain in the C-terminus (Pereira, M. E. A., et al., *J. Exp. Med.* 174: 179–191 (1991)). To identify a region of the TS molecule that underlies neurite outgrowth, various nucleic acid constructs encoding poly-His -tagged fragments of TS (FIG. 3B) were generated by PCR. The constructs were expressed in *E. coli*, and the recombinant fragments of TS were purified by $Ni^{2+}$ chelate chromatography ($Ni^{2+}$-agarose) and tested in the neurite outgrowth assay. Fragment LTR, which corresponds to the C-terminal tandem repeat, did not induce neurite outgrowth in PC12 cells nor in neuroblastoma N18 cells (FIG. 3B). In contrast, enzymatically active fragment TS-F, which represents the full-length catalytic domain of TS, induced neurite outgrowth to about the same extent as the intact enzyme. However, the enzymatic activity of TS was not essential for neurite extension. Fragment TS-F-47, generated by deleting 47 amino acids from the N-terminus of fragment TS-F, was enzymatically inactive and yet as effective as the native enzyme in stimulating neurite outgrowth (FIGS. 3A and 3B). Also, the sequence of 188 amino acids at the C-terminus of the catalytic domain was not required for neurotrophic action, as deletion of this sequence from TS-F-47, generating fragment TS-CC-47, did not substantially reduce neurite outgrowth (FIGS. 3A and 3B).

In contrast, deletion of 21 amino acids from the C-terminus of TS-CC-47 produced fragment TS-Cat-47, which was inactive in stimulating neurite outgrowth (FIGS. 3A and 3B). Thus, the region of TS which consists of the 21 amino acid sequence that distinguishes TS-CC-47 from TS-Cat-47 confers neurotrophic activity upon the protein.

In further studies, the synthetic peptides presented in Table 1 were employed. Synthetic peptides CFN1 (SEQ ID NO:13) which comprises the C-terminal 21 amino acids of TS-CC-47, peptide C44 (SEQ ID NO:12) and the fourteen amino acid peptide C14 (SEQ ID NO:14) which are based on the sequence of the catalytic domain of TS had direct neurotrophic activity. These studies confirmed that carboxyl region of the catalytic domain is critical for neuotrophic activity (FIG. 3C).

Synthetic peptides based on other regions of TS, such as peptide TR (SEQ ID NO:19), derived from the tandem repeat (FIG. 3B), and peptide B2 (SEQ ID NO:18), based on a sequence upstream of peptide CFN-1 (FIGS. 3B and 3C), did not induce neurite outgrowth.

TS Synergizes with CNTF or LIF to Promote Survival of PC12 Cells

PC12 cells were cultured in serum-free medium without and with TS, alone or in combination with conventional neurotrophic factors, all at concentrations that produce modest or no neuroprotective response. TS was initially tested in combination with the neurotrophins NGF, brain-derived neurotrophic factor (BDNF) and NT-3 (Ip, N.Y. and Yancopoulos, G. D., *Annu. Rev. Neurosci.* 19: 491–515 (1996)). Such co-administration did not substantially increase neuron survival beyond the anticipated additive-effect of individual neurotrophic factors. For example, TS at 2.5 ng/ml and NGF at 0.5 ng/ml protected 15% and 18% PC12 cells from apoptotic death, respectively, whereas co-administration of TS and NGF at the same concentrations protected 35% of the PC12 cells. Such additive responses were observed when other concentrations of TS (5, 11.5 and 30 ng/ml) were co-administered with NGF (0.5 ng/ml), BDNF (2.0 ng/ml) or NT-3 (2 ng/ml).

The response of PC12 cells to the combination of TS with neurotrophic factors of the IL-6 family, namely IL-6, IL-11, CNTF, leukemia inhibitory factor (LIF), and oncostatin-M (OSM) (Ip and Yancopoulos, *Annu. Rev. Neurosci.*, 19:492–515 (1996)) was also assessed. While TS at 2.5 ng/ml promoted survival in 13% of PC12 cells grown in serum-free medium, co-administration of TS with a subthreshold concentration of CNTF (50 ng/ml) or LIF (0.5

TABLE 1

Synthetic Peptides Modeled on the TS Sequence.

| peptide | amino acid sequence | |
|---|---|---|
| C44 | QPLRRQRVVVVPLSPRLVLLAFCRQRLPLKRMGGSYRCVNASTAN | (SEQ ID NO:12) |
| CFN1 | $^{425}$RQRLPKRMGGSYRCVNASTAH$^{445}$ | (SEQ ID NO:13) |
| C14 | RQRLPKRMGGSYRC | (SEQ ID NO:14) |
| C19Y21 | GNASQNVWEDAYRCVNASTAN | (SEQ ID NO:15) |
| CYN2 | $^{425}$GNASQNYWEDAYRC$^{438}$ | (SEQ ID NO:16) |
| CYFN | $^{439}$VNASTAN$^{445}$ | (SEQ ID NO:17) |
| B2 | YSVDDGETWE | (SEQ ID NO:18) |
| TR | DSSAHGTPSTPA | (SEQ ID NO:19) |

Peptides C19Y21 and CYN2 are derived from the amino acid sequence of the protein encoded by clone 19Y (GenBank accession number AJ002174). Peptides C44, CFN1, C14 and TR are derived from the amino acid sequence of the protein encoded by clone 7F (GenBank accession number M61732). Peptides CYFN and B2 have amino acid sequences that are common to the proteins encoded by clone 19Y and 7F.

TS-derived recombinant fragments rescued PC12 cells from apoptotic death in a pattern similar to their neurite extension profile. Thus, fragments TS-F-47 and TS-CC-47 were active both in stimulating neurite outgrowth (FIG. 3A) and in preventing apoptosis of PC12 cells (FIG. 6A), whereas fragment TS-Cat-47 did not promote neurite outgrowth (FIG. 3C) as well as it promoted the survival of the PC12 cells (FIG. 6B). Control peptides B2 (SEQ ID NO:18) and TR (SEQ ID NO:19), did not promote neurite outgrowth (FIGS. 3B and 3C) nor survival of the PC12 cells (FIG. 6B).

ng/ml) dramatically increased neuron survival to 61% and 45%, respectively (FIG. 8A). Human CNTF and recombinant human and rat CNTF were equally effective in potentiating the TS action of PC12 cells. TS/CNTF and TS/LIF synergism was also observed in the neurite outgrowth assay. Dose-response experiments revealed that the synergism of TS with CNTF or LIF in promoting neuron servival was most remarkable at subthreshold or threshold concentrations of TS (FIGS. 8B and 8D). Confirmation of the synergism between the trypanosomal protein and CNTF was provided by analysis of expression of the Bcl-2 gene in PC12 cells. Bcl-2 transcripts increased by ~3–4-fold in the PC12 cells treated with the combination of TS and CNTF, relative to the Bcl-2 transcript in the cells treated with only one of the proteins at the same concentration (FIG. 8C). These results demonstrate that TS can promote survival of PC12 cells by upregulating Bcl-2 expression.

TS Inhibits Serum Withdrawal-induced Apoptosis of Schwann Cells

Immortalized Schwann cells (Rambukkana, et al., *Science*, 282:2076–2079 (1998)) were cultured in DMEM supplemented with 10% fetal calf serum (DMEM/10%FCS). For the apoptosis assay, the cells were plated on 16 well slides in DMEM/10%FCS and cultured overnight. The cells were then washed three times with serum-free DMEM and cultured in serum-free DMEM or in serum-free DMEM supplemented with TS (final concentration 0.5 µg/mL, 1 µg/mL, 2 µg/mL or 3 µg/mL). After culture for 24, 48 or 72 hours, the cells were fixed in 4% formaldehyde in PBS for 10 minutes, washed with PBS and stained with DAPI (5 mg/mL). The cells were then washed with PBS and cells with fragmented (apoptotic) nuclei were quantified by visualization under UV light using a fluorescence microscope. 300–400 cells were examined to determine the percentage of apoptotic cells.

TS effectively inhibited serum withdrawal-induced apoptosis of Schwann cells in the assay (FIG. 9).

TS Protects Primary Rat Cerebellar Granule Neurons from Apoptosis

Cultured primary cerebellar granule neurons die of apoptosis when switched from a medium containing an elevated concentration of $K^+$ (25 mM) to a medium containing a lower $K^+$ level (5 mM) (D'Mello et al., *Proc. Natl. Acad. Sci. U.S.A.*, 90:10989–10993 (1993)). Death caused by such potassium depolarization can be prevented by several growth factors such as NGF and insulin-like growth factor (IGF-1) (D'Mello et al., *Proc. Natl. Acad. Sci. U.S.A.*, 90:10989–10993 (1993)) The neuroprotective effects of TS were assessed in cultures of primary cerebellar granule neurons in apoptosis-causing low $K^+$ medium supplemented with TS. Neuron viability was ascertained by phase-contrast microscopy (FIGS. 10A–10C) and fluorescent microscopy after staining viable cells with fluorescein diacetate (FIGS. 10D–10F) (Jones and Senft, *J. Histochem. Cytochem.*, 33:77–79 (1985); D'Mello et al., *J. Neurosci* 17:1548–1560 (1997)). In agreement with established results (D'Mello et al., *J. Neurosci* 17:1548–1560 (1997)), survival of primary cerebellar granule neurons in 5 mM KCl medium (FIGS. 10A, 10D and 10G) was poor relative to survival in 25 mM $K^+$ (FIGS. 10C, 10F and 10G). Addition of TS to the apoptosis-causing low $K^+$ medium effectively protected the neurons from death, demonstrating that TS provides neurotrophic support for primary neurons.

Reversal of TS-Induced Neuroprotection by Inhibitors of the Phospholinositide-3 Kinase (PI-3 Kinase)

Induction of survival in PC12 cells by NGF, or in cerebellar granule cells by IGF-1 requires signaling through PI-3 kinase, as demonstrated by the use of specific pharmacologic inhibitors (Yao and Cooper, *Science*, 267:2003–2006 (1995); D'Mello et al., *J. Neurosci* 17:1548–1560 (1997)). Wortmannin inhibits PI-3 kinase both in vitro and in vivo (Ui et al., *Trends Pharmacol* 20:303–307 (1995)). Addition of wortmannin to PC12 cells maintained for 24 hrs in serum-free medium supplemented with TS-F, the catalytic domain of TS, reduced neuronal viability in a dose-dependent manner (FIG. 11A). This reversal was quantitatively similar to the inhibition of NGF-induced neuroprotection in PC12 cells, as previously reported (Yao and Cooper, *Science*, 267:2003–2006 (1995)).

Wortmannin also reversed protection against apoptosis induced by the co-administration of TS-F and CNTF, although to a lesser extent than that of TS-F alone (FIG. 11A). For example, when PC12 cells were co-treated with wortmannin (200 mM) and TS-F or TS-F+CNTF, neuronal viability was 57±2% and 80±3% of that observed with TS-F or TS-F+CNTF without wortmannin, respectively (FIG. 11A). Because CNTF signaling does not appear to require PI-3 kinase activation (Inoue et al., *Mol. Neurobiol*, 12:195–209 (1996)), the reduced efficiency of wortmannin to inhibit neuroprotection produced by the TS-F+CNTF combination, compared to TS-F alone, is consistent with the view that TS signaling in PC12 cells requires PI-3 kinase activation. In addition, in agreement with published results (Zhong et al., *Brain Res.*, 661:56–62 (1994)), we found that CNTF by itself produced little, if any, protection of PC12 cells from undergoing apoptosis in serum-free medium (FIG. 11A).

The inhbition of TS-F-induced neuroprotection by wortmannin was confirmed by experiments with LY294002, another PI-3 kinase inhibitor (Vlahos et al., *J. Biol. Chem.*, 269:5241–5248 (1994)). LY294002 induced apoptosis in PC12 cells maintained in TS-F or NGF in a concentration range (FIG. 11B) similar to the one effective in causing death of IGF-1-stimulated cerebellar granule neurons (D'Mello et al., *J. Neurosci* 17:1548–1560 (1997)). As with wortmannin, LY294002 was less effective in reversing the protection of TS-F +CNTF than of TS-F only (FIG. 11B).

TS Activates Protein Kinase Akt in Neuronal Cells

Treatment of TS-stimulated PC12 cells with the PI-3 kinase inhibitors wortmannin and LY294002 induced apoptosis (FIGS. 11A and 11B), suggesting that PI-3 kinase may play an important role in TS-induced cell survival. Lipid products of PI-3 kinase activity directly activate the serine/threonine kinase Akt, which then becomes phosphorylated at threonine-308 and serine-473 by the protein kinase PDK1 and an unknown kinase, respectively (Franke et al., *Cell*, 81:727–736 (1995), for reviews see Franke et al., *Cell* 88: 435–437 (1997); Downward, *Curr. Opin. Cell Biol.* 10:262–267 (1998)). Activated Akt phosphorylates the Bcl-2 family member BAD and the Forkhead transcription factor, leading to cell survival (Datta et al., *Cell*, 91:231–241 (1997); Brunet et al., *Cell* 96:857–868 (1999)).

Thus, if TS activates PI-3 kinase signaling pathway to promote survival, then the TS action on PC12 cells should result in the stimulation of Akt kinase. To determine whether Akt is activated in response to TS, we used an antibody specific for the Akt serine-473 epitope to detect activated Akt in TS-stimulated PC12 cells. The immunoblot displayed in FIG. 11C shows that Akt becomes activated after brief (2–5 min) exposure of PC12 cells to TS. The extent of TS-dependent Akt phosphorylation was similar to the phosphorylation produced by 20% fetal calf serum. The catalytic domain of TS (fragment of TS-F) was effective in activating Akt, whereas the C-terminal tandem repeat LTR fragment was not (FIG. 11D), consistent with PC12 cell survival being induced by TS-F, but not LTR. Furthermore, the PI-3 kinase inhibitor LY294002 completely blocked TS-F-induced Akt phosphorylation (FIG. 11D), consistent with a role for a TS-dependent PI-3 kinase activation of Akt, and analogous to the PI-3 kinase/Akt kinase activation by NGF, PDGF, IL-3 and other growth factors (Franke et al., *Cell* 88: 435–437 (1997); Downward, *Curr. Opin. Cell Biol.* 10:262–267 (1998)).

Discussion

The studies presented herein, demonstrate that TS can provide trophic support for neurons and glial cells (e.g., Schwann cells). Importantly, TS effectively supported the development and survival of neurons at low pM concentrations (FIGS. 3A, 4 and 5). In fact, TS was more potent on a molar basis then mammalian neurotrophic factors, such as NGF (FIG. 5). Such effective concentrations of TS can easily be achieved in vivo by administration of the protein. TS-modeled recombinant polypeptides and synthetic peptides which do not have neuraminidase/sialyltransferase catalytic activities were also found to be neurtrophic, clearly demonstrating that the neurotrophic activity of TS is not due to the catalytic activity of the protein.

The neurotrophic activity of TS, a trypanosome protein, can synergize with mammalian neurotrophic factors. Trophic support can be provided by co-administering TS and a mammalian neurotrophic factor (e.g., CNTF, LIF) at concentrations below the effective concentration of each factor when administered individually. Thus, co-administration of synergistic amounts of TS and a mammalian neurotrophic factor can provide effective trophic support with significantly reduced or no undesirable side effects.

TS can provide neurotrophic support for neurons directly and/or indirectly. The capacity of TS to protect PC12 cells form apoptosis was affected by the activity of phosphatidylinositol-3 kinase (PI-3 kinase). Similarly, the neuroprotective activity of NGF in PC12 cells (Yao, R. and Cooper, G. M., *Science* 267: 2003–2006 (1995)) and of insulin-like growth factor (IGF) in cerebellar granule neurons (D'Mello et al., *J. Neurosci* 17:1548–1560 (1997)) requires phosphatidylinositol-3 kinase (PI-3 kinase). Thus, TS may bind to a neurotrophic surface receptor which activates a PI-3 kinase-dependent signaling pathway, as do NGF and IGF. In addition, TS potently and specifically induced IL-6 secretion in human intestinal microvascular endothelial cells and peripheral blood mononuclear cells and in mouse splenocytes. It is well established that IL-6 promotes survival of various types of neurons, including primary cultures of sympathetic neurons and PC12 cells (Marz, P., et al., *Proc. Natl. Acad. Sci* (*USA*) 95: 3251–3256 (1998)). In addition, IL-6 can synergize with NGF and other neurotrophic factors to promote neuron survival and differentiation (Wu, Y. Y. and Bradshaw, R. A., *J. Biol. Chem.* 271:13033–13039 (1996)). IL-6, like CNTF and other IL-6 family members, promotes differentiation and survival of neurons, not by activating the PI-3 kinase pathway, but by triggering the Janus kinase (JAK)/signal transducer and activator of transcription (STAT) signaling pathway (Nakashima, K. and Taga, T., *Semin. Hematol.* 35: 210–221 (1998)). The possible convergence of various signaling pathways, whether activation of the PI-3 kinase, or synergism with CNTF, or indirectly through IL-6, is consistent with the exquisite sensitivity of PC12 cells to the neurotrophic action of TS.

The studies presented herein demonstrate that TS, active fragments and active peptides thereof can be used to provide trophic support for neurons in a mammal. The studies also provide an explanation for the existence of many TS family members which lack both neuraminidase and trans-sialidase activities (Uemura. J., et al., *EMBO J.* 11: 3837–3844 (1992); Parodi, A. J., et al., *EMBO J.* 11: 1705–1710 (1992)) some of which are found on multiple *T. cruzi* chromosomes (Henriksson, J., et al., *Mol. Biochem. Parasitol* 42: 213–224 (1990)). These proteins may function as neurotrophic factors which prevent destruction of the host's neurons and subsequent death of the host. This strategy would provide *T. cruzi* with additional opportunities to infect reduviid bugs feeding on the infected host, thereby completing the parasitic life cycle.

Example 2

*T. cruzi* infection, TS and Peptides Derived from TS Promote Survival of Human Schwann Cells The following materials and methods were used:

Cell Culture

Immortalized human Schwann cells (Rambukkana, A. et al., *Science*, 282:2076–2079 (1998)) were maintained in DMEM supplemented with 10% FCS, 0.5 mM pyruvate Na (Gibco) and 0.1 mM nonessential amino acids. Vero cell monolayers were grown at 37° C. in DMEM with 2.5% FCS, 100 U/ml penicillin and 100 μg/ml streptomycin in humidified chambers, as previously described (Pereira, M. E. A. et al., *Infect. Immun.*, 64:2884–3892 (1996)).

Parasites

*T. cruzi* trypomastigotes, Silvio strain, were maintained in Vero cell cultures, as described earlier (Pereira, M. E. A. et al., *Infect. Immun.*, 64:2884–3892 (1996)). Trypomastigotes were collected 5 days after the start of infection and immediately used to infect Schwann cells. *T. cruzi* epimastigotes were grown in acellular LIT medium at 26° C. for 5–10 days (Saavedra, E. et al., *J. Exp. Med.*, 190:1825–1836 (1999)).

For infection assays, Schwann cell monolayers were infected with *T. cruzi* at $2 \times 10^5$ parasites/ml. After 2 hr, most swimming parasites were removed by washing and the cell monolayers were switched to serum-free medium for 72 hr. Intracellular parasites were identified after staining with Giemsa or by indirect immunofluorescence using chagasic IgG as primary antibody and Alexa 594-labeled second antibody, as described earlier (Ming, M. et al., *Cell*, 82:287–296 (1995)). Isolation of $TS^+$ and $TS^-$ trypomastigotes was based on the use of magnetic beads containing immobilized monoclonal antibody (mAb TCN-2) specific for the C-terminus tandem repeat of TS, as described earlier (Meciano Filho, J. et al, *Gerontology*, 41:18–21 (1995)). $TS^+$ parasites were eluted from the beads with synthetic peptide hapten while the TS parasites were obtained by negative selection. The isolated sub-populations were checked for their specific TS activities and immediately used in infection and Akt assays.

*Leishmania major* promastigotes, strain Friedlin VI, (MHOM/IL/80/Friedlin) transfected with pXG1a and pXG1a-TS are clones L1D4-vector and L1D4-TS, respectively, as described earlier (Belen Carrillo, M. et al., *Infect. Immun.*, 68:2728–2734 (2000)); they were maintained at 26° C. in Mβ199 medium (Gibco) supplemented with 10% FCS. For Akt activation experiments, trypomastigotes and epimastigotes of *T. cruzi*, and promastigotes of *L. major* were washed 3× with serum-free DMEM and applied to monolayers of Schwann cells for predetermined periods of time.

Purification of TS and TSA-1

TS was isolated from supernatants of Vero cells infected with *T. cruzi* by immuno-affinity chromatography as described in Example 1. The purified TS yielded a doublet of MW 200 kDa as determined by Coomassie-stained polyacrylamide gels (Scudder, P. et. al., *J. Biol. Chem.* 268: 9886–9891(1993)). The recombinant catalytic domain of TS, CD (also referred to as TS-F or ΔTS), expressed in *E. coli* was purified by metal chelate and anion exchange chromatography as described in Example 1. CD derived from clone 19Y was used in the Schwann cell studies. LTR and TS-F-47 fragments of TS were isolated from engineered insect cells and bacteria, respectively, as described in Example 1.

TS enzymatic activity was measured by the sialylation of the acceptor $^{14}$C-labeled N-acetyllactosamine on anion exchange resins (Scudder, P. et. al., *J. Biol. Chem.* 268: 9886–9891 (1993)). Recombinant TSA-1, was expressed on insect sf9 cells and purified from serum-free medium by ion exchange chromatography (monoQ) and preparative SDS-PAGE (Wrightsman, R. A. et al., *J. Immunol.,* 153:3148–3154 (1994).

Identification of Apoptotic Nuclei

Schwann cells were plated to 70% confluency in 16-well chamber slides (LabTek) in DMEM with 10% FCS. After overnight incubation at 37° C., medium was changed to serum-free DMEM without or with TS or other test compounds. Cells were fixed for 24–72 hours later with 1% paraformaldehyde overnight at 4° C. and stained with 4',6-diamidino-2-phenylindole (DAPI), 2 µg/ml in PBS, pH7.2, for 2 min. For quantification, normal, condensed and fragmented nuclei in 10 randomly chosen fields and accounting more than 400 cells were counted at ×40 magnification in triplicate samples, in a minimum of 3 assays.

Immunodetection of Activated Akt

Schwann cells, grown in 10% FCS to 70% confluency in 6-well plates, were switched to DMEM containing 0.1% FCS for 48 hours to reduce basal Akt phosphorylation. Then the cells were placed in serun-free DMEM medium for 2 hours and challenged with TS, CD or other test factors for predetermined periods of time. When the PI-3 kinase inhibitor LY294002 (Sigma) was used, the inhibitor was added to the serum-starved cells 30 minutes before challenge with TS or CD. Cell samples were lysed with lysis buffer (20 mM Tris, pH7.5, 150 mM NaCl, 1 mM EDTA, 1% Triton X-100 (t-Octylphenoxypolyethoxyethanol), 2.5 mM sodium pyrophosphate, 1 mM glycerophosphate, 1 mM Na$_3$VO$_4$, 1 µg/ml leupeptin and 1 mM Phenymethylsulfonyl fluoride (PMSF)). Samples (40 µg) were run on 10% SDS-Page, blotted to nitrocellulose paper and analyzed by Western (immuno) blot with monoclonal antibody specific for P-Ser473 of Akt (New England Biolabs). Reaction was visualized by chemiluminescence using the ECL kit (New England Nuclear).

Kinase Assay of Akt in vitro

Enzymatic activity of Akt kinase was assessed using the synthetic substrate GSK-3α-fusion protein (Cell Signaling Technology, Beverly, Mass.), according to the protocol provided by Cell Signaling Technology. In short, lysates of Schwann cells subjected to various treatments were immunoprecipitated with Akt antibody coupled to agarose beads, and the immunoprecipitates incubated with GSK-3α-fusion protein as the substrate for Akt phosphorylation, in the presence of 200 µM ATP. Phosphorylation of GSK-3 fusion protein was detected by Western blot using phospho-GSK-3αβ (Ser21/9)-specific antibody (Cell Signaling Technology). The reaction product was identified by chemiluminescence using the ECL kit (New England Nuclear).

Generation of Stabel Tetracycline-regulated AktKI/GFP and Transient PTEN Transfectants A plasmid encoding the hemagglutinin (HA)-tagged Akt rendered kinase inactive (AktKI) by a mutation in its ATP binding site (K179M), was a provided by Drs. Alfonso Bellacosa (Fox Chase Cancer center, Philadelphia) and Lewis Cantley (Beth Israel Hospital, Harvard Medical School) (Skorski, T. et al., *EMBO J.,* 16:6151–6161 (1997)). The plasmid pTR5-AktKI/GFP was constructed by subcloning AktKI into the PmeI site of the tetracycline-regulated dicistronic expression plasmid pTR5-DC/GFP (Mosser, D. D. et al., *Biotechniques,* 22:158–161 (1997)). To generate cells expressing the tetracycline-regulated transactivator protein tTA, which allows control of gene expression by tetracycline, Schwann cells were transfected with PtTA-Hygro using SuperFect™ transfection reagent (Qiagen, Valencia, Calif.) and selected for hygromycin B resistance, as described (Hall, B. S. et al., *Mol. Biol. Cell,* 11:153–160 (2000)). Positive cells were isolated by fluorescent-activated cell sorting (FACS) after transfection with pTR-GFP, an expression plasmid encoding green fluorescence (GFP) under the control of the tet operator. These cells were co-transfected with pTR5-AktKI/GFP and pCDNA3 and selected for neomycin resistance in the presence of 1 µg/ml Geneticin (Life Technologies). In addition, 50 ng/ml tetracycline was included in the medium to prevent expression of AktKI during selection. Cells expressing AktKI and GFP were selected by removal of tetracycline followed by FACS. Cells were maintained in medium containing 10% FCS and 50 ng/ml tetracycline and transferred to tetracycline-free medium 24 hr (or otherwise indicated) before assay.

The plasmids pCDNA3-PTEN and pCDNA3-G129R encoded wild type PTEN and phosphatase-inactive mutant of PTEN, respectively (Furnari, F. B. et al., *Proc. Natl. Acad. Sci. USA,* 94:12479–12484 (1997), Myers, M. P. et al., *Proc. Natl. Acad. Sci. USA,* 94:9052–9057 (1997)). Schwann cells were seeded in 10% FCS to 50–70% confluency in 10 cm Petri dishes 24h prior transfection, performed in serum-free DMEM. Cells were maintained in 10% FCS for 24 hr and then switched to medium containing 700 µg/ml G418 (Gibco BRL) and 2% FCS for 3 days and 0.1% FCS for another 4 days with CD added to some cell monolayers. After this cells were assessed for viability by Trypan blue exclusion and by DAPI staining. At the same time cell lysates were analyzed for Akt phosphoryltion by Western (immuno) blots with monoclonal antibody specific for P-Ser473 of Akt (New England Biolabs). Reaction was visualized by chemiluminescence using the ECL kit (New England Nuclear).

Results

*T. cruzi* Invasion Blocks Apoptosis of Schwann Cells:

Little cell death (<1%; detected by nuclear staining with DAPI) was detected in cultures of immortalized Schwann cells that were maintained in medium containing 2% FCS for 72 hours. However, immortalized Schwann cells underwent apoptosis in a time-dependent manner when cultured in medium devoid of serum. About 50% of cells in such cultures contained fragmented (apoptotic) nuclei by 72 hours (FIG. 19, bar labeled "Non-Inf"). Primary cultures of rat Schwann cells are reported to have similar susceptibility to cell death induced by serum-withdrawal (Delaney, C. L. et al., *Neurobiol.,* 41:540–548 (1999); Weiner, J. A. and Chun, J., *Proc. Natl. Acad. Sci.,* 96:5233–5238 (1999); Campana, W. M. et al., *J. Neurosci. Res.,* 57:332–341 (1999)).

To further study the survival-promoting effect of *T. cruzi*, Schwann cell monolayers were exposed to tryopmastigotes (the infective stage of *T. cruzi*) for about two hours, after which most of the swimming parasites were removed by washing. The resulting infected monolayers and non-infected monolayers were cultured for 72 hours in media that did not contain serum. Under the assay conditions used, about 23±3% of Schwann cells harbored intracellular *T. cruzi* (amastigotes). This rate of infection is similar to the rate of infection reported for myocytes (Hall, B. S. et al., *Mol. Biol Cell,* 11:153–160 (2000)). Inspection of the resulting monolayers using phase contrast microscopy revealed that Schwann cells in the infected monolayers looked more viable than cells in the non-infected monolayers, as assessed by cell detachment from the substratum, membrane blebbing, and cellular extensions. The infected Schwann cell monolayers were further analyzed by staining with DAPI and with chagasic IgG which were employed to detect apoptotic nuclie and intracellular infection (Ming, M. et al., Cell, 82:287–296 (1995)), respectively. This analysis revealed an inverse correlation between the proportion of Schwann cells with fragmented nuclei and Schwann cells with intracellular *T. cruzi* (FIG. 19). Virtually all Schwann cells that contained intracellular parasites did not exhibit apoptotic nuclei despite being starved for 3 days in serum-free medium. In contrast, a high proportion of Schwann cells that were not infected with *T. cruzi* had apoptotic nuclei (FIG. 19). These data demonstrate that *T. cruzi* invasion protects Schwann cells against apoptosis induced by serum starvation.

Invasive, but Not Noninvasive, *T. cruzi*, Enhance Activation of Akt Kinase in Human Schwann Cells:

To determine whether *T. cruzi* exploits the Akt kinase to protect Schwann cells against apoptosis, monolayers of Schwann cells maintained in serum-free medium were exposed to trypomastigotes or epimastigotes, which are invasive and noninvasive stages of *T. cruzi*, respectively. After 10 minutes of exposutre, parasites that were not attached to the monolayers were removed by washing, the cells were lysed in lysis buffer, and the resulting lysates were analyzed for the presence of phosphorylated Akt kinase (phosphorylated on Ser-473) by immunoblotting (Datta, S. R. et al., Genes Dev., 13:2905–2927 (1999)). The results of the immunoblotting studies clearly showed that invasive trypomastigotes (Tryps) potently activated Akt kinase in a dose-dependent manner, while noninvasive epimastigotes (Epis) did not detectably activate Akt (FIG. 20A) under similar conditions.

Trypomastigotes consist of two morphologically similar sub-populations, TS$^+$ and TS$^-$, which have remarkably contrasting abilities to invade cells, with the former being strongly, and the latter weakly invasive for mammalian cells (Pereira, M. E. A. et al., Infect. Immun., 64:3884–3892 (1996), Saavedra, E. et al., J. Exp. Med., 190:1825–1836 (1999)). The TS$^+$ and TS$^-$ sub-populations differ in expression of surface-located *T. cruzi*-specific ligand, enzyme trans-sialidase, TS (Schenkman, S. et al., Annu. Rev. Microbiol., 48:499–523 (1994)). To determine if trypomastigote-induced activation of Schwann cell Akt kinase is restricted to the subpopulation of parasites with enhanced invasiveness and TS expression (i.e., TS$^+$ parasites), the generation of phosphorylated Akt in Schwann cells infected for 20 minutes with unfractionated trypomastigotes or with trypomastigotes of the TS$^+$ or TS$^-$ phenotypes was monitored. The strongly invasive TS$^+$ trypomastigotes were more potent in activating Akt kinase than unfractionated trypomastigotes (FIGS. 20B and 20C), of which only 20–30% of organisms are of the TS$^+$ phenotype (Pereira, M. E. A., et al., Infect. Immun., 64:3884–3892 (1996), Saavedra, E. et al., J. Exp. Med., 190:1825–1836 (1999)). On the other hand, infection of Schwann cells with noninvasive TS$^-$ trypomastigotes did not activate Akt kinase under the same conditions (FIGS. 20A and 20B). These results demonstrate that *T. cruzi* invasion of Schwann cells can lead to activation of Akt kinase.

TS, Through its Catalytic Domain, is a Potent, Specific Survival Factor for Schwann Cells and an Activator of PI3K/Akt Kinase Signaling.

The results of the infection studies with TS$^+$ and TS$^-$ trypomastigotes and of the studies described in Example 1, indicated that the *T. cruzi* sialidase is a ligand that promotes survival and activation of PI3K/Akt in Schwann cells. Therefore, TS purified from *T. cruzi* TS was tested for the capacity to inhibit apoptosis of Schwann cells induced by serum starvation. The addition of TS to Schwann cells subjected to serum starvation promoted survival of the cells and activated PI3K/Akt signaling at a dose as low as 100 ng TS per milliliter of medium (0.5 nM TS). Furthermore, a bacterially-expressed N-terminal fragment of TS consisting of the catalytic domain (CD; residues 33–666 of SEQ ID NO:2) protected Schwann cells against apoptosis (FIG. 21A) in a time- and dose-dependent manner (FIG. 21B), while the counterpart C-terminal long tandem repeat (LTR) did not promote Schwann cell survival nor activate PI3K/Akt signaling. Therefore, the catalytic domain of TS is the domain of the protein which has survival promoting activity for Schwann cells. Similarly, the catalytic domain (CD) was the moiety of TS that promoted the survival of PC12 cells (Example 1).

Strikingly, the presence of CD at 500 ng/ml (6 nM) in serum-free DMEM was nearly as effective in protecting Schwann cells from apoptosis as 2% serum (FIG. 21A). This result underscores the potency of TS as a survival factor for Schwann cells.

In addition, CD rapidly (within 1–5 min) and transiently (phospho-Akt not detected after 15 min) activated Schwann cell Akt kinase (FIG. 22A). Ly294002, a selective inhibitor of PI3K (Vlahos, C. J. et al., J. Biol. Chem., 269:5241–5248 (1994)), blocked CD-induced Akt activation (FIG. 22B) and inhibited TS-induced survival of serum starved Schwann cells (FIG. 22C), indicating that TS induces phosphorylation of Akt kinase via activation of upstream PI3K.

A *T. cruzi* surface antigen, TSA-1, that belongs to the TS superfamily (Chuenkova, M. et al., Biochem. Biophys. Res. Commun., 262:549–556 (1999)) (FIG. 3B, insert), did not protect Schwann cells against apoptosis (FIG. 21A), nor did it activate Akt kinase under the conditions TS and its catalytic domain did. These results emphasize the specificity of the anti-apoptotic action of TS.

Heterologous Expression of TS in *Leishmania major* Converts the Otherwise Inactive Parasites into Activators of Akt Kinase in Schwann Cells.

*L. major* is a protozoan parasite that selectively invades macrophages and cause cutaneous leishmaniasis worldwide. *L. major*, unlike *T. cruzi*, does not express TS (Belen Carrillo, M. et al., Infect. Immun., 68:2728–2734 (2000)). However, *L. major* transfected with the constitutive expression vector pXG1a containing the full-length coding region of TS (pXG1a-TS), produces a recombinant surface-located protein with enzymatic (FIG. 23B), immunological, and virulence-enhancing activities similar to the endogenous *T. cruzi* enzyme (Belen Carrillo, M. et al., Infect. Immun., 68:2728–2734 (2000)). Therefore, human Schwann cells were co-cultured with *L. tropica* that were transfected with pXG1a-TS and expressed *T. cruzi* TS or with *L. tropica* that were transfected with the empty vector (PXG1a). Co-culturing Schwann cells with *L. tropica* that did not express TS (*L. tropica* transfected with vector pXG1a) did not result in detectable activation of Schwann cell Akt kinase (FIG. 23A). However, Schwann cell Akt kinase was activated in co-cultures that contained *L. tropica* that expressed *T. cruzi* TS (FIG. 23A). These results further establish that TS is a trigger of PI3K/Akt signaling in human Schwann cells.

TS Does Not Promote Survival of Schwann Cells whose PI3K/Akt Signaling is Inactivated To further investigate the link between TS-induced survival of Schwann cells and the PI3K/Akt signaling pathway, Schwann cells capable of inducible expression of a kinase-inactive, dominant negative mutant, of Akt (HA-Akt (K179M); also referred to as AktKI) were used (Skorski, T. et al., EMBO J., 16:6151–6161 (1997)). To produce such cells, Schwann cells were transfected with ptTA-hygro a plasmid encoding a tetracycline-regulated transcriptional activator (tTA) (Mosser, D. D. et al., *Biotechniques*, 22:158–161 (1997); Hall, B. S. et al., *Mol. Biol. Cell*, 11:153–160 (2000)). Following selection, cells transfected with ptTA-hygro were transfected with pTR5-GFP and pTR5-AktKI/GFP (expression plasmids that encoded green fluorescent protein (GFP) and AktKI +GFP, respectively in a dicystronic cassette under the control of a promoter containing the tet operator sequence). Stable transfectants exhibited tetracycline-repressible AktKI and GFP expression as determined by immunoblot and fluorescence, respectively. AktKI-expressing Schwann cells (grown in medium without tetracycline) exhibited apoptotic morphology even in serum-containing medium, while counterpart Schwann cells transfected with GFP alone did not.

Akt immunoprecipitated from AktKI transfectants grown in medium without serum (to induce apoptosis) and tetracycline (to induce expression of AktKI and GFP) exhibited dramatically low background kinase activity towards GSK-3α substrate, relative to kinase activity of Akt immunoprecipitated from Schwann cells transfected with GFP alone (FIG. 24A). Furthemore, serum-starved AktKI-transfected Schwann cells exhibited higher levels of apoptosis than counterpart Schwann cells transfected with GFP alone (FIG. 24B). These findings demonstrate the dominant negative action of AktKI, and further demonstrate that Schwann cell survival depends on PI3K/Akt signaling (Delaney, C. L. et al., *Neurobiol.*, 41:540–548 (1999); Weiner, J. A. and Chun, *J. Proc. Natl. Acad. Sci.*, 96:5233–5238 (1999); Campana, W. M. et al., *J. Neurosci. Res.*, 57:332–341 (1999)).

Whether CD could inhibit serum starvation-induced apoptosis of Schwann cells expressing the dominant negative AktKI was also investigated. The addition of CD to serum-starved AktKI-transfected Schwann cells did not increase survival of the cells. However, the addition of CD to serum-starved control Schwann cells transfected with GFP vector (FIG. 24B) did increase survival of the cells. The inability of CD to promote survival of Schwann cells that over expressed dominant negative AktKI was accompanied by a similar inability of CD to enhance endogenous Akt enzymatic activity, contrary to the stimulation of Akt activity in control GFP-transfected Schwann cells (FIG. 24A).

To further establish the relationship between TS-induced survival and activation of PI3K/Akt in Schwann cells, Schwann cells that overexpressed the PI3K antagonist PTEN (Cantley, L. and Neel, B. G., *Proc. Natl. Acad. Sci. USA*, 96:4240–4245) were used. PTEN dephosphorylates the 3 position of phosphoinosites generated by PI3K and thus downregulates activation of Akt, and consequently, Akt-dependent cell survival (Furnari, F. B. et al., Proc. Natl. Acad. Sci. USA, 94:12479–12484 (1997); Wu, X. et al., *Proc. Natl. Acad. Sci. USA*, 95:15587–15591 (1998); Cantley, L. and Neel, B. G., *Proc. Natl. Acad. Sci. USA*, 96:4240–4245).

The addition of CD to Schwann cells transfected with PTEN did not result in the generation of phospho-Akt (FIG. 25A), and did not rescue cells from apoptotic death (FIG. 25B). In contrast, CD boosted levels of phospho-Akt and decreased the number of fragmented nuclei by about ten-fold in serum-starved Schwann cells transfected with empty vector (neo) (FIGS. 25A and 25B). Moreover, Schwann cells transfected with a dominant negative mutant of PTEN (pG129R) (Furnari, F. B. et al., *Proc. Natl. Acad. Sci. USA* 94:12479–12484 (1997)) had an extremely high background of phosphorylated Akt and a low degree of apoptotic nuclei relative to control cells transfected with empty pCDNA3 vector (neo) (FIGS. 25A and 25B). However, CD did not detectably enhance Akt phosphorylation and survival in these transfectants, as it did with Schwann cells transfected with empty vector (FIGS. 25A and 25B). These results establish that the PI3K/Akt signalling pathway can be involved in *T. cruzi* TS-promoted survival of Schwann cells.

In further studies, peptides C44 (SEQ ID NO:12), C14 (SEQ ID NO:14), CFN1 (SEQ ID NO:13), C19Y21 (SEQ ID NO:15), CYN2 (SEQ ID NO:16), CYNF (SEQ ID NO:17), B2 (SEQ ID NO:18) or TR (SEQ ID NO:19) were tested for the capacity to inhibit apoptosis of PC12 cells or Schwann cells. Peptides C44 (SEQ ID NO:12), C14 (SEQ ID NO:14), CFN1 (SEQ ID NO:13), C19Y21 (SEQ ID NO:15) were potent suppressors of apoptosis in the assays. Peptide CYN2 (SEQ ID NO:16) also suppressed apoptosis but was less active than peptides C44 (SEQ ID NO:12), C14 (SEQ ID NO:14), CFN1 (SEQ ID NO:13), C19Y21 (SEQ ID NO:15). The appoptosis suppressing effect of peptides C44 (SEQ ID NO:12), C14 (SEQ ID NO:14), CFN1 (SEQ ID NO:13), C19Y21 (SEQ ID NO:15), CYN2 (SEQ ID NO:16) and CYNF (SEQ ID NO:17) was inhibited by the PI-3 kinase inhibitor LY294002. Peptides CYNF (SEQ ID NO:17), B2 (SEQ ID NO:18) and TR (SEQ ID NO:19) did not inhibit apoptosis in the assays.

Discussion

The results presented here indicate that *T. cruzi* invasion of the nervous system may keep destruction of neurons and glial cells in check (Chuenkova, M. V. and Pereira, M. A., *Mol. Biol. Cell*, 11:1487–1498 (2000)). Indeed, the results described herein establish that *T. cruzi* infection suppresses induced apoptosis of Schwann cells (FIG. 19). The *T. cruzi*-specified survival factor was identified to be their sialidase/sialyl transferase (TS) (FIGS. 20A–20C, 21A and 21B). TS is strategically localized to interact with mammalian cells, as it is present both on the parasite outer membrane (Prioli, R. P. et al., *Trop. Med. Parasitol.*, 42:146–150 (1991)) and in the extracellular milieu as a water-soluble ligand (Cavalesco, R. and Pereira, M. E. A., *J. Immunol.*, 140:617–625 (1988), Pereira, M. E. A. et al., *J. Exp. Med.*, 174:179–191 (1991)). On the surface membrane, TS facilitates binding of trypanosomes to surface receptors of host cells as a prelude to invasion (Ming, M. et al., *Mol. Biochem. Parasitol.*, 59:243–252 (1993)), while in the extracellular environment it expedites reaction with cells that are not permissive to invasion, such as endothelial cells, neurons and lymphocytes (Saavedra, E. et al., *J. Exp. Med.*, 190:1825–1836 (1999), Chuenkova, M. V. and Pereira, M. A., *Mol. Biol. Cell*, 11:1487–1498 (2000)). Because TS can provide trophic support for neuronal cells (e.g., neurons and glial cells) and in keeping with the nomenclature adopted for certain molecules from virus and bacteria, named virokines and bacteriokines (Wilson, M. et al., *Infect. Immun.*, 66:2401–2409 (1998)), respectively, the term "protokine" (protozoan cytokine) is used to refer to a novel class of biologically active protozoan-derived molecules (Saavedra, E. et al., *J. Exp. Med.*, 190:1825–1836 (1999)).

*T. cruzi*, particularly the invasive subset that expresses high levels of TS (TS$^+$ trypomastigotes), as well as TS isolated from *T. cruzi* and the TS catalytic domain expressed in bacteria, activated Schwann cell PI3K/Akt signaling (FIGS. 20A–20C and 22A–22C). Such signaling seems to be the mechanism underlying the anti-apoptotic action of *T. cruzi* because Schwann cells no longer respond to TS when their endogenous PI3K/Akt cascade was inactivated by transfection with relevant inhibitors (FIGS. 24A, 24B, 25A and 25B). In addition to Schwann cells, TS promoted survival and neurite outgrowth of the neuronal PC12 cells and of primary cultures of cerebellar granule neurons in a PI3K/Akt-dependent manner (Example 1). Thus, it is clear that the mechanism of Schwann cell protection induced by *T. cruzi* and the protokine TS involved PI3K/Akt signaling. Therefore, the protokine TS triggers signal transduction cascades similar to those of authentic mammalian cytokines, like IL-3 (Songyang, Z. et al., *Proc. Natl. Acad. Sci. USA*, 94:11345–11350 (1997). *T. cruzi* infection of macrophages triggers PI3K activation as well (Todorov, A. G. et al., *J. Biol. Chem.*, 275:32182–32186 (2000)), though the *T. cruzi*-derived activating factor for this cell type has not been identified.

TS proved to be a strikingly potent trophic factor for Schwann cells and showed efficacy at a dose of about ≧0.5 nM, which is similar to the effective doses reported for other Schwann cell survival factors such as neuroregulin (Greespan, J. B. et al., *J Neurosci.*, 16:6107–6118 (1996)) and lysophosphatidic acid, which has been reported to be active at a dose of >10 nM for primary cultures of rat Schwann cells (Weiner, J. A. and Chun, J., *Proc. Natl. Acad. Sci.*, 96:5233–5238 (1999)). Such potency was evident in the survival of PC12 cells as well, as TS effectively protected the neuronal cells at concentrations lower than those required by nerve growth factor (Example 1).

The neurotrophic action of TS is specific because other *T. cruzi* proteins such as the heparin-binding protein penetrin (Ortega-Barria, E. and Pereira, M. E. A., *Cell*, 67:411–421 (1991)), the protease cruzipan (Murta, A. C. et al., *Mol. Biochem. Parasitol*, 43:27–38 (1990)), and the TS superfamily member TSA-1 (Wrightsman, R. A. et al., *J. Immunol*, 153:3148–3154 (1994)) (FIG. 3), were all ineffective (Chuenkova, M. V. and Pereira, M. A., *Mol. Biol. Cell*, 11:1487–1498 (2000)).

The potent and specific survival promoting activity of *T. cruzi* TS for cells of the nervous system may be relevant to the pathogenesis of Chagas' disease. *T. cruzi* invasion of the nervous system is restricted largely to penetration and subsequent parasite development in glial cells (i.e., Schwann cells) in the peripheral nervous system (PNS) and astrocytes in the central nervous system (CNS) (Da, J. R et al., *Brain Res. Bull.*, 53:153–162 (2000); Tafuri, W. L., *Am. J. Trop. Med. Hyg.*, 19:405–417 (1970); McCabe, R. E. et al., *Exp. Parasitol*, 68:462–469 (1989); Tanowitz, H. B. et al., *Am. J. Trop. Med. Hyg.*, 31:1090–1097 (1982); Wong, W. C. et al., *Histol. Histopathol.*, 7:371–378 (1992)). The majority of individuals infected with *T. cruzi* remain asymptomatic for years or decades and may show evidence of peripheral neuroregeneration, particularly in the GI tract and heart (Köberle, F., *Parasitol*, 6:63–71 (1968)). Animal models of Chagas' disease may also present signs of neurite growth (Losavio, A. et al., *Am. J. Trop. Med. Hyg.*, 41:539–547 (1989)). However, ganglia in the GI tract and heart suffer extensive damage in the relatively few (<15%) patients who progress from the asymptomatic to the chronic stage of Chagas' disease (Andrade, Z. A., *Ciba Found Symp.*, 99:214–33 (1983), Oliveira, J. S. M. et al., *Am. Heart J.*, 109:304–308 (1985)). Such damage is most certainly a cause of cardiomegaly, megaesophagus and megacolon in the chronic patients.

Therefore neuron survival in the PNS is a critical event for the healthy status of chagasic patients, and as described herein, *T. cruzi* TS plays a role in neuroregeneration. Thus, *T. cruzi* TS can result in the prevention of pathology in asymptomatic individuals with Chagas' disease. Consequently, TS and neurotrophic fragment thereof can be used as therapeutics for treating Chagas disease and/or other neurodegenerative diseases.

PI3K signaling has been implicated in some bacterial infections of mammalian cells, specifically Listeria monocytogenes and *E. coli* invasion of epithelial cells and brain microvascular endothelial cells (Ireton, K. et al., *Science*, 274:780–782 (1999), Reddy, M. A. et al., *J. Biol. Chem.* (In Press) (2000)), respectively, as well as *Cryptosporidium parvum* (Forney, J. R. et al., *Infect. Immun.*, 67:844–852 (1999)). Thus, PI3K signaling may be a common mechanism that these and perhaps other microbes use to invade cells. The results of Examples 1 and 2, suggest that *T. cruzi*-induced PI3K/Akt activation helps establish parasitism in mammalian hosts by preventing or reducing damage to the nervous system.

Example 3

TS and Peptides Derived from the Tandem-repeat Domain of TS Induces the Secretion of IL-6

Additional Materials and Methods

Cell Culture

Primary cultures of human intestinal microvascular endothelial cells (HIMEC) isolated from normal jejunal mucosa/submucosal tissue were prepared as described (Strong et al., *Gastroenterology* 114: 1244–1256 (1998)). The HIMEC were cultured in fibronectin-coated plasticware in MCDB medium (Sigma) supplemented with 20% FBS, 90 µg/ml heparin and 50 µg/ml endothelial cell growth factor (Sigma). T-24 cells (ATCC Accession No. HTB-4) were cultured in M199 medium supplemented with 10% FBS. PBMC were purified by Ficoll-Paque gradient as described (*Current Protocols in Immunology*, pp 7.1.1–7.1.2). Vero cells (ATCC Accession No. CCL-81) were grown in RPMI medium with 5% Nu serum and infected with the Silvio X-10/4 of *T. cruzi* as described previously (Chuenkova et al., *J. Exp. Med.* 181: 1693–1703, (1995)).

Cloning and Expression of Catalytic and Long Tandem Repeat Domains of TS

The catalytic domain of TS (TS-F, also referred to as CD) was produced as described in Example 1. The full-length C-terminal long tandem repeat (LTR fragment) of TS from *T. cruzi* clone 7F was isolated as follows: DNA encoding LTR, subcloned from pMelBac plasmid (Invitrogen) containing the TS gene, was digested with Pvu II/Sal I and ligated into EcoR V/Sal I sites of pET20b (Novagen). The LTR encoding DNA was then excised from pET20b using Nco I/Hind III and introduced into the Nco I/Hind III sites of pFASTBAC HTb (Gibco BRL). The Bac-to-Bac system (Gibco BRL) was used to generate recombinant baculovirus, which were used to infect Sf9 cells. Recombinant LTR protein was purified by $Ni^{2+}$-NTA column affinity chromatography (Novagen). The LTR fragment contained the full-length tandem repeat domain of TS from clone 7F (44 repeats) with the 26 amino-terminal and 40 carboxyl-terminal amino acids which flank the repeat domain. Lipopolysaccharide was removed from the purified LTR protein by AffinityPak Detoxi-Gel chromatography.

Preparation of TS-154 and TS-H32 Constructs

Construct TS-154 was derived from enzymatically active trans-sialidase clone 154 of the Y strain of *T. cruzi* (Uemura et al, *EMBO J.* 11: 3837–3844). The N-terminus of clone 154 was amplified by PCR using synthetic DNA primers NU-17 (5'-GCCCATGGCACCCGATCGAGCCGAGTT-3', SEQ ID NO:20) and NU-18 (5'-CGGAATTTTCATCAC-CAATG-3', SEQ ID NO:21) which contained Nco I and Bgl II sites, respectively. NU-17 was designed to introduce starting ATG codon just prior to the N-terminus of mature TS protein, and a NcoI site for subcloning. The PCR product obtained using NU-17 and NU-18 were treated with Nco I and BgI II, and subcloned into the Nco I and Bam HI sites of pET-21d (Novagen, Milwaukee, Wis.). Most of the 12 amino acid repeats and hydrophobic region at the C-terminus were removed by PCR using synthetic DNA primers NU-19 (5'-GTTCCGAACGGTTTGAAGTTTGCG-3', SEQ ID NO:22) and NU-20 (5'-GTTCCGAACG-GTTTGAAGTTTGCG-3', SEQ ID NO:23). NU-20 corresponds to the partial sequence of the tandem repeat and, in addition, it contains a Sal I site. The PCR product with the minimum numbers of repeats (i.e., 5 repeats) was selected and used to replace the original C-terminus of clone 154 at unique Mlu I site (FIG. 15A). The DNA fragment with unique BamHI/Sal I sites was ligated to the pET-21d plasmid containing the N-terminal region of TS using the Bam HI and Xho I sites of the vector, to yield construct TS-154 (FIG. 4A). To generate construct TS-H32, the Bgl II/Pst I DNA fragment of pTS-154 was replaced with the corresponding fragment from the gene 121 (Uemura. J., et al., EMBO J. 11: 3837–3844, (1992)). The trans-sialidase encoded by gene 121 is catalytically inactive due to a single amino acid difference in the Bgl Ii/Pst I fragment, with histidine (H374) replacing tyrosine in the catalytically active TS 154 (Uemura. J., et al., EMBO J. 11: 3837–3844, (1992)). Thus, construct TS-H32 was inactive (FIG. 15B). All constructs were verified by automated sequencing (ABI Perkin Elmer) using BIGDYE terminator. Production and purification of TS-154 and TS-H32 proteins was identical to the method described above for the TS-F construct.

Immunoassays for Cytokines

Endothelial cells and T-24 cells were plated on 24-well plates at a density of $1 \times 10^3$ cells/well, while peripheral blood mononuclear cells (PBMC) were plated in the similar wells at $1 \times 10^6$/well. Triplicat cultures of cells were incubated test agents for a predetermined amount of time. Polymixin B was used at 10 µg/ml in all cell cultures, as it did not affect any parameter tested. Cytokines and chemokines released in the culture supernatants were measured by ELISA assay following the instructions of the manufacturer (Endogen). The cytokines tested were IL-1β, IL-4, IL-8, IL-10, IL-12, IFN-γ, TNF-α, and the chemokines RANTES and MCP-1. Negative controls were cells incubated in medium containing polymixin B at 10 µg/ml, and positive controls were cells incubated with bacterial LPS at the low ng/ml range (for PBMC or HIMEC) or in the µg/ml range for carcinoma T-24 cells. In some experiments, IL-1β or TNFα were used as positive control for cytokine release.

Bioassay for IL-6

Bioassay for IL-6 was performed using IL-6 dependent human DS-1 cells (Bock et al., Cytokine 5: 480–489 (1993), ATCC Accession No. CRL-11102). Briefly, $1 \times 10^4$ cells/well were plated in 96-well plates and incubated for 24 hrs in IL-6-free medium (10% FCS in RPMI) containing several dilutions of TS-conditioned media or exogenous rIL-6. The cultures were pulsed with 0.5 µCi $^3$H-thymidine for 4 hrs and harvested to determine radioactivity incorporation using a microplate scintillation instrument (Packard). In some studies, a neutralizing anti-IL-6 rabbit IgG or normal rabbit IgG (Endogen) was added to the dilutions of TS-conditioned prior to assaying for growth-stimulation of DS-1 cells. TS conditioned media was prepared by incubating PBMC or T-24 cells for 24 hr in 10% FCS/RPMI without (CM) or with (TS/CM) TS at 1 µg/ml. Supernatants were centrifuged at 1,000× g to remove cell debris and were kept frozen at −20° C. until use.

Polymerase Chain Reaction of Reverse-Transcribed mRNA

Semiquantitative analysis of cytokine mRNA was performed by the primer-dropping method (Wong et al., Anal. Biochem. 223:251–258, 1996)). RNA of endothelial cells ($1 \times 10^5$) or PBMC ($1 \times 10^6$), that were or were not stimulated with TS at 1 µg/ml for 24 hr, was purified by acid guanidinium isothiocyanate-phenol-chloroform-TRI reagent (Molecular Research Center). Two µg of total RNA were converted to cDNA in a volume of 20 µl using random hexamer primers according to the manufacturer's instructions (GIBCO-BRL). Synthetic DNA primers for human IL-6 were 5'ATGAACTCCTTCTCCACAAGCGC (SEQ ID NO:24)and 5'GAAGAGCCCTCAGGCTGGACTG (SEQ ID NO:25), and for GAPDH were those described in Example 1 (SEQ ID NO:10 and SEQ ID NO:11). The PCR mixture contained 20 mM Tris-HCl pH 8.4, 50 mM KCl, 1.5 mM MgCl$_2$, 1 mM dNTP, 200 pM primers and 1 U of Taq polymerase in 50 µl. Thermal cycling conditions were: denaturation step 95 degrees for 5 min; 35 cycles of 95 degrees 30 sec, 60 degrees 30 sec and 75 degrees 1 min, and a final step of 75 degrees for 5 min. At cycle number 9, GAPDH primers were added. Five microliters of the PCR product were alalyzed by electrophoresis through 2% agarose-gel in the presence of 1 µg/ml ethidium bromide.

LTR Depletion

Two hundred microliters of Sepharose-G protein (Pharmacia) were adsorbed with culture supernatants of the mAb TCN (IgG1 isotype) or of a control mAb IgG1 specific for p-azo-phenylarsonate (kindly provided by Dr. Thereza Imanishi-Kari, Tufts Medical School, Boston, Mass.), washed with 20 vols of LPS-free PBS, pH 7.2. Three micrograms of LTR were loaded to either protein G/TCN-2 or protein G/control IgG1 column. The effluent was reapplied 5 times to the respective column. The last flow-through of each column was collected in 200 µl in a separate LPS-free tube, and the columns were washed with five column volumes of PBS. Elution of bound LTR was by mixing the resins with a spatula and centrifugation at 250× g for 5 min at 4° C. Effluents and eluates were constituted to the original volume and added to T-24 cells. After 24 hr, IL-6 in the T-24 cell supernatants were determined by ELISA.

IL-6 Production by PBMC Stimulated with TR Peptides

TR peptides (Table 2) were synthesized at the Tufts Synthesis Facility (Boston, Mass.). Each peptide was purified by HPLC, and the number of amino acids and molecular weight of each peptide verified by mass spectrometry. Peptides were dissolved in growth medium (10% FCS in RPMI) and added at various concentrations to $1 \times 10^6$ PBMC/well in 24-well plates. After 24 hrs, IL-6 was assayed by ELISA in the conditioned supernatants.

TABLE 2

TR peptides

| Peptide | Amino Acid Sequence | |
|---|---|---|
| TR1 | DSSAHGAPSTPA | (SEQ ID NO:32) |
| TR2 | DSSAHGAPSTPADSSAHGTPSTPV | (SEQ ID NO:26) |
| TR3 | DSSAHGAPSTPADSSAHGTPSTPVDSSAHGTPSTPA | (SEQ ID NO:27) |

TABLE 2-continued

TR peptides

| Peptide | Amino Acid Sequence | |
|---|---|---|
| TR4 | DSSAHGAPSTPADSSAHGTPSTPVDSSAHGTPSTPADSSAHSTPSTPA | (SEQ ID NO:28) |
| TR5 | DSSAHGAPSTPADSSAHGTPSTPVDSSAHGTPSTPADSSAHSTPSTPADSSAHSTPSTPA | (SEQ ID NO:29) |

Peptides TR1, TR2, TR3, TR4 and TR5 are derived from the amino acid sequence of the protein encoded by clone 7F (GenBank accession number M61732).

Results

HIMEC monolayers were cultured with various concentrations of purified TS for 24 hrs and the concentration of eight cytokines (IL-1β, IL-4, IL-6, IL-8, IL-10, L-12, INF-γ and TNF-β) and two chemokines (RANTES and MCP-1) in the conditioned HIMEC supernatants was measured. The concentration of IL-6 was elevated in the conditioned supernatants in a manner dependent on the TS input (FIG. 12A). In contrast, the concentration of the other cytokines did not increase in response to TS stimulation under condition in which bacterial LPS at 50 ng/ml released IL-1 β, IL-8 and TNF-α. Similar IL-6 upregulation was observed with two other primary cultures of HIMEC. The quantity of IL-6 produced by HIMEC in response to 1 μg/ml of TS corresponded to that induced by 50 ng/ml of a bacterial LPS. A control neuraminidase (VCNA) did not stimulate detectable IL-6 secretion in HIMEC (FIG. 12A) suggesting that the IL-6 secretion inducing action of TS did not depend on its intrinsic glycosidase activity. Another control protein, the *T. cruzi* heparin-binding penetrin (PN-1) thought to promote parasite invation (Ortega-Barria et al., Cell 67: 411–421 (1991)), was not effective in stimulating IL-6 secretion (FIG. 12A), further emphasizing the selectivity of the TS action.

TS also stimulated IL-6 release in normal peripheral blood mononuclear cells (PBMC) (FIG. 12B), another class of human cells relevant to the immunity against *T. cruzi*. Similar results were obtained with PBMC obtained from three other blood donors. In addition, TS stimulated IL-6 secretion in the human bladder carcinoma T-24 cell line (FIG. 12C). Previous workers shows that T-24 cells express IL-6 constitutively and in response to cytokine stimuli (Bubenik et al., Int. J. Cancer 11: 765–773 (1973); Yasukawa et al., EMBO J. 6: 2939–2945 (1987)). Interestingly, the IL-6 produced upon 24 hr-stimulation of T-24 carcinoma cells with 1 μg/ml of TS corresponded to that induced by 0.75 μg/ml of bacterial LPS under the same conditions. Thus, in this cancer cell line, TS was nearly as good as bacterial LP in stimulating IL-6 secretion.

IL-6 is produced by a large variety of cells, including endothelial cells, monocytes, fibroblasts, keratinocytes, T cells, mast cells, neutrophils, tumor cell lines, and cells of neural origin (Stein et al., Drug Discovery Today 3: 202–213 (1998)). TS stimulates IL-6 production in endothelial cells and PBMC, and it is likely that the neuraminidase will also stimulate IL-6 release in other cell types. However, normal human neutrophils, which are capable of secreting IL-6 in response to some stimuli (Cicco et al., Blood 75: 2049–2052 (1990)), did not produce detectable IL-6 when stimulated with TS under condition in which TNF-a did elicit secretion of IL-6.

Kinetics of TS-Dependent IL-6 Secretion

The kinetics of TS-induced IL-6 secretion revealed maximum effect after 24-hr stimulation in both HIMEC and PBMC (FIGS. 12D and 12E). This response proceeded the upregulation of IL-6 transcripts, which was maximal 4–10 hrs after TS stimulation (FIG. 13). These results suggest tht TS triggers synthesis and then secretion of IL-6, consistent with the effect of conventional cytokine agonists in the same cell types (Nilsen et al., Gut 42: 635–642 (1998); Bubenik et al., Int. J. Cancer 11: 765–773 (1973)).

TS-conditioned Cell Supernatants Restore Growth of an IL-6-Dependent B-Lymphoma Cell Line The DS-1 B-lymphoma cells have an intact IL-6 receptor signaling pathway, but because they cannot produce IL-6, the cells will die unless exogenous human IL-6 is added to the culture medium (Bock et al., Cytokine 5: 480–489 (1993)). This cell line was used to assay conditioned culture media for biologically active IL-6.

Conditioned media were prepard by incubating PBMC or T-24 cells for 24 hr in 10% FCS/RPMI without (CM) or with (TS/CM) TS at 1 μg/ml. Conditioned media from cells stimulated with TS (TS/CM), but not cells cultured in media along, restored growth of the DS-1 lymphoma cells in a dose-dependent manner, and a neutralizing IL-6 antibody suppressed the growth-promoting activity (FIG. 14). These results demonstrate that IL-6 produced by PBMC or T-24 cels, after culture with TS is biologically active. In addition, TS is not an IL-6 receptor agonist because it did not restore growth of the DS-1 cells when added to normal growth medium lacking exogenous IL-6 (FIG. 14).

TS Mediates IL-6 Release Through its C-Terminal Tandem Repeat

The IL-6 secretion-inducing activity of the catalytically inactive TS mutant TS-H32 and the catalytically active TS-154 protein were assessed. Both TS-H32 and TS-154 constructs contain 5 tandem repeat units (FIG. 15A). Although TS-H32 differs from TS-154 in six amino acid substitutions in the catalytic domain (FIG. 15A), the difference in enzymatic activity between the two constructs is attributed to a single amino acid, with tyrosine (Y374) in the active enzyme (TS-154) mutated to histidine in the inactive enzyme (TS-H32) (FIGS. 15A and 15B). Surprisingly, enzymatically-active TS-154 was as powerful as enzymatically-inactive TS-H32 in stimulating IL-6 secretion in PBMC (FIG. 15C) and T-24 cells.

The results with the TS-154 and TS-H32 constructs suggest tht the catalytic activity of TS does not mediate IL-6 release in naive cells. This was confirmed with the use of recombinant catalytic domain of TS.

The catalytic domain of TS (CD, also referred to as TS-F) did not promote IL-6 release from T-24 cells, whereas LTR effectively induced release of IL-6 in a dose-dependent manner (FIG. 16A). Similar results were obtained in cultures of PBMC, in which LTR, but not CD, upregulated IL-6 release. To confirm that LTR mediated IL-6 release, we depleted LTR from solution in a protein G-Sepharose column adsorbed with TCN-2. The flow-through of the TCN-2 affinity column, which was devoid of LTR polypeptide as determined by immunoblot analysis did not stimulate IL-6 release in T24 cell cultures (FIG. 16B). In contrast, the flow-through of a control IgG1 column did contain LTR polypeptide and stimulated IL-6 secretion (FIG. 16B). Furthermore, elution of LTR from the TCN-2/protein G column, restored the IL-6-secretory power of the original preparation, while similar elution from the IgG1 control column did not (FIG. 16B). These results establish that LTR induced IL-6 secretion in naive human cells.

Synthetic Peptides Based on LTR Induced IL-6 Secretion

Synthetic peptides TR1 (SEQ ID NO:32), TR2 (SEQ ID NO:26), TR3 (SEQ ID NO:27), TR4 (SEQ ID NO:28) and TR5 (SEQ ID NO:29), which correspond to the 12, 24, 36, 48 and 60 amino acid sequences proximal to the C-terminus of the catalytic domain of TS (*T. cruzi*, Silvio Stain) (Table 2) (Pereira et al., *J. Exp. Med.* 174: 179–191, 1991). The IL-6 secretion-inducing activity of the synthetic peptides was assessed in cultures of PBMC. Peptides TR4 (SEQ ID NO:28) and TR5 (SEQ ID NO:29) were active in promoting IL-6 release, while TR1 (SEQ ID NO:32), TR2 (SEQ ID NO:26) and TR3 (SEQ ID NO:27) were less active (FIG. 17). The results with TR peptides confirm that the tandem repeat is the TS moiety that mediates IL-6 release in naive human cells.

HIMEC Strongly Induces IL-6 Secretion When Infected with *T. cruzi* Trypomastigote Populations Bearing a TS⁺ but not a TS⁻ Phenotype Extracellular trypomastigotes can be subdivided into two populations based upon the relative abundance of TS (Pereira, M. E. A., et al., *Infect. Immun.*, 64:3884–3892 (1996)). These two populations can be readily separated from one another by differential affinity to magnetic beads coated with LTR-specific mAb TCN-2. The subset that produces TS (TS⁺) represents about 25% of the total trypomastigote population, while the subset that does not produce or produces very little TS (TS⁻) constitutes the majority of trypomastigotes (Pereira, M. E. A., et al., *Infect. Immun.*, 64:3884–3892 (1996)). TS⁺ parasites of the Silvo strain are short and stumpy (length=9.3±2.8 μm) and morphologically distinct from TS⁻ parasites, which are slender (length=18.2±4.3 μm) (FIG. 18C). Live TS⁺ trypomastigotes moved slowly and sluggishly in liquid medium (RPMI/10% FCS) at room temperature. In contrast, TS⁻-trypomastigotes migrated through liquid media swiftly with a whipping movement. However, the dimorphism and contrasting movements of TS⁺ and TS⁻ trypomastigotes were not characteristic features of two other *T. cruzi* strains, Tulahuen and MV-13. Thus, there does not appear to be a relation between the expression of TS and a particular morphological type of *T. cruzi*.

Nevertheless, the availability of purified TS⁺ and TS⁻ populations offered a unique opportunity to test the capacity of live parasites with variable abundance of TS to induce IL-6 secretion by normal human cells. HIMEC monolayers were challenged with live TS⁺ and TS⁻ parasites and the secretion of IL-6 was assessed over time. TS⁺ trypomastigotes were much more effective than TS⁻, and somewhat better than unfractionated trypomastigotes, in inducing release of IL-6 (FIG. 18B). The results presented in FIG. 18B are from studies using the Silvio strain. Similar results were obtained in studies using the Tulahuen strain. Because the TS⁺ parasites of the Tulahuen strain are a mixture of stumpy and slender forms, the power of *T. cruzi* to induce IL-6 secretion in naive human cells is dependent on the expression level of TS and not on the morphology of the parasite. Furthermore, *Leishmania major* promastigotes which do not have TS activity (FIG. 18A) do not induce IL-6 secretion in HIMEC (FIG. 18B). Thus, parasite burden per se does not suffice to induce IL-6 secretion in naive human cells.

Discussion

Infection of mammals by parasites and other microbes results in the release of cytokines and other mediators of the inflammatory response. The composition of the cytokines, which depends on the nature of the infecting oranism and on the host genotype, may be critical for the resistance or susceptibility to microbial invation, as best exemplified by the infection of mice with the protozoan *Leishmania major* (Reiner et al., *Annu. Rev. Immunol.* 13: 151–177 (1995)) and of humans with the bacterium *Mycobacterium leprae* (Yamamura et al., *J. Immunol.* 149: 1470–1475 (1992)).

It is generally accepted that cytokine networks result from antigenic stimulation of lymphocytes and macrophages. However, these antigen-driven host responses can be subverted by a group of viral and bacterial proteins, termed virokines and bacteriokines, which are capable of changing the dynamics of the cytokine networks without directly activating B and T cell receptors (Wilson et al., *Infect. Immun.* 66: 2401–2409 (1998)). Virokines tend to suppress host immune responses by neutralizing inflammatory cytokines, as is the case of the protein B15R of vaccinia virus, which binds IL-1β (Alcami et al, *Cell* 71: 153–167 (1992)). Alternatively, virokines may down-modulate immune responses by mimicking anti-inflammatory cytokines, like the protein BCRF1 of Epstein-Barr virus, which is 70% identical to IL-10 (Hsu et al., *Science* 250: 830–832 (1990)). On the other hand, bacteriokines, including lipopolysaccharides (LPS) and exotoxins, are more likely to stimulate proinflammatory cytokines, thereby enhancing pathogenesis (Wilson et al., *Infect. Immun.* 66: 2401–2409 (1998)). Whether protozoan parasites can alter host immune responses through molecules functionally equivalent to virokines and bacteriokines (i.e., "protokines") remains to be determined. The findings described herein identify TS as a protein that can alter the dynamics of the cytokine network by upregulating IL-6 secretion in normal human cells. As described herein, TS and its tandem repeat induced secretion of IL-6 by naive microvascular endothelial cells and PBMC. Furthermore, given that IL-6 may be produced by many other cell types, such as fibroblasts and epithelial cells, the range of target cells for IL-6 release by TS is broader than the vascular endothelium and blood mononuclear cells. This was indicated by the ability of TS to induce IL-6 release in the T-24 bladder carcinoma cells (FIG. 12C) and by parallel experiments with mouse cells, which revealed TS to be an upregulator of IL-6 secretion in naive splenocytes, bone marrow cells, and peritoneal cells from BALB/c and other strains of mice. TS, therefore, upregulates IL-6 secretion in various cell types and mammalian species.

The kinetics of TS-dependent IL-6 release in vitro (FIGS. 12D, 12E and 13) suggests that, in vivo, TS can stimulate IL-6 release prior to the full development of acquired immune response against *T. cruzi*. This could be accomplished when *T. cruzi* first encounters the mammalian host, such as after an insect bite, when the parasites enter the host through the mucosa, usually around the eye. Or when *T. cruzi* enter the host during blood transfusion or congenitally, in which case the TS parasites gain access into the circulation, where they can react with endothelial cells and PBMC to trigger IL-6 release. In addition, TS can also promote IL-6 secretion in vivo as a soluble mediator. Indeed, soluble neuraminidase was detected, before the parasites, in the blood of a *T. cruzi*-infected individual (DeTitto et al., *Clin. Immunol. Immunopathol.* 46: 151–157 (1988)). Copious amounts of the enzyme are released in monolayers of cells infected with *T. cruzi* (Scudder et al., *J. Biol. Chem.* 268: 9886–9891 (1993)). The findings reported herein further show that soluble enzyme and TS-expressing parasites are capable of inducing IL-6 secretion in normal cells.

There are several ways in which TS-dependent IL-6 could alter *T. cruzi* invasion. IL-6 promotes polyclonal activation of B and T lymphocytes (Kishimoto, T. *Blood* 74: 1–10 (1989); Uyttenhove et al., *J. Exp. Med.* 167: 1417–1427 (1988)) and is an important cofactor for Th2 T cell activation, necessary for the induction of humoral immune responses (Rincon et al., *J. Exp. Med.* 185: 461–469 (1997)). Thus, the TS/IL-6 pathway could be directly relevant to the polyclonal lymphocyte responses that characterize acute Chagas' disease (Minoprio et al., *J. Immunol.* 24: 661–668 (1986)). In addition, IL-6 is a potent inducer of collagen secretion in human fibroblasts (Duncan et al., *J. Invest. Dermatol.* 97: 686–692 (1991)), and as such appears to underlie the pathogenesis of systemic sclerosis, a connective tissue disease characterized by fibrosis in the skin and internal organs (Kawaguchi et al., *J. Clin. Invest.* 103: 1253–1260 (1999)). The fibrogenic action of IL-6 could also be relevant to *T. cruzi* infection, as fibrosis is a prominent feature of acute and chronic Chagas' disease (Köberle, F., In Ciba Found Symp 20, pp 137–147, 1974; Andrade, Z. A. In Ciba Found. Symp. 99: 214–233 (1983)). Because chronic chagasic heart contains many IL-6-containing mononuclear cells and endothelial cells (Chandrasekar et al., *Biochem. Biophys. Res. Commun.* 233: 365–371 (1996); Zhang et al., *Exp. Parasitol.* 84: 203–213 (1996)), IL-6 could contribute to the fibrosis in the chronic heart, regardless of the mechanism stimulating production of the cytokine.

IL-6, in addition to mediating inflammatory and immune responses, can play an important role in a variety of central and peripheral nervous systems, such as cell-to-cell signaling, protection of neurons from insult, as well as neuronal growth and survival (Gruol et al., *Mol. Neurobiol.* 15: 307–339 (1997)). Thus, TS-dependent IL-6 can be a factor in the neuroregeneration that characterizes the indeterminate phase of Chagas' disease in humans (Köberle, F. In Ciba Found. Symp. 20: pp. 137–147 (1974)) and animals (Tafuri, W. L., *Am. J. Trop. Med. Hyg.* 19: 405–417 (1970)).

As described herein, TS is extremely potent in protecting several types of neuronal cells from undergoing apoptosis induced by growth factor deprivation. Furthermore, the TS-induced neuroprotection was syngergistic with two members of the IL-6 family, ciliary neurotrophic factor (CNTF) and leukemia inhibitory factor (LIF) (See Example 1). Thus, the neurotrophic effect of TS-dependent IL-6 could be boosted by the action of TS and by the TS synergy with CNTF or LIF on the neurons.

While this invention has been particularly shown and described with references to preferred embodiments thereof, it will be understood by those skilled in the art that various changes in form and details may be made therein without departing from the spirit and scope of the invention as defined by the appended claims.

What is claimed is:

1. An isolated neurotrophic peptide consisting of the amino acid sequence of peptide C14 (SEQ ID NO:14).

2. A composition, comprising the isolated neurotrophic peptide of claim 1 and a physiologically acceptable carrier.

3. The composition of claim 2, further comprising a mammalian neurotrophic factor.

4. The composition of claim 3, wherein said mammalian neurotrophic factor is ciliary neurotrophic factor (CNTF) or leukemia inhibitory factor (LIF).

5. A fusion protein comprising a first moiety and a fusion partner moiety, wherein said first moiety consists of the amino acid sequence of peptide C14 (SEQ ID NO:14) and said fusion partner moiety consists of an oligopeptide or polypeptide not occurring in *T. cruzi* trans-sialidase (SEQ ID NO:34) as found in nature.

6. The fusion protein of claim 5, wherein said fusion partner moiety is a mammalian neurotrophic factor.

7. The fusion protein of claim 6, wherein said neurotrophic factor is ciliary neurotrophic factor (CNTF) or leukemia inhibitory factor (LIF).

8. A composition, comprising the fusion protein of claim 5 and a physiologically acceptable carrier.

* * * * *